US007008664B1

(12) United States Patent
Shen

(10) Patent No.: US 7,008,664 B1
(45) Date of Patent: *Mar. 7, 2006

(54) METHOD FOR IMPROVING THE CARCASS QUALITY OF AN ANIMAL

(75) Inventor: Jennie Bih-Jien Shen, Wilmington, DE (US)

(73) Assignee: E. I. du Pont de Nemours and Company, Wilmington, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/326,285

(22) Filed: Jun. 7, 1999

Related U.S. Application Data

(60) Provisional application No. 60/088,987, filed on Jun. 11, 1998.

(51) Int. Cl.
*A23K 1/00* (2006.01)
*C12N 15/82* (2006.01)

(52) U.S. Cl. ..................... 426/635; 800/281
(58) Field of Classification Search ............ 426/2, 426/615, 635; 424/195.1; 800/281, 300.1, 800/320.1
See application file for complete search history.

(56) References Cited

U.S. PATENT DOCUMENTS

| | | | |
|---|---|---|---|
| 5,107,065 A | 4/1992 | Shewmaker et al. | 800/205 |
| 5,231,020 A | 7/1993 | Jorgensen et al. | 435/172.3 |
| 5,443,974 A * | 8/1995 | Hitz et al. | 800/264 |
| 5,530,186 A | 6/1996 | Hitz et al. | 800/205 |
| 5,704,160 A | 1/1998 | Bergquist et al. | 47/58 |
| 5,706,603 A | 1/1998 | Bergquist et al. | 47/58 |
| 5,955,330 A * | 9/1999 | Vasil et al. | 800/292 |
| 6,307,123 B1 * | 10/2001 | Kriz et al. | 800/282 |
| 6,350,934 B1 * | 2/2002 | Zwick et al. | 800/281 |
| 6,433,252 B1 | 8/2002 | Kriz et al. | |

FOREIGN PATENT DOCUMENTS

| | | |
|---|---|---|
| EP | 0 794 250 A1 | 9/1997 |
| WO | WO 91/13972 | 9/1991 |
| WO | WO 93/21320 | 10/1993 |
| WO | WO 94/11516 | 5/1994 |
| WO | WO94/11516 | 5/1994 |
| WO | WO-9411516 A1 * | 5/1994 |
| WO | WO-9507344 A1 * | 3/1995 |
| WO | WO 95/22598 | 8/1995 |
| WO | WO 97/10328 | 3/1997 |
| WO | WO 99/60129 | 11/1999 |

OTHER PUBLICATIONS

Machev et al. (Zhivotno"vdni Nauki, (1996) vol. 33, No. 3, p. 23-26).*
Cooke et al. (Anim. Prod. (1971) Volume date 1970, 14(P1. 2) 219-28, ABSTRACT only).*
Pietrzkowkski et al. (Experimental Cell Research, 193, 283-290 (1991)).*
Chan et al. (Plant Molecular Biology 46 :131-141, (2001)).*
Omilli et al. (Molecular and Cellular Biology, Jun. 1986, p. 1875-1885).*
DuPont Specialty Grains Poultry Research Trail AFG6063. Jun. 1998.*
DuPont Specialty Grains Poultry Research Trail AFG66124. Jun. 1998.*
DePont Specialty Grains Poultry Research Trail AFG6088. 1998.*
DuPont Specialty Grains Poultry Research Trail AFG6024. 1998.*
DuPont Specialty Grains Poultry Research Trail AFG6071. 1998.*
DuPont Specialty Grains Poultry Research Trail AFG6090. 1998.*
Soderlund et al. Nutritional Insights, vol. 2, No. 1, 1999, Benefits of feedium OPTIMUM* High Corn to Finishing Beef Cattle Introduction/Nutritional Considerations.*
Broun et al, Science 282: 131-133, Nov. 13, 1998.*
Van de Loo et al, Proc Natl. Acad Sci, USA, 92: 6743-6747, Jul. 1995.*
Doerks et al, TIG 14(6): 248-250, Jun. 1998.*
Smith et al, Nature Biotechnology 15: 1222-1223, Nov. 1997.*
Brenner, S. E., TIG 15(4): 132-133, Apr. 1999.*
Bork et al, TIG 12(10): 425-427, Oct. 1996.*
De Luca, V, AgBiotech News and Information 5(6): 225N-229N, 1993.*
Lee, K. et al., Genes enclodng oleosins in maise kernel of inbreds Mo17 and B73, *Database EMBL, Accession No. U13701*, Jun. 10, 1995.
Varagona, M. et al., Implications for the cis-requirements for Ds transposition based on the sequence of the wxB4 element, *Database EMBL Accession No. X51636*, Nov. 13, 1996.
Ting, Julie T.L. et al., Oleosin of Plant Seed Oil Bodies Is Correctly Targeted to the Lipid Bodies in Transformed Yeast, *The Journal of Biological Chemistry*, 272(6), 3699-3706, 1997.

(Continued)

*Primary Examiner*—Elizabeth F. McElwain

(57) ABSTRACT

A method for improving the carcass quality of an animal is described. This method invovles the preparation and use of nucleic acid fragments comprising all or substantially all of a corn oleosin promoter, a stearoyl-ACP desaturase and a delta-12 desaturase which can be used individually or in combination to modify the lipid profile of corn are described. Chimeric genes incorporating such nucleic acid fragments and suitable regulatory sequences can be used to create transgenic corn plants having altered lipid profiles are also described.

2 Claims, 19 Drawing Sheets

OTHER PUBLICATIONS

Figure 1A:
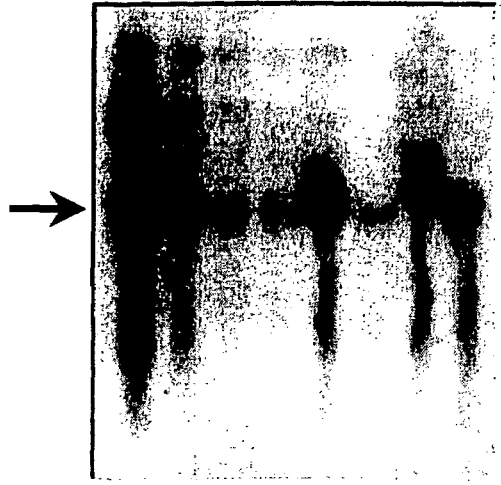
Figure 1B:
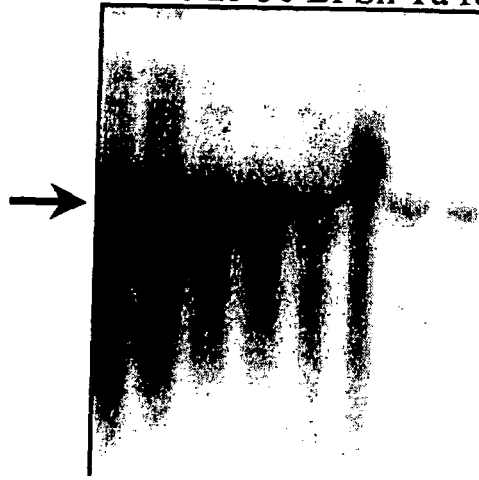
Figure 1C:
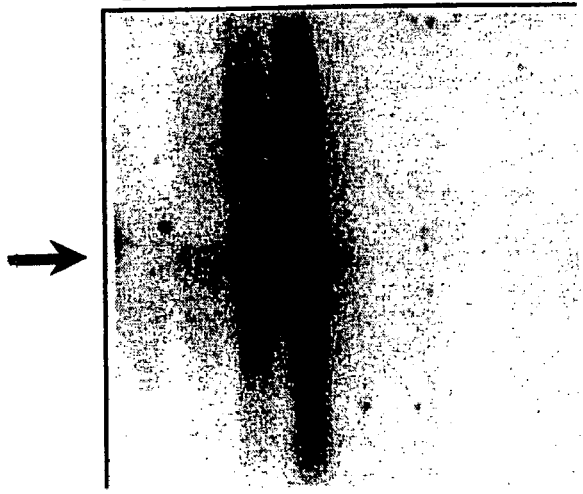
Figure 1D:
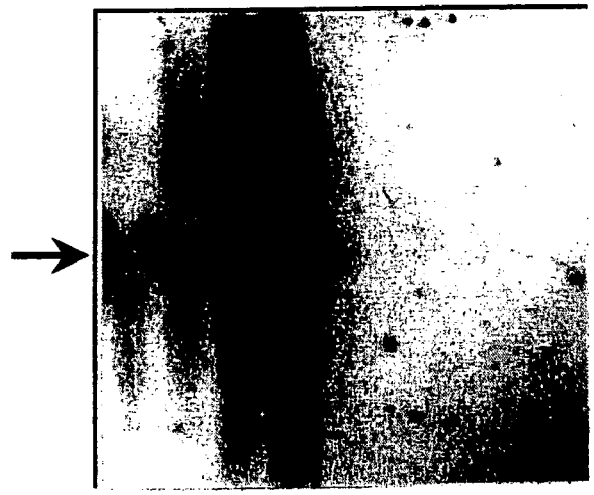
Figure 1E:
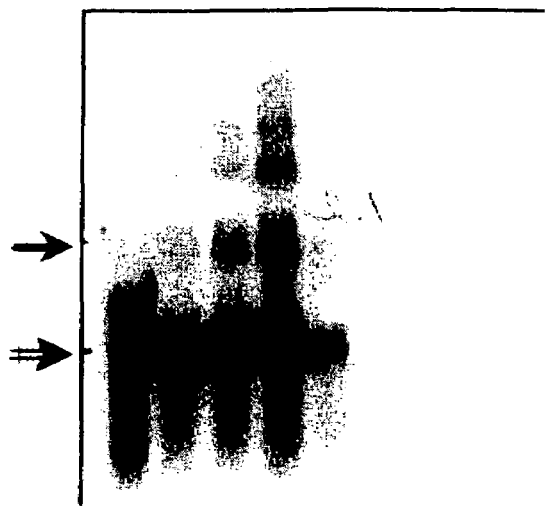
Figure 1F:
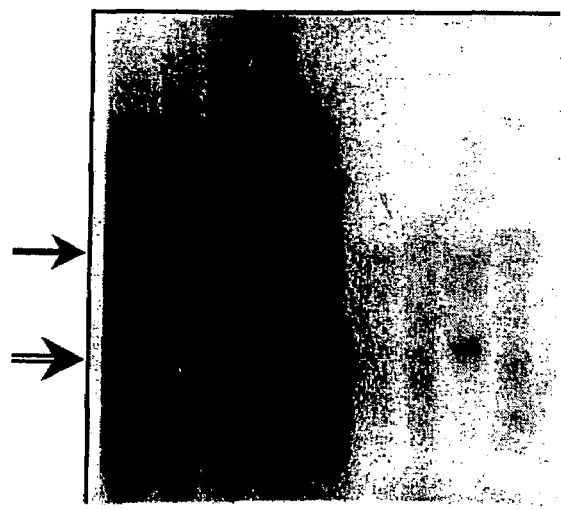

Plant, Arine L. et al., Regulation of an *Arabidopsis* oleosin gene promoter in transgenic *Brassica napus*, *Plant Molecular Biology*, 25, 193-205, 1994.

Parmenter, D.L. et al., Production of biologically active hirudin in plant seeds using oleosin partitioning, *Plant Molecular Biology*, 29, 1167-1180, 1995.

Harwood, John, Lipid Metabolism in Plants, *Critical Review in Plant Sciences*, 8(1), 1-43, 1989.

McKeon, Thomas A. et al., Purification and Characterization of the Stearoyl-acyl Carrier Protein Desaturase and the Acyl-acyl Carrier Protein Thioesterase from Maturing Seeds of Safflower, *The Journal of Biological Chemistry*, 257(20), 12141-12147, 1982.

Knutzon, Deborah S. et al., Modification of *Brassica* seed oil by antisense expression of a stearoyl-acyl carrier protein desaturase gene, *Proc. Natl. Acad. Sci. USA*, 89, 2624-2628, Apr. 1992.

Huang, A.H.C., Lipid Bodies, *Modern Methods of Plant Analysis*, 1, 145-151.

Lee, Keunmyoung et al., Genes encoding oleosins in maize kernel of inbreds Mo17 and B73, *Plant Molecular Biololgy*, 26, 1981-1987, 1994.

Qu, Rongda et al., Oleosin KD 18 on the Surface of Oil Bodies in Maize, *The Journal of Biological Chemistry*, 265(4), 2238-2243, 1990.

Vance, Vicki Bowman et al., Expression of Lipid Body Protein Gene during Maize Seed Development, *The Journal Of Biological Chemistry*, 263(3), 1476-1481, 1988.

Belanger, Faith C. et al., Molecular Characterization of the Major Maize Embryo Globulin Encoded by the Glb1 Gene, *Plant Physiol.*, 91, 636-643, 1989.

Okamuro, Jack K. et al., Regulation of Plant Gene Expression: General Priniciples, *The Biochemistry of Plants*, 15, 1-82, 1989.

Vance, Vicki Bowman et al., The Major Protein from Lipid Bodies of Maize—Characterization and Structure on cDNA Cloning, *The Journal of Biological Chemistry*, 262(23), 11275-11279, 1987.

Shah, F. H. et al., Nucleotide sequence of a complementary DNA clone encoding stearoyl-Acyl-carrier protein, *Database EMBL, Accession No. U68756*, Oct. 14, 1997.

Akagi, Hiromori et al., Nucleotide Sequence of a Stearoyl-Acyl Protein Desaturase cDNA from Developing Seeds of Rice, *Plant Physiology*, 108, 845-846, 1995.

Walbot, V., Maize ESTs from various cDNA libraries sequenced at Stanford University, *Database EMBL, Accession No. A1674009.1*, May 21, 1999.

Shanklin et al., Stearoyl-Acyl-Carrier-Protein Desaturase From Higher Plants is Structurally Unrelated to the Animal and Fungal Homologs, Proc. Natl. Acad. Sci., Mar. 1991, pp 2510-2514, vol. 88.

* cited by examiner

Globulin-1

Embryo, DAP  Aleu
15 20 25 30 20 Lf Sh Ta Rt

Globulin-1

Embryo, DAP  Aleu
15 20 25 30 20 Lf Sh Ta Rt

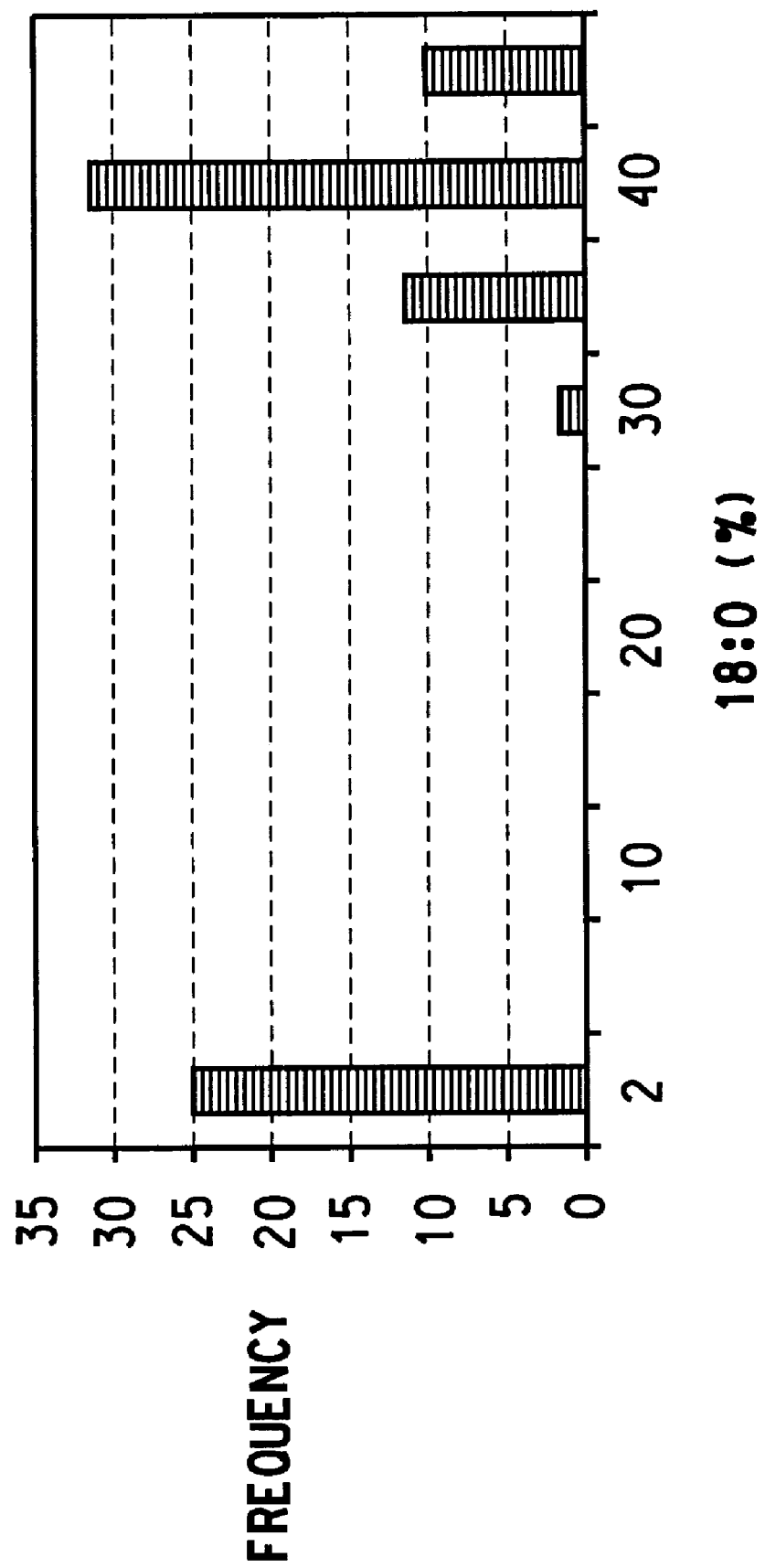

Avg: 12-1.3-70-15-1.4
Wt: 14-1.5-15-68-1.7

SEQUENCE LISTING

<160> NUMBER OF SEQ ID NOS: 59

<210> SEQ ID NO 1
<211> LENGTH: 1790
<212> TYPE: DNA
<213> ORGANISM: Zea mays

<400> SEQUENCE: 1

```
cggcctctcc cctccctcct ccctgcaaat cctgcagaca ccaccgctcg tttttctctc      60
cgggacagga gaaaggggga gagagaggtg aggcgcggtg tccgcccgat ctgctctgcc     120
ccgacgcagc tgttacgacc tcctcagtct cagtcaggag caagatgggt gccggcggca     180
ggatgaccga gaaggagcgg gagaagcagg agcagctcgc ccgagctacc ggtggcgccg     240
cgatgcagcg gtcgccggtg gagaagcctc cgttcactct gggtcagatc aagaaggcca     300
tcccgccaca ctgcttcgag cgctcggtgc tcaagtcctt ctcgtacgtg gtccacgacc     360
tggtgatcgc cgcggcgctc ctctacttcg cgctggccat cataccggcg ctcccaagcc     420
cgctccgcta cgccgcctgg ccgctgtact ggatcgcgca ggggtgcgtg tgcaccggcg     480
tgtgggtcat cgcgcacgag tgcggccacc acgccttctc ggactactcg ctcctggacg     540
acgtggtcgg cctggtgctg cactcgtcgc tcatggtgcc ctacttctcg tggaagtaca     600
gccaccggcg ccaccactcc aacacggggt ccctggagcg cgacgaggtg ttcgtgccca     660
agaagaagga ggcgctgccg tggtacaccc cgtacgtgta caacaacccg gtcggccggg     720
```

-continued

```
tggtgcacat cgtggtgcag ctcaccctcg ggtggccgct gtacctggcg accaacgcgt      780
cggggcggcc gtaccgcgc ttcgcctgcc acttcgaccc ctacgccccc atctacaacg       840
accgggagcg cgcccagatc ttcgtctcgg acgccggcgt cgtggccgtg gcgttcgggc      900
tgtacaagct ggcggcggcg ttcggggtct ggtggtggt gcgcgtgtac gccgtgccgc       960
tgctgatcgt gaacgcgtgg ctggtgctca tcacctacct gcagcacacc cacccgtcgc     1020
tcccccacta cgactcgagc gagtgggact ggctgcgcgg cgcgctggcc accatggacc     1080
gcgactacgg catcctcaac cgcgtgttcc acaacatcac ggacacgcac gtcgcgcacc     1140
acctcttctc caccatgccg cactaccacc ccatggaggc caccaaggcg atcaggccca     1200
tcctcggcga ctactaccac ttcgacccga ccctgtcgc caaggcgacc tggcgcgagg      1260
ccggggaatg catctacgtc gagcccgagg accgcaaggg cgtcttctgg tacaacaaga     1320
agttctagcc gccgccgctc gcagagctga ggacgctacc gtaggaatgg gagcagaaac     1380
caggaggagg agacggtact cgccccaaag tctccgtcaa cctatctaat cgttagtcgt     1440
cagtcttta gacgggaaga gagatcattt gggcacagag acgaaggctt actgcagtgc     1500
catcgctaga gctgccatca agtacaagta ggcaaattcg tcaacttagt gtgtcccatg     1560
ttgttttct tagtcgtccg ctgctgtagg cttccggcg gcggtcgttt gtgtggttgg      1620
catccgtggc catgcctgtg cgtcgtggc cgcgcttgtc gtgtgcgtct gtcgtcgcgt     1680
tggcgtcgtc tcttcgtgct ccccgtgtgt tgttgtaaaa caagaagatg ttttctggtg     1740
tctttggcgg aataacagat cgtccgaacg aaaaaaaaaa aaaaaaaaa                 1790
```

<210> SEQ ID NO 2
<211> LENGTH: 1733
<212> TYPE: DNA
<213> ORGANISM: Zea mays
<220> FEATURE:
<221> NAME/KEY: CDS
<222> LOCATION: (176)..(1351)

<400> SEQUENCE: 2

```
tcctccctcc tcctccctgc aaatcgccaa atcctcaggc accaccgctc gtttcctgt       60
gcggggaaca ggagagaagg ggagagaccg agagaggggg aggcgcggcg tccgccggat      120
ctgctccgac ccccgacgca gcctgtcacg ccgtcctcac tctcagccag cgaaa atg      178
                                                             Met
                                                              1 ggt gcc ggc ggc agg atg acc gag aag gag cgg gag gag cag gag cag      226
Gly Ala Gly Gly Arg Met Thr Glu Lys Glu Arg Glu Glu Gln Glu Gln
        5                  10                  15 gag cag gtc gcc cgt gct acc ggc ggt ggc gcg gca gtg cag cgg tcg      274
Glu Gln Val Ala Arg Ala Thr Gly Gly Gly Ala Ala Val Gln Arg Ser
 20                  25                  30 ccg gtg gag aag ccg ccg ttc acg ttg ggg cag atc aag aag gcg atc      322
Pro Val Glu Lys Pro Pro Phe Thr Leu Gly Gln Ile Lys Lys Ala Ile
     35                  40                  45 ccg ccg cac tgc ttc gag cgc tcc gtg ctg agg tcc ttc tcg tac gtg      370
Pro Pro His Cys Phe Glu Arg Ser Val Leu Arg Ser Phe Ser Tyr Val
 50                  55                  60                  65 gcc cac gac ctg gcg ctc gcc gcg gcg ctc ctc tac ctc gcg gtg gcc      418
Ala His Asp Leu Ala Leu Ala Ala Ala Leu Leu Tyr Leu Ala Val Ala
             70                  75                  80 gtg ata ccg gcg cta ccc tgc ccg ctc cgc tac gcg gcc tgg ccg ctg      466
Val Ile Pro Ala Leu Pro Cys Pro Leu Arg Tyr Ala Ala Trp Pro Leu
         85                  90                  95
```

```
tac tgg gtg gcc cag ggg tgc gtg tgc acg ggc gtg tgg gtg atc gcg      514
Tyr Trp Val Ala Gln Gly Cys Val Cys Thr Gly Val Trp Val Ile Ala
        100                 105                 110 cac gag tgc ggc cac cac gcc ttc tcc gac cac gcg ctc ctg gac gac      562
His Glu Cys Gly His His Ala Phe Ser Asp His Ala Leu Leu Asp Asp
    115                 120                 125 gcc gtc ggc ctg gcg ctg cac tcg gcg ctg ctg gtg ccc tac ttc tcg      610
Ala Val Gly Leu Ala Leu His Ser Ala Leu Leu Val Pro Tyr Phe Ser
130                 135                 140                 145 tgg aag tac agc cac cgg cgc cac cac tcc aac acg ggg tcc ctg gag      658
Trp Lys Tyr Ser His Arg Arg His His Ser Asn Thr Gly Ser Leu Glu
                150                 155                 160 cgc gac gag gtg ttc gtg ccg agg acc aag gag gcg ctg ccg tgg tac      706
Arg Asp Glu Val Phe Val Pro Arg Thr Lys Glu Ala Leu Pro Trp Tyr
                165                 170                 175 gcc ccg tac gtg cac ggc agc ccc gcg ggc cgg ctg gcg cac gtc gcc      754
Ala Pro Tyr Val His Gly Ser Pro Ala Gly Arg Leu Ala His Val Ala
            180                 185                 190 gtg cag ctc acc ctg ggc tgg ccg ctg tac ctg gcc acc aac gcg tcg      802
Val Gln Leu Thr Leu Gly Trp Pro Leu Tyr Leu Ala Thr Asn Ala Ser
        195                 200                 205 ggg cgc ccg tac ccg cgc ttc gcc tgc cac ttc gac ccc tac ggc ccg      850
Gly Arg Pro Tyr Pro Arg Phe Ala Cys His Phe Asp Pro Tyr Gly Pro
210                 215                 220                 225 atc tac ggc gac cgg gag cgc gcc cag atc ttc gtc tcg gac gcc ggc      898
Ile Tyr Gly Asp Arg Glu Arg Ala Gln Ile Phe Val Ser Asp Ala Gly
                230                 235                 240 gtc gcg gcc gtg gcg ttc ggg ctg tac aag ctg gcg gcg gcg ttc ggg      946
Val Ala Ala Val Ala Phe Gly Leu Tyr Lys Leu Ala Ala Ala Phe Gly
                245                 250                 255 ctc tgg tgg gtg gtg cgc gtg tac gcc gtg ccg ctg ctg atc gtc aac      994
Leu Trp Trp Val Val Arg Val Tyr Ala Val Pro Leu Leu Ile Val Asn
            260                 265                 270 gcg tgg ctg gtg ctc atc acg tac ctg cag cac acc cac ccg gcg ctg     1042
Ala Trp Leu Val Leu Ile Thr Tyr Leu Gln His Thr His Pro Ala Leu
        275                 280                 285 ccc cac tac gac tcg ggc gag tgg gac tgg ctg cgc ggc gcg ctc gcc     1090
Pro His Tyr Asp Ser Gly Glu Trp Asp Trp Leu Arg Gly Ala Leu Ala
290                 295                 300                 305 acc gtc gac cgc gac tac ggc gtc ctc aac cgc gtg ttc cac cac atc     1138
Thr Val Asp Arg Asp Tyr Gly Val Leu Asn Arg Val Phe His His Ile
                310                 315                 320 acg gac acg cac gtc gcg cac cac ctc ttc tcc acc atg ccg cac tac     1186
Thr Asp Thr His Val Ala His His Leu Phe Ser Thr Met Pro His Tyr
                325                 330                 335 cac gcc gtg gag gcc acc agg gcg atc agg ccc gtc ctc ggc gag tac     1234
His Ala Val Glu Ala Thr Arg Ala Ile Arg Pro Val Leu Gly Glu Tyr
            340                 345                 350 tac cag ttc gac ccg acc cct gtc gcc aag gcc acc tgg cgc gag gcc     1282
Tyr Gln Phe Asp Pro Thr Pro Val Ala Lys Ala Thr Trp Arg Glu Ala
        355                 360                 365 agg gag tgc atc tac gtc gag cct gag aac cgc aac cgc aag ggc gtc     1330
Arg Glu Cys Ile Tyr Val Glu Pro Glu Asn Arg Asn Arg Lys Gly Val
370                 375                 380                 385 ttc tgg tac aac agc aag ttc tagccgccgc ttcttttc cctaggaatg          1381
Phe Trp Tyr Asn Ser Lys Phe
                390 ggaggagaaa tcaggatgag aagatggtcc tgtctccatc tacctgtcta atggttagtc   1441 accagtcttt agacaggaag agagcatttg ggcttcagaa aaggaggctt actgcactac   1501
```

```
tgcagtgcca tcgctagatc ctaggcaaat tcagtgtgct cctgtgcccc atggctgtga    1561
gctttgggta ctctcaagta gtcaagttct cttgttttttg tttttagtcg tccgctgttg    1621
taggcttgcc ggcggcggtc gttcgcgtgg ccgcgccttg tcgtgtgcgt ctctcgccac    1681
tctcttcgtg ctccccaaaa aaaaaaaaaa aaaaaaaaaa aaaaaaaaaa aa          1733
```

<210> SEQ ID NO 3
<211> LENGTH: 392
<212> TYPE: PRT
<213> ORGANISM: Zea mays

<400> SEQUENCE: 3

```
Met Gly Ala Gly Gly Arg Met Thr Glu Lys Glu Arg Glu Glu Gln Glu
1               5                   10                  15

Gln Glu Gln Val Ala Arg Ala Thr Gly Gly Ala Ala Val Gln Arg
            20                  25                  30

Ser Pro Val Glu Lys Pro Pro Phe Thr Leu Gly Gln Ile Lys Lys Ala
        35                  40                  45

Ile Pro Pro His Cys Phe Glu Arg Ser Val Leu Arg Ser Phe Ser Tyr
    50                  55                  60

Val Ala His Asp Leu Ala Leu Ala Ala Ala Leu Leu Tyr Leu Ala Val
65                  70                  75                  80

Ala Val Ile Pro Ala Leu Pro Cys Pro Leu Arg Tyr Ala Ala Trp Pro
                85                  90                  95

Leu Tyr Trp Val Ala Gln Gly Cys Val Cys Thr Gly Val Trp Val Ile
            100                 105                 110

Ala His Glu Cys Gly His His Ala Phe Ser Asp His Ala Leu Leu Asp
        115                 120                 125

Asp Ala Val Gly Leu Ala Leu His Ser Ala Leu Leu Val Pro Tyr Phe
    130                 135                 140

Ser Trp Lys Tyr Ser His Arg Arg His Ser Asn Thr Gly Ser Leu
145                 150                 155                 160

Glu Arg Asp Glu Val Phe Val Pro Arg Thr Lys Glu Ala Leu Pro Trp
                165                 170                 175

Tyr Ala Pro Tyr Val His Gly Ser Pro Ala Gly Arg Leu Ala His Val
            180                 185                 190

Ala Val Gln Leu Thr Leu Gly Trp Pro Leu Tyr Leu Ala Thr Asn Ala
        195                 200                 205

Ser Gly Arg Pro Tyr Pro Arg Phe Ala Cys His Phe Asp Pro Tyr Gly
    210                 215                 220

Pro Ile Tyr Gly Asp Arg Glu Arg Ala Gln Ile Phe Val Ser Asp Ala
225                 230                 235                 240

Gly Val Ala Ala Val Ala Phe Gly Leu Tyr Lys Leu Ala Ala Ala Phe
                245                 250                 255

Gly Leu Trp Trp Val Val Arg Val Tyr Ala Val Pro Leu Leu Ile Val
            260                 265                 270

Asn Ala Trp Leu Val Leu Ile Thr Tyr Leu Gln His Thr His Pro Ala
        275                 280                 285

Leu Pro His Tyr Asp Ser Gly Glu Trp Asp Trp Leu Arg Gly Ala Leu
    290                 295                 300

Ala Thr Val Asp Arg Asp Tyr Gly Val Leu Asn Arg Val Phe His His
305                 310                 315                 320

Ile Thr Asp Thr His Val Ala His His Leu Phe Ser Thr Met Pro His
                325                 330                 335
```

```
Tyr His Ala Val Glu Ala Thr Arg Ala Ile Arg Pro Val Leu Gly Glu
            340                 345                 350

Tyr Tyr Gln Phe Asp Pro Thr Pro Val Ala Lys Ala Thr Trp Arg Glu
            355                 360                 365

Ala Arg Glu Cys Ile Tyr Val Glu Pro Glu Asn Arg Asn Arg Lys Gly
        370                 375                 380

Val Phe Trp Tyr Asn Ser Lys Phe
385                 390

<210> SEQ ID NO 4
<211> LENGTH: 12313
<212> TYPE: DNA
<213> ORGANISM: Zea mays

<400> SEQUENCE: 4
ttgtgatgtt gtcaggggggg cggagctatg gaaaaacgcc agcaacgcgg cttttttacgg      60 ttcctggctt ttgctggctt ttgctcacat gttctttcct gcgttatccc ctgattctgt     120
ggataaccgt attaccgcct tgagtgagc tgataccgct cgccgcagcc gaacgaccga      180
gcgcagcgag tcagtgagcg aggaagcgga agagcgccca atacgcaaac cgcctctccc     240
cgcgcgttgg ccgattcatt aatgcagctg gcacgacagg tttcccgact ggaaagcggg     300
cagtgagcgc aacgcaatta atgtgagtta gctcactcat taggcacccc aggctttaca     360
ctttatgctt ccggctcgta tgttgtgtgg aattgtgagc ggataacaat ttcacacagg     420
aaacagctat gaccatgatt acgccaagct atttaggtga cactatagaa tactcaagct     480
atgcatcaag cttggtaccg agctcggatc cccttgcagc agagagcaag ttccaacaat     540 accccccaacc acccaccatt cattgcatcc aagttttcta acttcccaca acttacaaga    600
gctatagcat tcaatacaag acacaccaaa gagatcaaat cctctcccaa gtccatagat     660
catttccaat caaataatga ctagtgagag ggtgacttgt gttcatttga gctcttgcgc     720
ttggattgct tcttttttctc attctttctt gtgatcaact caattgtaac cgagacaaga    780
gacaccaatt gtgtggtggt ccttgcgggg actttgtgtc tcgtttgatt gagaagagaa     840
gctcactcgg tctaagtgat cgtttgagag agggaaaggg ttgaaagaga cccggtcttt     900
gtgaccacct caacggggga gtaggtttgc aagaaccgaa cctcggtaaa acaaatatt      960 tgcttacaat ttgtttttcg ccctctctct cggactcgtt aatatttcta acgctaaccc    1020
ggcttgtagt tgtgcttaag tttataaatt tcagattcgc cctattcacc ccctctagg     1080 cgactttcag taccgttata tatgctttcg atttatcctg ccctaagtc agttactaga     1140 aagattgata ttcttaggag gcgtcttctt tggcaagggg gtcgtcagtc caaaaaaatt    1200
catttagttg attggttgtc ggtgtgctct cccaaaaagt cagggaggtc tgggtgttct    1260
gaatctcgat tttatgaatg attccttaat gactaaatgg ctttggaata ttgaaacttc    1320
gaatggctta tggcaaaaaa ttattaccag taaatatatt aagggaaaac cccttatttt    1380
gatcaagcaa agacaaggtg attcacactt ctggaaaaaa aattctgagt ctgcgtgata    1440 attttttacaa attttgcaaa tctggggtgg gaaacggttt gaagactagc ttttggaaga   1500
gtatctggat tggaaatctg cccctgtctg ttcagtttcc tgttctattt gacttgtctt    1560
atgacaaaga cattacggtt aatgatgtca tggcttctaa ttttgaggtt cttacattta    1620
gaagaaggat tgttggtaat ctgagggttc taatggatga gttggtgagt tgttgcaatc    1680
atgtgttctt gtctgatcag gaggacagaa ttgtgtggag tctggggaga aaaggctttt    1740 ctattaatttt tatttaaaaa agaaaatggc agatcaagtt ttgatttcat ataagttctt    1800
```

```
gtggaaaatc aagattttca tgtggttggt tgtgagaaat aaaattctta ctaaagacaa    1860
tatgaagaaa aggaactgga atggttcttt ggaatgttgt ttctgtggcg tggatgaatc    1920
cattgatcat ttattctttc attgtcccat tgcgagatat atgtggagag tgattcaagt    1980
ggccttgaat ctgaggatga ttccaagtag tattagcaac ctttatgaca accggttatg    2040
tagaccaaaa gataatattg ctaatctggt tttgtttggc tgtggagcta tgttctgggc    2100
aatttggcgc actagaaatg attggtgctt tgggaataaa actatgcttg atccctctaa    2160
catcattttt ctttgctgct tctggctgga ttcctaggct attcgacaga gaaagaagga    2220
gcaaaaaata gtggtccaag gaagcaagct aatctgaaag acaacaagtg aagcattcag    2280
ccgagcgttt gggtggtgcc cgatagacag gcgtatttct ggttgatctt aagctggaac    2340
ttgaatgatg gtgctggtgc tatcctttct tttggtggtt gtcttggttc agtatctttt    2400
gttgcaccag tctgtcatga tatgattgta aataagaaag gcttatgttg ttaatcgtaa    2460
gtcaaacttt attcgctatc ataggtcctc cactgatcta gtttgatagt gttaggagtc    2520
tagatagaga tctgaccttg ttcgattttt ttggtttatt ggtcgcatga gtactgttgt    2580
ttcaaacttt catatttctt aatgaaatag gggcttcgcc cctacaactc tgatcacttt    2640
cacttgcata cgggagacct ctccaattca tactgtgtgt tgggggggggg ggtgggggggg   2700
acaagaataa cgagagaaaa aaatctgagc tttaccatta cagaggtcag aggttacgaa    2760
cagctgcatc caccgtcaaa atgcgccagt gcacccacgt cctgttggat taatgtgggc    2820
ttggcccaaa ttaatattca ataatagtca atgctaatgg cccactttaa tgctatggtg    2880
tactaattat ttagtaccat attggaagtt caaaggacaa atcaatcaac ttaaataggt    2940
ggaccattgg tgcatctatt gagaagttga gaaaagaatg aaagactgcc acacgcgcgc    3000
gcgcgccgcc gccgccggcc gggcccgtgg ccgtggccgt ggccgtggct cgtggctcgt    3060
ggtagatcgg accttggtcc gaatattcct ttcaaacggt tgtgcatttt gcctggattg    3120
atgaccgtca taataaccgt ctgtttcctg tcttatggct agtaacggac gtcagttact    3180
gtcgtcagtt tccagttcta atgcgcgacc gtttctgtcc gttgctcttc tcccttcttc    3240
tgaccggcta taagaatgga gagggagagc tcttccagtc aggcgaattt atctcacgcg    3300
aattgcaaac aacacattcc ccgtcccatc ttctgcgagc acagagagag tgggagagca    3360
ggcctccgaa atcaccgacc gcagagatac acttgcacgg gtgtgcgggc gatcagattt    3420
ttggggagcg tcttcgcgac tgctcgcgtg atcgtccaca gcttgctgtt cgtcgcctac    3480
ccaagttgac gcgtgctgct gttcttcttc ccggcgaccg ttcgagggac tgcactgcgt    3540
acaccttcct gcaccgactt cgtacgacta catcgaacaa acacacgaga tgtctcgtgt    3600
gaatggagcc actggtgcct tgagcatcgg tccctccgct gggtacactc tgttcttcgt    3660
atttgtgcat gtttcattgc tgtttactgc ttatgcgagt agttatacac acatgcacat    3720
acatgtcatc acatatatca cactgatttt ctggattaaa ttaaaactaa aaatgcctaa    3780
cttctaaca cgtccgagca tcaccgcttg cttgcgccct cggcggtctg aatctgcat    3840
gtcgccgggc gcggggcgcc ggcgcaccgc ccccgccgtg gtctgctacc cgtcagtccg    3900
cgccacactt cttgaggaga acatcgtcgc acgcgggcac gcggcgtggc cggcggtgac    3960
aactgcagag catggtcgcc acttgtcagt tctgtcagca agggtgccgg tgccagtgcc    4020
agcaccgagc tcgctttgtt tgcctgctgc cagtgtggca gacatcggac gacggagctg    4080
taggcgccat gcgcatacta gatgggtatc tttcggtgct tggaacttgg ttcacaggtg    4140
gatgtctgca tgcacatcgt ctctacagtc tacactgaat caagcacacc attacaccaa    4200
```

```
tgcattttc  tgttgcctgt  atggagatag  ctgattagtt  caccgaatga  agcacaccaa   4260
cgtgcgtact  tttccaacca  gttgcgcttg  agatagctg   ctggttagtt  caccgaatcc   4320
gcggcctaac  tccggacaca  ttttttttctt ctggtagatc  gcatcacatg  cttgctcccc   4380
atcacgggct  gcaaggtgcc  acccctcgct  gcctgttcca  ggccatcaac  accgtgggtt   4440
tggcaaccgg  tgttgcgcta  cccaatgcct  gagaaaaatc  gtggtacggc  ccaaccatgg   4500
aagatcagcc  aaaatgagct  cacatgaaac  tgcccaaaac  aggaagaggg  tagttgaaat   4560
aaaatgggtt  cagtgacggt  acgaagtcag  atttgaagaa  gtgcccaacg  ataatacata   4620
gttcaactac  attcgtatta  ttttttggaca aatcttcagg  tcccaaatta  tttagttcac   4680
cgctgcaaac  tactatatgg  aaagatacga  cgatcaatca  aaaggcaatt  ttctttggtg   4740
aaccaatcgt  ttcacaaggg  aaatcaacta  cgccgatgtc  tgctgttttc  cttagggcct   4800
gttcgcttct  tcaggaatga  acttggattc  attcgagctc  atcaaaattt  atataaatta   4860
gaaaagtaat  ccggctaaga  actattccag  ggctccaatc  cgtgaaaacc  gaacagagcc   4920
ttagagagcc  cgtctgttgg  ataggagtat  atagcttttt  gtttaagctt  ttttttcaat   4980
ttctgatcac  cagaagatgt  cgcaaaactg  ttaaacatct  aacttttttaa cctgtttcta   5040 taagaatcat  tttagtcaaa  attatctaaa  atcaatatga  ggacagaatc  aaccgagtcc   5100
ttatgaaaac  cgtcattttc  tatatcctaa  atcatataaa  ctattttatc  tttcttcaca   5160
ctttatctac  atgaaactgt  attccctaca  accatatttt  tctggcagtc  agattctaaa   5220
aaaaatcctc  acaaaaaagt  tgaaccaaac  tcgcgagcca  cgggcccgcg  tccggcgctg   5280
cacgagctgt  gtcacgcctc  ccggcctccc  ggggtccagc  caaatagggc  tctacatgtg   5340
cacagggcca  gatttcacgt  ccgccgacgt  ggttacggcg  tcacatgatc  acatctggct   5400
cctccgggcc  caggcgccag  tgacgccgtg  cccgcctcta  aatagcgcct  ctctcccggg   5460 ctgccgcgg   aaccgaggcg  gtcaggctcc  ctcctccttc  ctcctccctg  caaatcctgc   5520
aggcaccacc  gctcgttttc  ctgtccgggg  acaggagag   aaggggagag  accgagagag   5580
ggtgaggcgc  ggcgtccgcc  cgatctgctc  cgccccccga  agcagcctgt  cacgtcgtcc   5640
tcactctcag  gtacccgcat  ttagccttcc  tggattgtta  tggatcacta  gtgccccccc   5700
tgccactgtt  ccatagattg  ttccgaatgg  attggtgagg  aatcgaccgg  cgttcggttc   5760
tgggttgctg  agcccggcaa  cgggctcgtg  gccggccgtc  gattcggcag  cggcactcgc   5820
cgtcgcgccg  cccggtcggg  tcgggtcggg  tctctgcaaa  ctcgccgtag  cgcctgccgg   5880
tcgagctttg  acaccgacct  caccggcggg  catccgcggc  cctgccgatg  tggatttcag   5940
gttttgcccc  gatgaatcca  cgcttgttcc  tcaccagatc  tgtaggtatg  attcagcgag   6000
tggtgccatt  cagatatttt  gcccgtgcaa  tgggaccgtg  attgatctcc  gcacctcctg   6060
ccgtgaccac  tcgttttggg  aacatggcat  gccacctttta gccacgccca  cgagctgacg   6120
agctcttcgc  agctcccgta  taaaaagctg  caaccttttgc aggtctttga  ctccaaaggc   6180
ggcctctttg  tttcggcgct  cgccccctc   catgttgggc  atgatgcgtt  gcacttggtg   6240
cccgactcct  ctgttttcta  gctcctaatt  tttttttgctg atgctactat  agtactatta   6300
gctaagcgcg  gagttggcga  tgactgcgct  caagaatcga  cctttggctc  gggcaatcga   6360
tgcatggacg  aagccacttg  ttttttttttt ctttggtcat  gttttttgaca tgcgaaactg   6420 cgaaggtggc  agagtaggtg  gatctttctg  tctatgtttt  ggccctactt  gagaggaaga   6480
gacagtcgcc  accgtgcaaa  gtcccaaagg  catccgacgg  tggcgcgtcg  atcgttacga   6540
tgccagacaa  gcaccacgga  acgagccacc  tcccccgcgg  ccagcccgcc  atcgagcagg   6600
```

```
tcacgactga gattgaaaga aacgcgatct aattttttgtc ttttcttttc ctgtcccaag   6660
ttccttaata cttgatacgt gagctctata acactagagg ttttccattc ggaaaaatat   6720
gttcgctaaa gtcggtctct gattaaagtc ggctgcttga cggctgcaac tgtaatttat   6780
gtaatttatt aaaacaaaaa cactgtgttg acacctttt ggaggcgcca atcacttcaa    6840
aagaaccggc ggcggtgctc tctggtcagg cgcggacggt ccgcggcaca gggccggacg   6900
gtccgcgacc tggcgtgagg cggcggtgct ctctggtcag gcgcggacgg tccgcggcac   6960
agggccggac ggtccgcgac ctggagcagg agctcgggtt ccctgcctga cggtcggacg   7020
gtccgcgcgt gcgcagggc ggcggaagat cgccggcggc gcctggatct cgctcccggg    7080
agggaccccg tcggggagga gagatcctag gagttgtcta ggctcgggcc ggccgaccta   7140
gactcctcta atcgacgtag agtcgaggag aggcggagaa tttggggatt ggaatactaa   7200
actagggcta aactagaact agactagaac tactcctaat tgtgctgaaa ataaatgcga   7260
gatagaagtg gtattggttc gattgttggg ggttcaatcg gccgtatccc ttcatctata   7320 taaagggga ggtctggatc cgcttccaac tgatttccga gttaatcccg cggttttagg    7380
taacaaatcc cgcgagaaac taggaaccct aactgactct gcgcacgcgc ggaccgtccg   7440
cgccaccacc gcggacggtc cggaccgcgg accgtccggc ctccgggccg gaccgtccgc   7500
acggtcattt tggggttccaa catatgcccc ctgccttttg gtgaaggtcg acaaaccaaa  7560
agcattgaac taaacctgat gtaagtcacc ggcttttcga tatggagatt attcaataaa   7620
gcaccaatat aaaggccgtt tcggattgta tctttctcgg ccatgaccat ttgatcaatg   7680
gatcaaaagg aatagaatgg aggtgccccc cagtctggat agacgaaggg actatacatg   7740
taccatggat tcatcatcgt gccattccat gtttgaacag gataatatac cgacgatgag   7800
taaataggtg gaaagtaccc tggtctcata gaatgaatag gcgatgcttg ttgtgtcgcc   7860
tttcgggccg tctttgttta accgttttgt tttagcaggt ggctgggtt tctttgttga    7920 ccgatcacgt ggaacagtct ttttgctagc attttttggag agcaactgat caaaagtagg   7980
atcggctttg atcagccgat tatatgtgct ttgaccttgc gccttttcc ttgctttgtg    8040 tagaggttga cgcctttggt cataggggga ctgtccggct gagttagccg gaccgtttgt   8100
ctgagcaccg gatcgtccgc acgtaggtgc cggaccatct acgatgttcg ggctaggctg   8160
atgtgtttgg ttcattaact gtgcctgccc cccagtgtct tcggacttt tagccttctc    8220 gtccgaagcc tttcgagcaa tctcttttttg tgatatatct gacatgcggg gatcgccaat   8280
gacgataccc ttgcctttgc ctttatcggc catttcgggc cgaaccaaga ccttttttgca  8340 tgtgagttct attgtattaa caggaaaggg ttgtgtgtct acttgcatct cctgaaaagc   8400
caatcgacac tcatttatgg ccgattgtat ctgtcgacga aaaacattac aatcattggt   8460
ggcatgagaa aaggaattat gccacttaca ataagcacgc ctctttaatt catcaggagg   8520
aggaatagta tgagttaatt taatgttgcc gttttttcagt aactcgtcaa atattttatc   8580
gcatttggca acattaaacg taaacttaac ttcttcttgt cgattctttc gaatcgactg   8640
taaagcagaa cacggtgaag gtttagcctg ccctggccaa accagttcag cggtgtatac   8700
atccgtggat tcatcgtccg agttatcata tcccactaga tgcatcttat ggctagccga   8760
ttttgatgtt tccttacttc ggctttcaca tgtcatagcc cgctggtgca agtgcactag   8820
cgaaaagaat tgggtaccat ctaatttttc ttttaagtag ggtcgcaacc cattgaaagc   8880
tagccctgtt agttgttttt ccgcgacatg aatctgaaag catcggtttc tagtgtcccg   8940
gaatctccgg atatagtcat taaccgattc ttcaggcccc tgtcggactg aggctaagtc   9000
```

-continued

```
agccaattct aattcatgtt ctcctgagaa gaagtgttca tgaaatttct gctctaattc      9060
ttcccaagag ttaatagagt ttggtggcaa agttgcgtac catgcaaatg cagtatcagt      9120
aagggacaac gaaaataaac gaacgcggta ggcttcccca tcagccaatt ctcctaagtg      9180
tgctatgaat tggctaatat gttcgtgtgt gcttttccca ccttcaccag aaaacttaga      9240
gaagtctggt attctagttc cctgtggata tggcacggtg tcgaatcggt ggctataagg      9300
cttccgatac gattgccctg tacctgacaa actaacaccg agtttgtccc tgaacatccc      9360
ggctacctcg tctctgatcc tctccgccat atctggcgac catctattga gtttgtgggt      9420
ggaaacctca ggttgcctga catcactctg tcggctttcc tcccagggat gtttgaggtg      9480
tgcgctaggt gtcctattaa tgtcaccaac tcctgcccta tacctctcag gctctcttgt      9540
ggccgaacag tattcagccc tatgtccatg aggtggtatg gcatgattat aatgtgttac      9600
tggtggggca ccataatgtt gctgcgatga atgcggaaac tgtgcgtatt gcgcagctct      9660
cggctctgcg tatgcatatc cggacggtcc ggcataagag gccggatggt ccgcgacctg      9720
gccaaatggt tcgaaggtat atccggattg tccagccgta tatggtgcta catgggtagt      9780
ctcgtaccca gaccgtctgt cgtagataac tggacggtcc gcgatcgggc cgaatggtcc      9840
agggctgtac ccggacggat cggtcatata tggcgcgact tgggtagtct gcgcgtggac      9900
tcgtgtagag tcggatggtc cagcgtaata cgtcggccgg ttcatgccat atccggacgg      9960
tccggcgtaa gatggcgaac ggttcgcaac atatccggac ggtccggcgt gatgcaccgg     10020
acggtccgtg atgggccgaa gtgttcaggg ttgtaccct gatggtccgg ccatgtacgg     10080
tgcgacctga gtgttttgcg tgcgggcctg catctggtcg gacggcccgg cgaaatacgc     10140
cggacggtcc gcggtataac cggactgtct gagatgatgc tcggacggtc cggtcgcgtc     10200
cagtacctgc cgtgtgccta gtggttgcgg ctgtgatggt gacacgaaag cgtgcatcgg     10260
cataccatat gatggctggg tcaagggtga cccgtttata gccgatgtgt ttgacgtggg     10320
tggcactgta ttagactctc gtgatggaaa gttaggagca gctgatttct cgtatgcacg     10380
taaatgcatt ttaatagatt catctacata ttgctttaat tgatctcctc gttgatccat     10440
gaaagtcgta agagataggt ctggagtact tacagcggga ccctgaagtg gaggtaggag     10500
agattccata tcgatctccc cttgacggac gatcttctgg tggcgatcta ccgtgaagtg     10560
tgacaagtac ttgtctgccg cctccttgcg cctttcggag agtttatgca gtagttccgc     10620
ctcttccttg tcgtgttgtt cgttccattg ccgcatcacc tccttctcat cgcgcattac     10680
gaggtcttca aagggccttt ggtcatcagc cgggagcgcc tccatggccg gcttgatgat     10740
gttggtagtg gagatcttgg tgtgatcctt agaaccggcc atttatgggc cgatttttgc     10800
agattagaca cctagtcccc agcggagtcg ccaaaaagta cgttgacacc ttttggagg      10860 tgcaatcact tcaaaagaac cggcggcggt gctctctggt caggcgcgga cggtccgcgg     10920 cacagggcc gacggtccgc gacctggcgt gaggtggcgg tgctctctgg tcaggcgcgcg     10980 acggtccgcg gcacagggcc ggacggtccg cgacctggcg tgaggtggcg gtgctctctg     11040
gtcaggcgcg gacggtccgc ggcacagggc cggacggtcc gcgacctgga gcaggagctc     11100 ggttccctg cctgacggtc ggacggtccg cgcgtgcgca ggggcggcgg aagatcgcca     11160
gcggcgcctg gatctcgctc ccgggaggga ccccgtcggg gaggagagat cctaggagtt     11220
gtttaggctc gggccggccg acctagactc ctttaatcga cgtagagtcg aggagaggcg     11280
gagaatttgg ggattggaat actaaactag ggctaaacta gaactagact agaactactc     11340
ctaattgtgc tgaaaataaa tgcgagatag aagtggtatt ggttcgattg ttgggggttc     11400
```

| | |
|---|---|
| aatcggccgt atcccttcat ctatataaag gggaggtctg gatctgcttc caactgattt | 11460 |
| ccgagttaat ccagcggttt taggtaacaa atcccgcgag aaactaggaa ccctaactga | 11520 |
| ctctgcgcac gcgcggaccg tccgcgccac caccgcggac ggtccggacc gcggaccgcc | 11580 |
| gcacggtcat tttgggttcc aacacacggt ataaacatta gaaattggta cggattaagg | 11640 |
| ctaagcgaac agcctagaga ctgtgagcgc tcgaatccca ccttgtggga gcaccggagc | 11700 |
| acatgtgcag cttcgagcca tactggacgc tgcactgaaa gttttggcat tcatatagta | 11760 |
| aacgtccgtg gtcgacaggc acccacggcc ttgaacatag cgatggaagt catggatcga | 11820 |
| cgaagctgat tgagtcagtt acaccgaagt cgattgacaa aggctatcta ccacgacatc | 11880 |
| aaatcgcaca ggaagacgtg atgaatagca ggtagagaga gagggtaaaa gatgtagcag | 11940 |
| attggttttt tgatgattga aagagtcgac cgtgttcatc tgatatacgt agaggtggtg | 12000 |
| gtcttatctg agcttccaca tgctgcgatc gatttgttgg tccccatctt gctctcccac | 12060 |
| acaggaatac tattaaccat gttcaggcaa gaaagtgatg cggtcgtgca cggcacatgc | 12120 |
| cagctttgtg ggagccgccc ctaaccctcg ctgaatcagt cagtagtgcc aacttgctag | 12180 |
| agttttttt cttcttgttt tggttcactc gacagatttt tgtttggatg agatcgctgc | 12240 |
| aacattgttc ttgatccaca cttgcctgat cttaccgtct cgttcgtgtt cgtgccagca | 12300 |
| accagcgaaa atg | 12313 |

<210> SEQ ID NO 5
<211> LENGTH: 2907
<212> TYPE: DNA
<213> ORGANISM: Zea mays

<400> SEQUENCE: 5

| | |
|---|---|
| caggtacccg cattagcctt cctctattct ggatgatccc ccctgccagt gtttcataga | 60 |
| ttgttctgaa tggattgatg aggaatcgac cggagtttcg gttttgggtt gctgagctcg | 120 |
| gcagcagggt gacagttcgc cgtagcgggc tcgtgaccgg ccgtcgccgg cggggcgggt | 180 |
| ccggccgagc tcgtgtcgtc gatccgtagc gttgggtctg ggagaaagta atgggatgcg | 240 |
| gccgaactcg ccgtaccccc cgccggtcga gcttgacatc gatctcaccg gcgggcatcc | 300 |
| gcacaagcct tgcgctgccg atgtggattt gcccagatta atcctggcaa agcgcgcttg | 360 |
| tttcccatct catcagatct gtaggattca gcgtggggtg ccgatcagat attttgcccg | 420 |
| tgcaatggat ccatgatctc tgcccccctcc tgcccactcg tttcgggaac atgacatgcc | 480 |
| acttttggcc acgaactttt cgcagctccc gtcaatcttg tgggtaaaag ctgcaacctt | 540 |
| tacaggccta gcctctttct ttatgcgttc ggtccctcca tgacagccat cgctgcgcct | 600 |
| gcgccctccc catgatggcc aactgctccg ttgttctatc ttctgatttt tttactggta | 660 |
| ctattagcta agcacggagt tggcgacaat tgcacccaag aattgactga ccttttagct | 720 |
| ccagcaattg ctgtgtctag gaagcaactc gttctgcttt ggtcacacat aaaaaatatc | 780 |
| tacttgtcca gatgggaaac cgtatatgct tttctaggaa tttggataga aaaaaataga | 840 |
| gcgcgttcct ttcaatccca gtcatcacac gctcgaggts gagggcagga aaccgccggc | 900 |
| ggcggcggcg gcagcgggga tgggagctc gttccgtggg tcttgtctgc ttgacctaga | 960 |
| aaacggcatc gtgatgaasg acgcgctacc gtccgatgcc ttgggatttt ggacggtggc | 1020 |
| gactgtctcc tcccasgtgg ccacgtacag tcaaaaaccg agacagaaaa agatttcacc | 1080 |
| tactccgcct caccttcggc atgggccggc ggcatgtcag ggctctgcag ctgtgtctgc | 1140 |
| gcaacggtac aagacgccgc ggggggtcgca gcctgcaagg ccggcaccga attctaggcc | 1200 |

-continued

```
ccacatgatg gcatgcaaca ccggtgcaca gatattttc gacacgatta tccagccgta      1260
gaataactcg gacaagtgtc gagaggcgtg gactagcaga tctgggtgca gttggcccct      1320
ctggtgacca gagtgacccg tccttcacct tggcgtggtc ggctgcaact cgctgtccga      1380
tgcaaattgc tgctactgct atgtccatgg catggagtcg catgtgccat tcttccctg       1440 tttgtttggc tctccccgcc gtccgatcag aaagttaggg agacaattta ggccctgttc      1500
ctatctcgcg agataaactt tagcagcttt tttttagcta cttttagcca tttgtaatct      1560
aaacaggaga gctaatggtg gaaattgaaa ctaaacttta gcacttcaat tcatatagct      1620
aaagtttagc aggaagttaa agtttatccc gtgagattga aacgggcctt tagacgggcg      1680
gcccttgtct tgtcagaatt aatgcacagt atcggcacgg cggccaagca tctctttcga      1740
cggatctggt ttctgtctcc atctgtgggc gccatggttg gctggtcgac aggacgcgct      1800
tgtgtcattt gggccaagcc ccaagggaga cagataacat ccgattccac ctcgtgcgag      1860
cacatgtgcg gcttcgagcc ataccatacc atactgaatg ccgcacttcc aaagttttgg      1920
catcactgat aaacgcccaa attttggtaa caagatgaag caaacagaca atgaaaaacc      1980
ggatcttttc taagatttat actaatgcgc cgtgcatctt ttacgttgct atatggtgct      2040
tcactaggct ttatcgtaaa ccgaactgat ttaccaccac cttcaatgca caaggcagag      2100
cacctgccat cttacgctga ttttttttg aaatatggtg tgcctctagg ctctggactg       2160
gtaggtgggt ttgcatgtag aaaagatgac ttgggagctc atgcttgcta gcttgtcaaa      2220
attgaccact tctaccgatg acgcaagatt gccttgctct gtatggctat tggatagctt      2280
agatttgacc atatatggta gtactaccat ttatttttcc ttccgctgaa tcacctcaac      2340
gcacgttctt ggcgctgccg cttgttagtc tctcctgcct gctgctttcc attggtccag      2400
aagtcccttt cacaaatcac cgtccaattg catgcagtac atcacatgtt tctcaagggg      2460
gttgttggac cagttcgttc aatgtaacat cacaagcgac aggaccttaa tctgttttct      2520
gcttatttaa tgtagatttg ccgtagggtt ttgtaccatc cttggtcttg ctgtaaagtc      2580
tgcattttat tagttctgtg tggtggtaat cagaattgct ggtttgggct cgcacatgct      2640
gtgatcccca acttgctgtg gcgtggtagt tggatcgtgt ttaggcaaga aagtaaatgc      2700
gatcatgcac ggcatatttg ccaccttcct gggagacgcc ccctcgtgcc gtgatctgtt      2760
ttactttggt tgattggtgg cctttctcgt ggttcacgtg acagcttttc tgatgggatg      2820
agatcactgt aatgttgttg cttgattcac gctcgcttga tcttactgta gcgtacttcc      2880
tcgtttgtgt cagtcaggag caagatg                                         2907
```

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 6
gayatgatha cngargar                                                     18

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

```
<400> SEQUENCE: 7
ccrtcrtaca tnagatg                                                    17

<210> SEQ ID NO 8
<211> LENGTH: 1714
<212> TYPE: DNA
<213> ORGANISM: Zea mays
<220> FEATURE:
<221> NAME/KEY: CDS
<222> LOCATION: (134)..(1312)

<400> SEQUENCE: 8
ggcacgagct cactgccatt tgtttggttg ttcctctcgc tcgccagtcg ccaccaggca     60
gcaggcatcc caatctcgcg agagccagta gcggcggcgg cgcttccggc ttcccttccc    120
attggcctcc ggg atg gcg ctc cgc ctc cac gac gtc gcg ctc tgc ctc      169
            Met Ala Leu Arg Leu His Asp Val Ala Leu Cys Leu
              1               5                  10 tcc ccg ccg ctc gcc gcc cgc cgc agc ggc ggc agt ttc gtc gcc          217
Ser Pro Pro Leu Ala Ala Arg Arg Ser Gly Gly Ser Phe Val Ala
             15                  20                  25 gtc gcc tcc atg acg tcc gcc gcc gtc tcc acc agg gtg gag aac aag      265
Val Ala Ser Met Thr Ser Ala Ala Val Ser Thr Arg Val Glu Asn Lys
 30                  35                  40 aag cca ttt gct cct ccg agg gag gta cat gtc cag gtt aca cat tca      313
Lys Pro Phe Ala Pro Pro Arg Glu Val His Val Gln Val Thr His Ser
 45                  50                  55                  60 atg cca tct cac aag att gaa att ttc aag tca ctt gat gat tgg gct      361
Met Pro Ser His Lys Ile Glu Ile Phe Lys Ser Leu Asp Asp Trp Ala
                 65                  70                  75 aga gat aat atc ttg aca cat ctc aag cca gtc gag aag tgt tgg cag      409
Arg Asp Asn Ile Leu Thr His Leu Lys Pro Val Glu Lys Cys Trp Gln
             80                  85                  90 cca cag gat ttc ctc cct gac cca gca tct gaa gga ttt cat gat gaa      457
Pro Gln Asp Phe Leu Pro Asp Pro Ala Ser Glu Gly Phe His Asp Glu
         95                  100                 105 gtt aag gag ctc aga gaa cgt gcc aag gag atc cct gat gat tat ttt      505
Val Lys Glu Leu Arg Glu Arg Ala Lys Glu Ile Pro Asp Asp Tyr Phe
    110                 115                 120 gtt tgt ttg gtt gga gac atg att act gag gaa gct cta cca aca tac      553
Val Cys Leu Val Gly Asp Met Ile Thr Glu Glu Ala Leu Pro Thr Tyr
125                 130                 135                 140 cag act atg ctt aac acc ctc gac ggt gtc aga gat gag aca ggt gca      601
Gln Thr Met Leu Asn Thr Leu Asp Gly Val Arg Asp Glu Thr Gly Ala
                145                 150                 155 agc ccc act gct tgg gct gtt tgg acg agg gca tgg act gct gag gag      649
Ser Pro Thr Ala Trp Ala Val Trp Thr Arg Ala Trp Thr Ala Glu Glu
            160                 165                 170 aac agg cat ggt gat ctt ctc aac aag tac atg tac ctc act ggg agg      697
Asn Arg His Gly Asp Leu Leu Asn Lys Tyr Met Tyr Leu Thr Gly Arg
        175                 180                 185 gta gat atc agg caa att gag aag aca att cag tat ctt att ggc tct      745
Val Asp Ile Arg Gln Ile Glu Lys Thr Ile Gln Tyr Leu Ile Gly Ser
    190                 195                 200 gga atg gat cct agg act gag aat aat cct tat ctt ggt ttc gtc tac      793
Gly Met Asp Pro Arg Thr Glu Asn Asn Pro Tyr Leu Gly Phe Val Tyr
205                 210                 215                 220 acc tcc ttc caa gag cgg gcg acc ttc atc tcg cat ggg aac act gct      841
Thr Ser Phe Gln Glu Arg Ala Thr Phe Ile Ser His Gly Asn Thr Ala
                225                 230                 235
```

-continued

```
cgt cat gcc aag gac ttt ggc gac tta aag ctc gca caa atc tgt ggc         889
Arg His Ala Lys Asp Phe Gly Asp Leu Lys Leu Ala Gln Ile Cys Gly
        240                 245                 250 atc atc gcc tca gat gag aag cga cat gaa act gcg tac acc aag atc         937
Ile Ile Ala Ser Asp Glu Lys Arg His Glu Thr Ala Tyr Thr Lys Ile
                255                 260                 265 gtg gag aag ttg ttt gag atc gac cct gat ggt aca gtg gtt gct ctg         985
Val Glu Lys Leu Phe Glu Ile Asp Pro Asp Gly Thr Val Val Ala Leu
    270                 275                 280 gct gac atg atg aag aag aag atc tca atg cct gcc cac ctg atg ttt        1033
Ala Asp Met Met Lys Lys Lys Ile Ser Met Pro Ala His Leu Met Phe
285                 290                 295                 300 gac ggt cag gac gac aag ctg ttt gag cac ttc tcc atg gtc gcg cag        1081
Asp Gly Gln Asp Asp Lys Leu Phe Glu His Phe Ser Met Val Ala Gln
                305                 310                 315 agg ctt ggc gtt tac acc gcc agg gac tac gcc gac att ctt gag ttc        1129
Arg Leu Gly Val Tyr Thr Ala Arg Asp Tyr Ala Asp Ile Leu Glu Phe
            320                 325                 330 ctt gtt gac agg tgg aag gtg gcg gac ctg act ggt ctg tcg ggt gag        1177
Leu Val Asp Arg Trp Lys Val Ala Asp Leu Thr Gly Leu Ser Gly Glu
        335                 340                 345 ggg aac aag gcg cag gac tac ctc tgc acc ctt gct tca agg atc cgg        1225
Gly Asn Lys Ala Gln Asp Tyr Leu Cys Thr Leu Ala Ser Arg Ile Arg
    350                 355                 360 agg cta gac gag agg gcc cag agc aga gcc aag aaa gca ggc acg ctg        1273
Arg Leu Asp Glu Arg Ala Gln Ser Arg Ala Lys Lys Ala Gly Thr Leu
365                 370                 375                 380 cct ttc agc tgg gta tat ggt agg gaa gtc caa ctg tga aatcggaaac         1322
Pro Phe Ser Trp Val Tyr Gly Arg Glu Val Gln Leu
                385                 390 ccattgcgac tgcttgagtt ggagcatagt ctatcatgca ccctatgacg catcgcacga     1382
caagacctgg tgtgtcgcgt gacatagttg ttcaggtttt gaccaaatgg tctgggagca     1442
tttgttttgc cttgtgccgt ctcatagagc gttaggatag tgtacgtctg tgttctagct     1502
ttgttttgtc tgctgctttg atgtaacttg tggccatgag gctggacatg gagtgaacat     1562
gttgtacatt gtcgctggcg gtatgtttcg gtatgttatt tcagttgctt gagatctgtt     1622
aattttttgc gcagctatgg aggtcgttct gttctggtca aaaaaaaaaa aaaaaaaaa      1682 aaaaaaaaa aaaaaaaaa aaaaaaaaa aa                                      1714
```

<210> SEQ ID NO 9
<211> LENGTH: 392
<212> TYPE: PRT
<213> ORGANISM: Zea mays

<400> SEQUENCE: 9

```
Met Ala Leu Arg Leu His Asp Val Ala Leu Cys Leu Ser Pro Pro Leu
1               5                   10                  15

Ala Ala Arg Arg Arg Ser Gly Gly Ser Phe Val Ala Val Ala Ser Met
            20                  25                  30

Thr Ser Ala Ala Val Ser Thr Arg Val Glu Asn Lys Lys Pro Phe Ala
        35                  40                  45

Pro Pro Arg Glu Val His Val Gln Val Thr His Ser Met Pro Ser His
    50                  55                  60

Lys Ile Glu Ile Phe Lys Ser Leu Asp Asp Trp Ala Arg Asp Asn Ile
65                  70                  75                  80

Leu Thr His Leu Lys Pro Val Glu Lys Cys Trp Gln Pro Gln Asp Phe
                85                  90                  95
```

```
Leu Pro Asp Pro Ala Ser Glu Gly Phe His Asp Glu Val Lys Glu Leu
            100                 105                 110
Arg Glu Arg Ala Lys Glu Ile Pro Asp Asp Tyr Phe Val Cys Leu Val
        115                 120                 125
Gly Asp Met Ile Thr Glu Ala Leu Pro Thr Tyr Gln Thr Met Leu
    130                 135                 140
Asn Thr Leu Asp Gly Val Arg Asp Glu Thr Gly Ala Ser Pro Thr Ala
145                 150                 155                 160
Trp Ala Val Trp Thr Arg Ala Trp Thr Ala Glu Glu Asn Arg His Gly
                165                 170                 175
Asp Leu Leu Asn Lys Tyr Met Tyr Leu Thr Gly Arg Val Asp Ile Arg
            180                 185                 190
Gln Ile Glu Lys Thr Ile Gln Tyr Leu Ile Gly Ser Gly Met Asp Pro
        195                 200                 205
Arg Thr Glu Asn Asn Pro Tyr Leu Gly Phe Val Tyr Thr Ser Phe Gln
    210                 215                 220
Glu Arg Ala Thr Phe Ile Ser His Gly Asn Thr Ala Arg His Ala Lys
225                 230                 235                 240
Asp Phe Gly Asp Leu Lys Leu Ala Gln Ile Cys Gly Ile Ile Ala Ser
                245                 250                 255
Asp Glu Lys Arg His Glu Thr Ala Tyr Thr Lys Ile Val Glu Lys Leu
            260                 265                 270
Phe Glu Ile Asp Pro Asp Gly Thr Val Val Ala Leu Ala Asp Met Met
        275                 280                 285
Lys Lys Lys Ile Ser Met Pro Ala His Leu Met Phe Asp Gly Gln Asp
    290                 295                 300
Asp Lys Leu Phe Glu His Phe Ser Met Val Ala Gln Arg Leu Gly Val
305                 310                 315                 320
Tyr Thr Ala Arg Asp Tyr Ala Asp Ile Leu Glu Phe Leu Val Asp Arg
                325                 330                 335
Trp Lys Val Ala Asp Leu Thr Gly Leu Ser Gly Glu Gly Asn Lys Ala
            340                 345                 350
Gln Asp Tyr Leu Cys Thr Leu Ala Ser Arg Ile Arg Arg Leu Asp Glu
        355                 360                 365
Arg Ala Gln Ser Arg Ala Lys Lys Ala Gly Thr Leu Pro Phe Ser Trp
    370                 375                 380
Val Tyr Gly Arg Glu Val Gln Leu
385                 390
```

<210> SEQ ID NO 10
<211> LENGTH: 1709
<212> TYPE: DNA
<213> ORGANISM: Zea mays
<220> FEATURE:
<221> NAME/KEY: CDS
<222> LOCATION: (102)..(1280)

<400> SEQUENCE: 10

```
cggcacgagc acacacaagg gaaggggaca accacaagcg cctaagatcc cgtcctccgc    60
gtcgagatct ttgccgaggc ggtgaccgtc gagggatcgc c atg gcg ttg agg gcg    116
                                             Met Ala Leu Arg Ala
                                               1               5 tcc ccc gtg tcg cat ggc acc gcg gca gcg ccg ctg ccg cct ttc gcg    164
Ser Pro Val Ser His Gly Thr Ala Ala Ala Pro Leu Pro Pro Phe Ala
             10                  15                  20
```

-continued

| | | |
|---|---|---|
| cgg agg aag atg gcc cgt ggg gtg gtg gtg gcc atg gcg tcc acc atc<br>Arg Arg Lys Met Ala Arg Gly Val Val Val Ala Met Ala Ser Thr Ile<br>                 25                       30                         35 | 212 |
| aac agg gtc aaa act gtc aaa gaa ccc tat acc cct cca cga gag gta<br>Asn Arg Val Lys Thr Val Lys Glu Pro Tyr Thr Pro Pro Arg Glu Val<br>          40                     45                     50 | 260 |
| cat cgc caa att acc cat tca cta cca cct caa aag cgg gag att ttc<br>His Arg Gln Ile Thr His Ser Leu Pro Pro Gln Lys Arg Glu Ile Phe<br>55                       60                     65 | 308 |
| gat tca ctt caa cct tgg gcc aag gat aac cta ctg aac cta ctg aag<br>Asp Ser Leu Gln Pro Trp Ala Lys Asp Asn Leu Leu Asn Leu Leu Lys<br>70                 75                   80                 85 | 356 |
| cca gtt gaa aag tca tgg cag cca cag gac ttc cta cca gag cct tct<br>Pro Val Glu Lys Ser Trp Gln Pro Gln Asp Phe Leu Pro Glu Pro Ser<br>                 90                       95                    100 | 404 |
| tct gat ggg ttt tat gat gaa gtt aaa gaa ctg agg gag cgg gca aat<br>Ser Asp Gly Phe Tyr Asp Glu Val Lys Glu Leu Arg Glu Arg Ala Asn<br>                 105                   110                 115 | 452 |
| gaa ata cct gat gaa tac ttt gtt tgc tta gtt ggt gat atg gtt act<br>Glu Ile Pro Asp Glu Tyr Phe Val Cys Leu Val Gly Asp Met Val Thr<br>         120                     125                   130 | 500 |
| gag gaa gcc tta cct aca tac caa aca atg ctt aac act ctt gat gga<br>Glu Glu Ala Leu Pro Thr Tyr Gln Thr Met Leu Asn Thr Leu Asp Gly<br>135                     140                   145 | 548 |
| gtc cgg gat gaa act ggt gca agt tca acc acg tgg gcg gtt tgg aca<br>Val Arg Asp Glu Thr Gly Ala Ser Ser Thr Thr Trp Ala Val Trp Thr<br>150                   155                   160                 165 | 596 |
| agg gca tgg aca gct gaa gag aac aga cat ggt gac ctc ctt aac aag<br>Arg Ala Trp Thr Ala Glu Glu Asn Arg His Gly Asp Leu Leu Asn Lys<br>                 170                   175                 180 | 644 |
| tac atg tac ctt act gga cgg gtt gac atg aaa caa att gag aag acc<br>Tyr Met Tyr Leu Thr Gly Arg Val Asp Met Lys Gln Ile Glu Lys Thr<br>         185                     190                   195 | 692 |
| ata caa tat ctg att ggt tcc gga atg gat cct gga act gag aac aac<br>Ile Gln Tyr Leu Ile Gly Ser Gly Met Asp Pro Gly Thr Glu Asn Asn<br>200                   205                   210 | 740 |
| ccc tac ttg ggt ttc ctc tac aca tca ttc caa gaa agg gca aca ttt<br>Pro Tyr Leu Gly Phe Leu Tyr Thr Ser Phe Gln Glu Arg Ala Thr Phe<br>         215                     220                   225 | 788 |
| gtg tcg cat ggg aat act gca agg cat gcc aag gag tat ggt gat ctc<br>Val Ser His Gly Asn Thr Ala Arg His Ala Lys Glu Tyr Gly Asp Leu<br>230                   235                   240                 245 | 836 |
| aag ctg gcc cag ata tgt ggc acg ata gca gcc gat gag aag cgc cac<br>Lys Leu Ala Gln Ile Cys Gly Thr Ile Ala Ala Asp Glu Lys Arg His<br>                 250                   255                 260 | 884 |
| gaa aca gcc tac acc aag ata gtc gag aag ctc ttc gag atg gac cct<br>Glu Thr Ala Tyr Thr Lys Ile Val Glu Lys Leu Phe Glu Met Asp Pro<br>         265                     270                   275 | 932 |
| gat tac aca gtg ctt gcg ttt gct gac atg atg agg aag aag atc acg<br>Asp Tyr Thr Val Leu Ala Phe Ala Asp Met Met Arg Lys Lys Ile Thr<br>280                   285                   290 | 980 |
| atg cca gcc cat ctc atg tac gac ggt aag gac gac aac ctg ttc gag<br>Met Pro Ala His Leu Met Tyr Asp Gly Lys Asp Asp Asn Leu Phe Glu<br>295                     300                   305 | 1028 |
| cac ttc agc gcg gtg gcg cag agg ctg ggc gtc tac acc gcc aaa gac<br>His Phe Ser Ala Val Ala Gln Arg Leu Gly Val Tyr Thr Ala Lys Asp<br>310                   315                   320                 325 | 1076 |
| tac gcc gac atc ctc gag ttc ctg gtc cag agg tgg aaa gtc gcg gag<br>Tyr Ala Asp Ile Leu Glu Phe Leu Val Gln Arg Trp Lys Val Ala Glu<br>                 330                   335                 340 | 1124 |

-continued

```
ctc aca ggg ctg tct gga gaa ggg aga agc gcg cag gac ttt gtc tgt     1172
Leu Thr Gly Leu Ser Gly Glu Gly Arg Ser Ala Gln Asp Phe Val Cys
            345                 350                 355 acc ttg gcg ccg agg atc agg cgg ctg gat gat aga gct caa gcg agg     1220
Thr Leu Ala Pro Arg Ile Arg Arg Leu Asp Asp Arg Ala Gln Ala Arg
        360                 365                 370 gcg aag caa gca ccg gtt att cct ttc agt tgg gtt tat gac cgc aag     1268
Ala Lys Gln Ala Pro Val Ile Pro Phe Ser Trp Val Tyr Asp Arg Lys
    375                 380                 385 gtg cag ctt taa tcaagaacgc taggcaatgt gggcatttac tacgtatatc         1320
Val Gln Leu
390 attttcagtc ctggggttct ctataagaaa cagtctctag gttatctagc agggtagaat   1380 tcaactactc gtggatctca ctcggtgcaa agtagtgcaa agtacgctat ctgttgttac   1440 cgtgcaagct gcagagtttg gattactatg tgggcctggt ggtggagagg aattctgtgg   1500 ggtgcctgca gccagttatg agtggcagct ccatcgcaac tgagttgttg tattgaatat   1560 gttacaggac ctatagtaac cgaaagtaat aatatggagt ttgtatatcg acaagcttgc   1620 tttggtgatt gatgagaatc tgaagtaata atatggagtt tgcataaaaa aaaaaaaaa    1680 aaaaaaaaaa aaaaaaaaaa aaaaaaaa                                      1709
```

<210> SEQ ID NO 11
<211> LENGTH: 392
<212> TYPE: PRT
<213> ORGANISM: Zea mays

<400> SEQUENCE: 11

```
Met Ala Leu Arg Ala Ser Pro Val Ser His Gly Thr Ala Ala Pro
 1               5                  10                  15

Leu Pro Pro Phe Ala Arg Arg Lys Met Ala Arg Gly Val Val Ala
                20                  25                  30

Met Ala Ser Thr Ile Asn Arg Val Lys Thr Val Lys Glu Pro Tyr Thr
            35                  40                  45

Pro Pro Arg Glu Val His Arg Gln Ile Thr His Ser Leu Pro Pro Gln
        50                  55                  60

Lys Arg Glu Ile Phe Asp Ser Leu Gln Pro Trp Ala Lys Asp Asn Leu
65                  70                  75                  80

Leu Asn Leu Leu Lys Pro Val Glu Lys Ser Trp Gln Pro Gln Asp Phe
                85                  90                  95

Leu Pro Glu Pro Ser Ser Asp Gly Phe Tyr Asp Glu Val Lys Glu Leu
            100                 105                 110

Arg Glu Arg Ala Asn Glu Ile Pro Asp Glu Tyr Phe Val Cys Leu Val
        115                 120                 125

Gly Asp Met Val Thr Glu Glu Ala Leu Pro Thr Tyr Gln Thr Met Leu
    130                 135                 140

Asn Thr Leu Asp Gly Val Arg Asp Glu Thr Gly Ala Ser Ser Thr Thr
145                 150                 155                 160

Trp Ala Val Trp Thr Arg Ala Trp Thr Ala Glu Glu Asn Arg His Gly
                165                 170                 175

Asp Leu Leu Asn Lys Tyr Met Tyr Leu Thr Gly Arg Val Asp Met Lys
            180                 185                 190

Gln Ile Glu Lys Thr Ile Gln Tyr Leu Ile Gly Ser Gly Met Asp Pro
        195                 200                 205

Gly Thr Glu Asn Asn Pro Tyr Leu Gly Phe Leu Tyr Thr Ser Phe Gln
    210                 215                 220
```

```
Glu Arg Ala Thr Phe Val Ser His Gly Asn Thr Ala Arg His Ala Lys
225                 230                 235                 240

Glu Tyr Gly Asp Leu Lys Leu Ala Gln Ile Cys Gly Thr Ile Ala Ala
            245                 250                 255

Asp Glu Lys Arg His Glu Thr Ala Tyr Thr Lys Ile Val Glu Lys Leu
        260                 265                 270

Phe Glu Met Asp Pro Asp Tyr Thr Val Leu Ala Phe Ala Asp Met Met
    275                 280                 285

Arg Lys Lys Ile Thr Met Pro Ala His Leu Met Tyr Asp Gly Lys Asp
290                 295                 300

Asp Asn Leu Phe Glu His Phe Ser Ala Val Ala Gln Arg Leu Gly Val
305                 310                 315                 320

Tyr Thr Ala Lys Asp Tyr Ala Asp Ile Leu Glu Phe Leu Val Gln Arg
                325                 330                 335

Trp Lys Val Ala Glu Leu Thr Gly Leu Ser Gly Glu Gly Arg Ser Ala
            340                 345                 350

Gln Asp Phe Val Cys Thr Leu Ala Pro Arg Ile Arg Arg Leu Asp Asp
        355                 360                 365

Arg Ala Gln Ala Arg Ala Lys Gln Ala Pro Val Ile Pro Phe Ser Trp
    370                 375                 380

Val Tyr Asp Arg Lys Val Gln Leu
385                 390

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:   SYNTHETIC
      OLIGONUCLEOTIDE

<400> SEQUENCE: 12
aggacgctac cgtaggaa                                                       18

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:   SYNTHETIC
      OLIGONUCLEOTIDE

<400> SEQUENCE: 13
gcgatggcac tgcagta                                                        17

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:   SYNTHETIC
      OLIGONUCLEOTIDE

<400> SEQUENCE: 14
cttgagagaa gaaccacact c                                                   21

<210> SEQ ID NO 15
<211> LENGTH: 21
<212> TYPE: DNA
<213> ORGANISM: Artificial Sequence
```

```
<220> FEATURE:
<223> OTHER INFORMATION: Description of Artificial Sequence: SYNTHETIC
      OLIGONUCLEOTIDE

<400> SEQUENCE: 15
ctagacatat cgagcatgct g                                              21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 16
aggcgctgac ggtggcgacg ct                                             22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 17
gtgttggcga ggcacgtgag                                                20

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 18
acctcccgtc gcaccccggt ggtgatcagc catggtaggc tagcag                   46

<210> SEQ ID NO 19
<211> LENGTH: 1714
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 19
tctagaagtg tatgtatgtc aaagatctta tcgggataag agatatgata aagatcttaa    60
cggaatcaga gccaggtttg taaaaataga gttggactcg tgtacaactt ggtctctggc   120
ttagctccgt catgaattta gtaaccgact cgatatgtac cgtggaaccc ctagggcatg   180
agccatagga tcatcatatc caaacatgca ccaacaaatc caccacacat cgaagatcca   240
tattaagaag gggttatcta ctttacaatt tcagagtaac caatagagcc aaactcatag   300
cacaggggag cttcatatca gatggagcca ttgaattgat ataaaaagct gaagttctaa   360
aaagttttaa gtgctggaac ttcaaagccg ctaactagtg aagcaccgaa gccttccgtg   420
gagagataca tacacgacac gttagggacg taaaatgacg gaattataca gctacctcta   480
tatgtgacac ttatgtaata gaaaagacag aatccatatg aagatgtata atggatcaat   540
catataaata gataaacaat tgaggtgttt ggtttgatga atcactctat ccaaaataaa   600
gtggtgcatc atgggtttat tcctcaaatt tggtggcatg actacattcc acatattagt   660
```

```
actaagcaac taactttgag gaatgaggtg atgatgaatt aactcactcc attccacaaa        720
ccaaacaaaa atttgaggag tgagaagatg attgactatc tcattcctca aaccaaacac        780
ctcaaatata tctgctatcg ggattggcat tcctgtatcc ctacgcccgt gtaccccctg        840
tttagagaac ctcccaaagg tataagatgg cgaagattat tgttgtcttg tctttcatca        900
tatatcgagt cttccctag gatattatta ttggcaatga gcattacacg gttaatcgat         960
tgagagaaca tgcatctcac cttcagcaaa taattacgat aatccatatt ttacgcttcg       1020
taacttctca tgagtttcga tatacaaatt tgttttctgg acaccctacc attcatcctc       1080
ttcggagaag agaggaagtg tcctcaattt aaatatgttg tcatgctgta gttcttcaca       1140
aaatctcaac aggtaccaag cacattgttt ccacaaatta tattttagtc acaataaatc       1200
tatattatta ttaatatact aaaactatac tgacgctcag atgctttac tagttcttgc        1260 tagtatgtga tgtaggtcta cgtggaccag aaaatagtga gacacggaag acaaaagaag       1320
taaaagaggc ccggactacg gcccacatga gattcggccc cgccacctcc ggcaaccagc       1380
ggccgatcca acggcagtgc gcgcacacac acaacctcgt atatatcgcc gcgcggaagc       1440
ggcgcgaccg aggaagcctt gtcctcgaca ccccctacac aggtgtcgcg ctgccccga        1500 cacgagtccc gcatgcgtcc cacgcggccg cgccagatcc cgcctccgcg cgttgccacg       1560
ccctctataa acacccagct ctccctcgcc ctcatctacc tcactcgtag tcgtagctca       1620
agcatcagcg gcagcggcag cggcaggagc tctgggcagc gtgcgcacgt ggggtaccta       1680
gctcgctctg ctagcctacc atggtacgtg gcat                                   1714
```

```
<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 20
cttatgtaat agaaaagaca ggatccatat gg                                       32

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 21
gaggagtgag gatcctgatt gactatctca ttc                                      33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 22
tctggacacc ctaccattgg atcctcttcg gag                                      33
```

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: SYNTHETIC
    OLIGONUCLEOTIDE

<400> SEQUENCE: 23
agagttggat ccgtgtacaa cttggtctct gg                                    32

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: SYNTHETIC
    OLIGONUCLEOTIDE

<400> SEQUENCE: 24
gccgctgatg ctcgagctac gactacgagt gaggtag                               37

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: SYNTHETIC
    OLIGONUCLEOTIDE

<400> SEQUENCE: 25
atgcgggact cgagtcgggg gcagcgcgac ac                                    32

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: SYNTHETIC
    OLIGONUCLEOTIDE

<400> SEQUENCE: 26
gtggcggggc cgaatctcga gtgggccgta gt                                    32

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: SYNTHETIC
    OLIGONUCLEOTIDE

<400> SEQUENCE: 27
gccacgtgcc atggtaggct agcagagcga gct                                   33

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: SYNTHETIC
    OLIGONUCLEOTIDE

<400> SEQUENCE: 28
aacacacacc catggatatc acag                                             24

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 29
ggtctgactt acgggtgtc                                                    19

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 30
ctctcccgtc ctcgagaaac cctcc                                             25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 31
cttggcagcc atggctcgat ggttc                                             25

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 32
atggtgagcg ccagaatcgt tgtcctcctc                                        30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 33
catcctggcg gtcaccatcc tcaggagcgt                                        30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 34
atagggaatt ctctgttttt ctaaaaaaaa                                        30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: SYNTHETIC OLIGONUCLEOTIDE

<400> SEQUENCE: 35
gctcaccatg gtgtagtgtc tgtcactgtg                                    30

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: SYNTHETIC OLIGONUCLEOTIDE

<400> SEQUENCE: 36
gggggatcca agcttgagga gacaggagat aaaagt                             36

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: SYNTHETIC OLIGONUCLEOTIDE

<400> SEQUENCE: 37
gggctgcagc tcgagggtgt agtgtctgtc actgtgata                          39

<210> SEQ ID NO 38
<211> LENGTH: 1108
<212> TYPE: DNA
<213> ORGANISM: Artificial Sequence
<220> FEATURE:
<223> OTHER INFORMATION: Description of Artificial Sequence: SYNTHETIC OLIGONUCLEOTIDE

<400> SEQUENCE: 38
atccatatga agatgtataa tggatcaatc atataaatag ataaacaatt gaggtgtttg    60
gtttgatgaa tcactctatc caaaataaag tggtgcatca tgggtttatt cctcaaattt   120
ggtggcatga ctacattcca catattagta ctaagcaact aactttgagg aatgaggtga   180
tgatgaatta actcactcca ttccacaaac caaacaaaaa tttgaggagt gagaagatga   240
ttgactatct cattcctcaa accaaacacc tcaaatatat ctgctatcgg gattggcatt   300
cctgtatccc tacgcccgtg tacccctgt ttagagaacc tcccaaaggt ataagatggc   360
gaagattatt gttgtcttgt ctttcatcat atatcgagtc tttccctagg atattattat   420
tggcaatgag cattacacgg ttaatcgatt gagagaacat gcatctcacc ttcagcaaat   480
aattacgata atccatattt tacgcttcgt aacttctcat gagtttcgat atacaaattt   540
gttttctgga caccctacca ttcatcctct tcggagaaga gaggaagtgt cctcaattta   600
aatatgttgt catgctgtag ttcttcacaa aatctcaaca ggtaccaagc acattgtttc   660
cacaaattat attttagtca caataaatct atattattat taatatacta aaactatact   720
gacgctcaga tgcttttact agttcttgct agtatgtgat gtaggtctac gtggaccaga   780
aaatagtgag acacggaaga caaaagaagt aaaagaggcc cggactacgg cccacatgag   840
attcggcccc gccacctccg gcaaccagcg gccgatccaa cggcagtgcg cgcacacaca   900

-continued

| | |
|---|---|
| caacctcgta tatatcgccg cgcggaagcg gcgcgaccga ggaagccttg tcctcgacac | 960 |
| ccccctacaca ggtgtcgcgc tgcccccgac acgagtcccg catgcgtccc acgcggccgc | 1020 |
| gccagatccc gcctccgcgc gttgccacgc cctctataaa cacccagctc tccctcgccc | 1080 |
| tcatctacct cactcgtagt cgtagctc | 1108 |

<210> SEQ ID NO 39
<211> LENGTH: 871
<212> TYPE: DNA
<213> ORGANISM: Zea mays

<400> SEQUENCE: 39

| | |
|---|---|
| tgattgacta tctcattcct caaaccaaac acctcaaata tatctgctat cgggattggc | 60 |
| attcctgtat ccctacgccc gtgtaccccc tgtttagaga acctcccaaa ggtataagat | 120 |
| ggcgaagatt attgttgtct tgtctttcat catatatcga gtctttccct aggatattat | 180 |
| tattggcaat gagcattaca cggttaatcg attgagagaa catgcatctc accttcagca | 240 |
| aataattacg ataatccata ttttacgctt cgtaacttct catgagtttc gatatacaaa | 300 |
| tttgttttct ggacacccta ccattcatcc tcttcggaga agagaggaag tgtcctcaat | 360 |
| ttaaatatgt tgtcatgctg tagttcttca caaaatctca acaggtacca agcacattgt | 420 |
| ttccacaaat tatattttag tcacaataaa tctatattat tattaatata ctaaaactat | 480 |
| actgacgctc agatgctttt actagttctt gctagtatgt gatgtaggtc tacgtggacc | 540 |
| agaaaatagt gagacacgga agacaaaaga agtaaaagag gcccggacta cggcccacat | 600 |
| gagattcggc cccgccacct ccggcaacca gcggccgatc caacggcagt gcgcgcacac | 660 |
| acacaacctc gtatatatcg ccgcgcggaa gcggcgcgac cgaggaagcc ttgtcctcga | 720 |
| caccccctac acaggtgtcg cgctgccccc gacacgagtc ccgcatgcgt cccacgcggc | 780 |
| cgcgccagat cccgcctccg cgcgttgcca cgccctctat aaacacccag ctctccctcg | 840 |
| ccctcatcta cctcactcgt agtcgtagct c | 871 |

<210> SEQ ID NO 40
<211> LENGTH: 545
<212> TYPE: DNA
<213> ORGANISM: Zea mays

<400> SEQUENCE: 40

| | |
|---|---|
| atcctcttcg gagaagagag gaagtgtcct caatttaaat atgttgtcat gctgtagttc | 60 |
| ttcacaaaat ctcaacaggt accaagcaca ttgtttccac aaattatatt ttagtcacaa | 120 |
| taaatctata ttattattaa tatactaaaa ctatactgac gctcagatgc ttttactagt | 180 |
| tcttgctagt atgtgatgta ggtctacgtg gaccagaaaa tagtgagaca cggaagacaa | 240 |
| aagaagtaaa agaggcccgg actacggccc acatgagatt cggccccgcc acctccggca | 300 |
| accagcggcc gatccaacgg cagtgcgcgc acacacacaa cctcgtatat atcgccgcgc | 360 |
| ggaagcggcg cgaccgagga agccttgtcc tcgacacccc ctacacaggt gtcgcgctgc | 420 |
| ccccgacacg agtcccgcat gcgtcccacg cggccgcgcc agatcccgcc tccgcgcgtt | 480 |
| gccacgccct ctataaacac ccagctctcc ctcgccctca tctacctcac tcgtagtcgt | 540 |
| agctc | 545 |

<210> SEQ ID NO 41
<211> LENGTH: 952
<212> TYPE: DNA
<213> ORGANISM: Zea mays

```
<400> SEQUENCE: 41
tgattgacta tctcattcct caaaccaaac acctcaaata tatctgctat cgggattggc      60
attcctgtat ccctacgccc gtgtaccccc tgtttagaga acctcccaaa ggtataagat     120
ggcgaagatt attgttgtct tgtctttcat catatatcga gtctttccct aggatattat     180
tattggcaat gagcattaca cggttaatcg attgagagaa catgcatctc accttcagca     240
aataattacg ataatccata ttttacgctt cgtaacttct catgagtttc gatatacaaa     300
tttgttttct ggacacccta ccattcatcc tcttcggaga agagaggaag tgtcctcaat     360
ttaaatatgt tgtcatgctg tagttcttca caaaatctca acaggtacca agcacattgt     420
ttccacaaat tatattttag tcacaataaa tctatattat tattaatata ctaaaactat     480
actgacgctc agatgctttt actagttctt gctagtatgt gatgtaggtc tacgtggacc     540
agaaaatagt gagacacgga agacaaaaga agtaaaagag gcccggacta cggcccacat     600
gagattcggc cccgccacct ccggcaacca gcggccgatc caacggcagt gcgcgcacac     660
acacaacctc gtatatatcg ccgcgcggaa gcggcgcgac cgaggaagcc ttgtcctcga     720
caccccctac acaggtgtcg cgctgccccc gacacgagtc ccgcatgcgt cccacgcggc     780
cgcgccagat cccgcctccg cgcgttgcca cgccctctat aaacacccag ctctccctcg     840
ccctcatcta cctcactcgt agtcgtagct caagcatcag cggcagcggc agcggcagga     900
gctctgggca gcgtgcgcac gtggggtacc tagctcgctc tgctagccta cc            952

<210> SEQ ID NO 42
<211> LENGTH: 1403
<212> TYPE: DNA
<213> ORGANISM: Zea mays

<400> SEQUENCE: 42
cgtgtacaac ttggtctctg gcttagctcc gtcatgaatt tagtaaccga ctcgatatgt      60
accgtggaac ccctagggca tgagccatag gatcatcata tccaaacatg caccaacaaa     120
tccaccacac atcgaagatc catattaaga agggggttatc tactttacaa tttcagagta     180
accaatagag ccaaactcat agcacagggg agcttcatat cagatggagc cattgaattg     240
atataaaaag ctgaagttct aaaaagtttt aagtgctgga acttcaaagc cgctaactag     300
tgaagcaccg aagccttccg tggagagata catacacgac acgttaggga cgtaaaatga     360
cggaattata cagctacctc tatatgtgac acttatgtaa tagaaaagac agaatccata     420
tgaagatgta taatggatca atcatataaa tagataaaca attgaggtgt ttggtttgat     480
gaatcactct atccaaaata aagtggtgca tcatgggttt attcctcaaa tttggtggca     540
tgactacatt ccacatatta gtactaagca actaactttg aggaatgagg tgatgatgaa     600
ttaactcact ccattccaca aaccaaacaa aaatttgagg agtgagaaga tgattgacta     660
tctcattcct caaaccaaac acctcaaata tatctgctat cgggattggc attcctgtat     720
ccctacgccc gtgtaccccc tgtttagaga acctcccaaa ggtataagat ggcgaagatt     780
attgttgtct tgtctttcat catatatcga gtctttccct aggatattat tattggcaat     840
gagcattaca cggttaatcg attgagagaa catgcatctc accttcagca aataattacg     900
ataatccata ttttacgctt cgtaacttct catgagtttc gatatacaaa tttgttttct     960
ggacacccta ccattcatcc tcttcggaga agagaggaag tgtcctcaat ttaaatatgt    1020
tgtcatgctg tagttcttca caaaatctca acaggtacca agcacattgt ttccacaaat    1080
tatattttag tcacaataaa tctatattat tattaatata ctaaaactat actgacgctc    1140
```

```
agatgctttt actagttctt gctagtatgt gatgtaggtc tacgtggacc agaaaatagt    1200
gagacacgga agacaaaaga agtaaaagag gcccggacta cggcccacat gagattcggc    1260
cccgccacct ccggcaacca gcggccgatc caacggcagt gcgcgcacac acacaacctc    1320
gtatatatcg ccgcgcggaa gcggcgcgac cgaggaagcc ttgtcctcga cacccccctac   1380 acaggtgtcg cgctgccccc gac                                            1403
```

<210> SEQ ID NO 43
<211> LENGTH: 990
<212> TYPE: DNA
<213> ORGANISM: Zea mays

<400> SEQUENCE: 43

```
atccatatga agatgtataa tggatcaatc atataaatag ataaacaatt gaggtgtttg      60
gtttgatgaa tcactctatc caaaataaag tggtgcatca tgggtttatt cctcaaattt     120
ggtggcatga ctacattcca catattagta ctaagcaact aactttgagg aatgaggtga     180
tgatgaatta actcactcca ttccacaaac caaacaaaaa tttgaggagt gagaagatga     240
ttgactatct cattcctcaa accaaacacc tcaaatatat ctgctatcgg gattggcatt     300
cctgtatccc tacgcccgtg tacccctgt ttagagaacc tcccaaaggt ataagatggc      360
gaagattatt gttgtcttgt ctttcatcat atatcgagtc tttccctagg atattattat     420
tggcaatgag cattacacgg ttaatcgatt gagagaacat gcatctcacc ttcagcaaat     480
aattacgata atccatattt tacgcttcgt aacttctcat gagtttcgat atacaaattt     540
gttttctgga caccctacca ttcatcctct tcggagaaga gaggaagtgt cctcaattta     600
aatatgttgt catgctgtag ttcttcacaa aatctcaaca ggtaccaagc acattgtttc     660
cacaaattat attttagtca caataaatct atattattat taatatacta aaactatact     720
gacgctcaga tgcttttact agttcttgct agtatgtgat gtaggtctac gtggaccaga    780
aaatagtgag acacggaaga caaaagaagt aaaagaggcc cggactacgg cccacatgag     840
attcggcccc gccacctccg gcaaccagcg gccgatccaa cggcagtgcg cgcacacaca     900
caacctcgta tatatcgccg cgcggaagcg cgcgaccga ggaagccttg tcctcgacac      960
cccctacaca ggtgtcgcgc tgcccccgac                                     990
```

<210> SEQ ID NO 44
<211> LENGTH: 753
<212> TYPE: DNA
<213> ORGANISM: Zea mays

<400> SEQUENCE: 44

```
tgattgacta tctcattcct caaaccaaac acctcaaata tatctgctat cgggattggc     60
attcctgtat ccctacgccc gtgtaccccc tgtttagaga acctcccaaa ggtataagat    120
ggcgaagatt attgttgtct tgtctttcat catatatcga gtctttccct aggatattat    180
tattggcaat gagcattaca cggttaatcg attgagagaa catgcatctc accttcagca    240
aataattacg ataatccata ttttacgctt cgtaacttct catgagtttc gatatacaaa    300
tttgttttct ggacacccta ccattcatcc tcttcggaga agagaggaag tgtcctcaat    360
ttaaatatgt tgtcatgctg tagttcttca caaaatctca acaggtacca agcacattgt    420
ttccacaaat tatattttag tcacaataaa tctatattat tattaatata ctaaaactat    480
actgacgctc agatgctttt actagttctt gctagtatgt gatgtaggtc tacgtggacc    540
agaaaatagt gagacacgga agacaaaaga agtaaaagag gcccggacta cggcccacat    600
```

```
gagattcggc cccgccacct ccggcaacca gcggccgatc caacggcagt gcgcgcacac      660
acacaacctc gtatatatcg ccgcgcggaa gcggcgcgac cgaggaagcc ttgtcctcga      720 cacccccta c acaggtgtcg cgctgccccc gac                                  753

<210> SEQ ID NO 45
<211> LENGTH: 427
<212> TYPE: DNA
<213> ORGANISM: Zea mays

<400> SEQUENCE: 45
atcctcttcg gagaagagag gaagtgtcct caatttaaat atgttgtcat gctgtagttc       60
ttcacaaaat ctcaacaggt accaagcaca ttgtttccac aaattatatt ttagtcacaa      120
taaatctata ttattattaa tatactaaaa ctatactgac gctcagatgc ttttactagt      180
tcttgctagt atgtgatgta ggtctacgtg gaccagaaaa tagtgagaca cggaagacaa      240
aagaagtaaa agaggcccgg actacggccc acatgagatt cggccccgcc acctccggca      300
accagcggcc gatccaacgg cagtgcgcgc acacacacaa cctcgtatat atcgccgcgc      360
ggaagcggcg cgaccgagga agccttgtcc tcgacacccc ctacacaggt gtcgcgctgc      420
ccccgac                                                                427

<210> SEQ ID NO 46
<211> LENGTH: 1248
<212> TYPE: DNA
<213> ORGANISM: Zea mays

<400> SEQUENCE: 46
cgtgtacaac ttggtctctg gcttagctcc gtcatgaatt tagtaaccga ctcgatatgt       60
accgtggaac ccctagggca tgagccatag gatcatcata tccaaacatg caccaacaaa      120
tccaccacac atcgaagatc catattaaga aggggttatc tactttacaa tttcagagta      180
accaatagag ccaaactcat agcacagggg agcttcatat cagatggagc cattgaattg      240
atataaaaag ctgaagttct aaaaagtttt aagtgctgga acttcaaagc cgctaactag      300
tgaagcaccg aagccttccg tggagagata catacacgac acgttaggga cgtaaaatga      360
cggaattata cagctacctc tatatgtgac acttatgtaa tagaaaagac agaatccata      420
tgaagatgta aatggatca atcatataaa tagataaaca attgaggtgt ttggtttgat      480
gaatcactct atccaaaata aagtggtgca tcatgggttt attcctcaaa tttggtggca      540
tgactacatt ccacatatta gtactaagca actaactttg aggaatgagg tgatgatgaa      600
ttaactcact ccattccaca aaccaaacaa aaatttgagg agtgagaaga tgattgacta      660
tctcattcct caaaccaaac acctcaaata tatctgctat cgggattggc attcctgtat      720
ccctacgccc gtgtaccccc tgtttagaga acctcccaaa ggtataagat ggcgaagatt      780
attgttgtct tgtctttcat catatatcga gtctttccct aggatattat tattggcaat      840
gagcattaca cggttaatcg attgagagaa catgcatctc accttcagca ataattacg      900 ataatccata ttttacgctt cgtaacttct catgagtttc gatatacaaa tttgtttttct      960 ggacacccta ccattcatcc tcttcggaga agagaggaag tgtcctcaat ttaaatatgt    1020
tgtcatgctg tagttcttca caaatctca acaggtacca agcacattgt tccacaaat    1080 tatatttttag tcaataaa tctatattat tattaatata ctaaaactat actgacgctc    1140
agatgctttt actagttctt gctagtatgt gatgtaggtc tacgtggacc agaaaatagt    1200
gagacacgga agacaaaaga agtaaaagag gcccggacta cggcccac                 1248
```

<210> SEQ ID NO 47
<211> LENGTH: 835
<212> TYPE: DNA
<213> ORGANISM: Zea mays

<400> SEQUENCE: 47

| atccatatga agatgtataa tggatcaatc atataaatag ataaacaatt gaggtgtttg | 60 |
| gtttgatgaa tcactctatc caaaataaag tggtgcatca tgggtttatt cctcaaattt | 120 |
| ggtggcatga ctacattcca catattagta ctaagcaact aactttgagg aatgaggtga | 180 |
| tgatgaatta actcactcca ttccacaaac caaacaaaaa tttgaggagt gagaagatga | 240 |
| ttgactatct cattcctcaa accaaacacc tcaaatatat ctgctatcgg gattggcatt | 300 |
| cctgtatccc tacgcccgtg tacccctgt ttagagaacc tcccaaaggt ataagatggc | 360 |
| gaagattatt gttgtcttgt ctttcatcat atatcgagtc tttccctagg atattattat | 420 |
| tggcaatgag cattacacgg ttaatcgatt gagagaacat gcatctcacc ttcagcaaat | 480 |
| aattacgata atccatattt tacgcttcgt aacttctcat gagtttcgat atacaaattt | 540 |
| gttttctgga caccctacca ttcatcctct tcggagaaga gaggaagtgt cctcaattta | 600 |
| aatatgttgt catgctgtag ttcttcacaa aatctcaaca ggtaccaagc acattgtttc | 660 |
| cacaaattat attttagtca caataaatct atattattat taatatacta aaactatact | 720 |
| gacgctcaga tgcttttact agttcttgct agtatgtgat gtaggtctac gtggaccaga | 780 |
| aaatagtgag acacggaaga caaagaagt aaaagaggcc cggactacgg cccac | 835 |

<210> SEQ ID NO 48
<211> LENGTH: 598
<212> TYPE: DNA
<213> ORGANISM: Zea mays

<400> SEQUENCE: 48

| tgattgacta tctcattcct caaaccaaac acctcaaata tatctgctat cgggattggc | 60 |
| attcctgtat ccctacgccc gtgtaccccc tgtttagaga acctcccaaa ggtataagat | 120 |
| ggcgaagatt attgttgtct tgtctttcat catatatcga gtctttccct aggatattat | 180 |
| tattggcaat gagcattaca cggttaatcg attgagagaa catgcatctc accttcagca | 240 |
| aataattacg ataatccata ttttacgctt cgtaacttct catgagtttc gatatacaaa | 300 |
| tttgttttct ggacacccta ccattcatcc tcttcggaga agagaggaag tgtcctcaat | 360 |
| ttaaatatgt tgtcatgctg tagttcttca caaaatctca acaggtacca agcacattgt | 420 |
| ttccacaaat tatattttag tcacaataaa tctatattat tattaatata ctaaaactat | 480 |
| actgacgctc agatgctttt actagttctt gctagtatgt gatgtaggtc tacgtggacc | 540 |
| agaaaatagt gagacacgga agacaaaaga gtaaaagag gcccggacta cggcccac | 598 |

<210> SEQ ID NO 49
<211> LENGTH: 272
<212> TYPE: DNA
<213> ORGANISM: Zea mays

<400> SEQUENCE: 49

| atcctcttcg gagaagagag gaagtgtcct caatttaaat atgttgtcat gctgtagttc | 60 |
| ttcacaaaat ctcaacaggt accaagcaca ttgtttccac aaattatatt ttagtcacaa | 120 |
| taaatctata ttattattaa tatactaaaa ctatactgac gctcagatgc ttttactagt | 180 | tcttgctagt atgtgatgta ggtctacgtg gaccagaaaa tagtgagaca cggaagacaa    240 aagaagtaaa agaggcccgg actacggccc ac                                  272

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 50
cggggtaccg atgaccgaga aggagcggg                                       29

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 51
ggcggtacct agaacttctt gttgtacca                                       29

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 52
ggcctccgcc atggcgctcc gctccacgac g                                    31

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 53
ctccaactca agcagtcgcc atgggtttcc                                      30

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 54
ctgcactgaa agttttggca                                                 20

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

```
<400> SEQUENCE: 55
agtacagcgg ccaggcggcg tagcg                                       25

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 56 aagggagag agaggtgagg                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 57
tgcattgaag gtggtggtaa                                             20

<210> SEQ ID NO 58
<211> LENGTH: 6337
<212> TYPE: DNA
<213> ORGANISM: Zea mays

<400> SEQUENCE: 58
gtcgactcta gaggatccga ttgactatct cattcctcca aacccaaaca cctcaaatat    60
atctgctatc gggattggca ttcctgtatc cctacgcccg tgtaccccct gtttagagaa   120
cctcccaagg tataagatgg cgaagattat tgttgtcttg tctttcatca tatatcgagt   180
ctttccctag gatattatta ttggcaatga gcattacacg gttaatcgat tgagagaaca   240
tgcatctcac cttcagcaaa taattacgat aatccatatt ttacgcttcg taacttctca   300
tgagtttcga tatacaaatt tgtttctgg acaccctacc attcatcctc ttcggagaag    360
agaggaagtg tcctcaattt aaatatgttg tcatgctgta gttcttcacc caatctcaac   420
aggtaccaag cacattgttt ccacaaatta tattttagtc acaataaatc tatattatta   480
ttaatatact aaaactatac tgacgctcag atgcttttac tagttcttgc tagtatgtga   540
tgtaggtcta cgtggaccag aaaatagtga gacacggaag acaaaagaag taaaagaggc   600
ccggactacg gcccacatga gattcggccc cgccacctcc ggcaaccagc ggccgatcca   660
acggaagtgc gcgcacacac acaacctcgt atatatcgcc gcgcggaagc ggcgcgaccg   720
aggaagcctt gtcctcgaca ccccctacac aggtgtcgcg ctgccccga cacgagtccc    780 gcatgcgtcc cacgcggccg cgccagatcc cgcctccgcg cgttgccacg ccctctataa   840
acacccagct ctccctcgcc ctcatctacc tcactcgtag tcgtagctcg agaaaccctc   900
cctccctcct ccattggact gcttgctccc tgttgaccat tggggtatgc ttgctctcct   960
gttcatctcc gtgctaaacc tctgtcctct gggtgggttt ttgctgggat tttgagctaa  1020
tctgctggcc gcggtagaaa agaccgtgtc ccctgatgag ctcaagcgct cgccttagcc  1080
gcgtccttgt cccccgccat tcttgcggt ttcgctgtgt tcccgtgact cgccgggtgc   1140
gtcatcgcct gaatcttgtc tgggctctgc tgacatgttc ttggctagtt gggtttatag  1200
attcctctga tctaaaaccg tgcctgtgct gcgcacagaa ctctcccctg tcctttcctg  1260
```

-continued

```
gggttttggt tacgtggtgg tagtaagctt ggatttgcac atggataaag ttgttctaag    1320
ctccgtggtt tgcttgagat cttgctgtta ttgcgtgccg tgctcacttc ttttgcaatc    1380
cgaggaatga atttgtcgtt tactcgtttt ggtggattat tagcgcgaaa aaaaactctt    1440
ttttttgtt cttttactac gaaaagcatc ttcttggatt ttgctatctt cttttactac    1500
gaaaaactct tgagtctagg aatttgaatt tgtgatgtcc attcttgcag tgcgctgtgc    1560
tttattggga agccaaatcc tattattttc tgcctctagg gtctgaatgg aatcagtact    1620
attgagacaa aatcaatcca atcaagttga tttctttctt taaaaatatt atcacagaac    1680
taagtgcttg tgcggaatca gtactggctt ttgtttggtg gaggatcaat acttgctttt    1740
gttttggggt ggcaactgtt ttgctataag attccatgtg ttcctgttga gatgaatcat    1800
atatagtata gctgcatact acaaatctgt ttttcaaatt taggttgctt tggcatgatc    1860
aattttttt cagacagtct ttctaagtgg tagctcttga tttcttgttc ttctacaact    1920
ggtgctgctg aatcttgacc gtatagctcg aattgcagta ttctgaacca tcgagccatg    1980
aattccccg atgaccgaga aggagcggga gaagcaggag cagctcgccc gagctaccgg    2040
tggcgccgcg atgcagcggt cgccggtgga gaagcctccg ttcactctgg gtcagatcaa    2100
gaaggccatc ccgccacact gcttcgagcg ctcggtgctc aagtccttct cgtacgtggt    2160
ccacgacctg gtgatcgccg cggcgctcct ctacttcgcg ctggccatca taccggcgct    2220
cccaagcccg ctccgctacg ccgcctggcc gctgtactgg atcgcgcagg ggtgcgtgtg    2280
caccggcgtg tgggtcatcg cgcacgagtg cggccaccac gccttctcgg actactcgct    2340
cctggacgac gtggtcggcc tggtgctgca ctcgtcgctc atggtgccct acttctcgtg    2400
gaagtacagc caccggcgcc accactccaa cacggggtcc ctggagcgcg acgaggtgtt    2460
cgtgcccaag aagaaggagg cgctgccgtg gtacaccccg tacgtgtaca caacccggt    2520
cggccgggtg gtgcacatcg tggtgcagct cacctcgggg tggccgctgt acctggcgac    2580
caacgcgtcg gggcggccgt acccgcgctt cgcctgccac ttcgacccct acggcccat    2640
ctacaacgac cgggagcgcg cccagatctt cgtctcggac gccggcgtcg tggccgtggc    2700
gttcgggctg tacaagctgg cggcggcgtt cggggtctgg tgggtggtgc gcgtgtacgc    2760
cgtgccgctg ctgatcgtga acgcgtggct ggtgctcatc acctacctgc agcacaccca    2820
cccgtcgctc ccccactacg actcgagcga gtgggactgg ctgcgcggcg cgctggccac    2880
catggaccgc gactacggca tcctcaaccg cgtgttccac aacatcacgg acacgcacgt    2940
cgcgcaccac ctcttctcca ccatgccgca ctaccacgcc atggaggcca ccaaggcgat    3000
caggcccatc ctcggcgact actaccactt cgacccgacc cctgtcgcca aggcgacctg    3060
gcgcgaggcc ggggaatgca tctacgtcga gcccgaggac cgcaagggcg tcttctggta    3120
caacaagaag ttctaggggg gtacctaaag aaggagtgcg tcgaagcaga tcgttcaaac    3180
atttggcaat aaagtttctt aagattgaat cctgttgccg gtcttgcgat gattatcata    3240
taatttctgt tgaattacgt taagcatgta ataattaaca tgtaatgcat gacgttattt    3300
atgagatggg tttttatgat tagagtcccg caattataca tttaatacgc gatagaaaac    3360
aaaatatagc gcgcaaacta ggataaaatta tcgcgcgcgg tgtcatctat gttactagat    3420
cgatgtcgac tctagaaagc ttactagtga tgcatattct atagtgtcac ctaaatctgc    3480
ggccgctgac caagtcagct tggcactggc cgtcgtttta caacgtcgtg actgggaaaa    3540
ccctggcgtt acccaactta atcgccttgc agcacatccc cctttcgcca gctggcgtaa    3600
tagcgaagag gcccgcaccg atcgcccttc ccaacagttg cgcagcctga atggcgaatg    3660
```

-continued

```
ggaaattgta acgttaata ttttgttaat attttgttaa aattcgcgtt aaattttgt      3720 taaatcagct catttttaa ccaataggcc gaaatcggca aaatcccta taaatcaaaa       3780 gaatagaccg atatagggtt gagtgttgtt ccagtttgga acaagagtcc actattaaag    3840
aacgtggact ccaacgtcaa agggcgaaaa accgtctatc agggcgatgg cccactacgt    3900
gaaccatcac cctaatcaag ttttttgggg tcgaggtgcc gtaaagcact aaatcggaac    3960
cctaaaggga tgccccgatt tagagcttga cggggaaagc cggcgaacgt ggcgagaaag    4020
gaagggaaga aagcgaaagg agcgggcgct agggcgctgg caagtgtagc ggtcacgctg    4080
cgcgtaacca ccacacccgc cgcgcttaat gcgccgctac agggcgcgtc aggtggcact    4140
tttcggggaa atgtgcgcgg aacccctatt tgtttatttt tctaaataca ttcaaatatg    4200
tatccgctca tgagacaata accctgataa atgcttcaat aatattgaaa aaggaagagt    4260
atgagtattc aacatttccg tgtcgccctt attccctttt ttgcggcatt ttgccttcct    4320 gttttgctc acccagaaac gctggtgaaa gtaaaagatg ctgaagatca gttgggtgca    4380
cgagtgggtt acatcgaact ggatctcaac agcggtaaga tccttgagag ttttcgcccc    4440
gaagaacgtt ttccaatgat gagcactttt aaagttctgc tatgtggcgc ggtattatcc    4500
cgtattgacg ccgggcaaga gcaactcggt cgccgcatac actattctca gaatgacttg    4560
gttgagtact caccagtcac agaaaagcat cttacggatg gcatgacagt aagagaatta    4620
tgcagtgctg ccataaccat gagtgataac actgcggcca acttacttct gacaacgatc    4680
ggaggaccga aggagctaac cgcttttttg cacaacatgg gggatcatgt aactcgcctt    4740
gatcgttggg aaccggagct gaatgaagcc ataccaaacg acgagcgtga ccacgatg     4800 cctgtagcaa tggcaacaac gttgcgcaaa ctattaactg gcgaactact tactctagct    4860
tcccggcaac aattaataga ctggatggag gcggataaag ttgcaggacc acttctgcgc    4920
tcggcccttc cggctggctg gtttattgct gataaatctg gagccggtga gcgtgggtct    4980
cgcggtatca ttgcagcact ggggccagat ggtaagccct cccgtatcgt agttatctac    5040
acgacgggga gtcaggcaac tatggatgaa cgaaatagac agatcgctga gataggtgcc    5100
tcactgatta agcattggta actgtcagac caagtttact catatatact ttagattgat    5160
ttaaaacttc attttaatt taaaaggatc taggtgaaga tcctttttga taatctcatg    5220
accaaaatcc cttaacgtga gttttcgttc cactgagcgt cagacccccgt agaaaagatc    5280 aaaggatctt cttgagatcc tttttttctg cgcgtaatct gctgcttgca acaaaaaaaa     5340
ccaccgctac cagcggtggt ttgtttgccg gatcaagagc taccaactct ttttccgaag    5400
gtaactggct tcagcagagc gcagatacca aatactgtcc ttctagtgta gccgtagtta    5460
ggccaccact tcaagaactc tgtagcaccg cctacatacc tcgctctgct aatcctgtta    5520
ccagtggctg ctgccagtgg cgataagtcg tgtcttaccg ggttggactc aagacgatag    5580
ttaccggata aggcgcagcg gtcgggctga acggggggtt cgtgcacaca gcccagcttg    5640
gagcgaacga cctacaccga actgagatac ctacagcgtg agctatgaga aagcgccacg    5700
cttcccgaag ggagaaaggc ggacaggtat ccggtaagcg gcagggtcgg aacaggagag    5760
cgcacgaggg agcttccagg gggaaacgcc tggtatcttt atagtcctgt cgggtttcgc    5820
cacctctgac ttgagcgtcg attttttgtga tgctcgtcag ggggcggag cctatggaaa    5880 aacgccagca acgcggcctt tttacggttc ctggcctttt gctggccttt tgctcacatg    5940
ttctttcctg cgttatcccc tgattctgtg gataaccgta ttaccgcctt tgagtgagct    6000
gataccgctc gccgcagccg aacgaccgag cgcagcgagt cagtgagcga ggaagcggaa    6060
```

-continued

```
gagcgcccaa tacgcaaacc gcctctcccc gcgcgttggc cgattcatta atgcagctgg      6120
cacgacaggt ttcccgactg gaaagcgggc agtgagcgca acgcaattaa tgtgagttag      6180
ctcactcatt aggcacccca ggctttacac tttatgcttc cggctcgtat gttgtgtgga      6240
attgtgagcg gataacaatt tcacacagga aacagctatg accatgatta cgaatttggc      6300
caagtcggcc tctaatacga ctcactatag ggagctc                               6337
```

<210> SEQ ID NO 59
<211> LENGTH: 1146
<212> TYPE: DNA
<213> ORGANISM: Zea mays

<400> SEQUENCE: 59

```
atgaccgaga aggagcggga gaagcaggag cagctcgccc gagctaccgg tggcgccgcg        60
atgcagcggt cgccggtgga gaagcctccg ttcactctgg gtcagatcaa gaaggccatc       120
ccgccacact gcttcgagcg ctcggtgctc aagtccttct cgtacgtggt ccacgacctg       180
gtgatcgccg cggcgctcct ctacttcgcg ctggccatca taccggcgct cccaagcccg       240
ctccgctacg ccgcctggcc gctgtactgg atcgcgcagg ggtgcgtgtg caccggcgtg       300
tgggtcatcg cgcacgagtg cggccaccac gccttctcgg actactcgct cctggacgac       360
gtggtcggcc tggtgctgca ctcgtcgctc atggtgccct acttctcgtg gaagtacagc       420
caccggcgcc accactccaa cacggggtcc ctggagcgcg acgaggtgtt cgtgcccaag       480
aagaaggagg cgctgccgtg gtacaccccg tacgtgtaca caacccggt cggccgggtg       540 gtgcacatcg tggtgcagct caccctcggg tggccgctgt acctggcgac caacgcgtcg       600
gggcggccgt acccgcgctt cgcctgccac ttcgaccct acggccccat ctacaacgac       660
cgggagcgcg cccagatctt cgtctcggac gccggcgtcg tggccgtggc gttcgggctg       720
tacaagctgg cggcggcgtt cggggtctgg tgggtggtgc gcgtgtacgc cgtgccgctg       780
ctgatcgtga acgcgtggct ggtgctcatc acctacctgc agcacaccca cccgtcgctc       840
ccccactacg actcgagcga gtgggactgg ctgcgcggcg cgctggccac catggaccgc       900
gactacggca tcctcaaccg cgtgttccac aacatcacgg acacgcacgt cgcgcaccac       960
ctcttctcca ccatgccgca ctaccacgcc atggaggcca ccaaggcgat caggcccatc      1020
ctcggcgact actaccactt cgacccgacc cctgtcgcca aggcgacctg gcgcgaggcc      1080
ggggaatgca tctacgtcga gcccgaggac cgcaagggcg tcttctggta caacaagaag      1140
ttctag                                                                1146
```

METHOD FOR IMPROVING THE CARCASS QUALITY OF AN ANIMAL

This application claims the benefit of Provisional application Ser. No. 60/088,987, filed Jun. 11, 1998.

FIELD OF THE INVENTION

The invention relates to the preparation and use of nucleic acid fragments comprising all or substantially all of a corn oleosin promoter, a stearoyl-ACP desaturase and a delta-12 desaturase which can be used individually or in combination to modify the lipid profile of corn. Chimeric genes comprising such nucleic acid fragments and suitable regulatory sequences can be used to create transgenic corn plants having altered lipid profiles.

BACKGROUND OF THE INVENTION

Plant lipids have a variety of industrial and nutritional uses and are central to plant membrane function and climatic adaptation. These lipids represent a vast array of chemical structures, and these structures determine the physiological and industrial properties of the lipid. Many of these structures result either directly or indirectly from metabolic processes that alter the degree of unsaturation of the lipid. Different metabolic regimes in different plants produce these altered lipids, and either domestication of exotic plant species or modification of agronomically adapted species is usually required to produce economically large amounts of the desired lipid.

Plant lipids find their major use as edible oils in the form of triacylglycerols. The specific performance and health attributes of edible oils are determined largely by their fatty acid composition. Most vegetable oils derived from commercial plant varieties are composed primarily of palmitic (16:0), stearic (18:0), oleic (18:1), linoleic (18:2) and linolenic (18:3) acids. Palmitic and stearic acids are, respectively, 16- and 18-carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids. The relative amounts of saturated and unsaturated fatty acids in commonly used, edible vegetable oils are summarized below (Table 1):

TABLE 1

Percentages of Saturated and Unsaturated Fatty Acids in the Oils of Selected Oil Crops

|  | Saturated | Mono-unsaturated | Poly-unsaturated |
| --- | --- | --- | --- |
| Canola | 6% | 58% | 36% |
| Soybean | 15% | 24% | 61% |
| Corn | 13% | 25% | 62% |
| Peanut | 18% | 48% | 34% |
| Safflower | 9% | 13% | 78% |
| Sunflower | 9% | 41% | 51% |
| Cotton | 30% | 19% | 51% |

Corn oil is comprised primarily of even-numbered carbon chain fatty acids. The distribution of fatty acids in typical corn oil is approximately 12% palmitic acid (16:0), 2% stearic acid (18:0), 25% oleic acid (18:1), 60% linoleic acid (18:2), and 1% linolenic acid (18:3). Palmitic and stearic acids are referred to as saturated fatty acids because their carbon chains contains only single bonds and the carbon chain is "saturated" with hydrogen atoms. Oleic, linoleic, and linolenic acids contain one, two, and three double bonds respectively, and are referred to as unsaturated fatty acids. Fatty acids in corn oil nearly always occur esterified to the hydroxyl groups of glycerol, thus forming triglycerides. Approximately 99% of refined corn oil is made up of triglycerides ("Corn Oil", Corn Refiners Association, Inc., 1001 Connecticut Ave., N.W., Washington, D.C. 20036, 1986, 24 pp.).

Many recent research efforts have examined the role that saturated and unsaturated fatty acids play in reducing the risk of coronary heart disease. In the past, it was believed that mono-unsaturates, in contrast to saturates and poly-unsaturates, had no effect on serum cholesterol and coronary heart disease risk. Several recent human clinical studies suggest that diets high in mono-unsaturated fat and low in saturated fat may reduce the "bad" (low-density lipoprotein) cholesterol while maintaining the "good" (high-density lipoprotein) cholesterol (Mattson et al. (1985) *Journal of Lipid Research* 26:194–202).

A vegetable oil low in total saturates and high in mono-unsaturates would provide significant health benefits to consumers as well as economic benefits to oil processors. As an example, canola oil is considered a very healthy oil. However, in use, the high level of poly-unsaturated fatty acids in canola oil renders the oil unstable, easily oxidized, and susceptible to development of disagreeable odors and flavors (Gailliard (1980) in *The Biochemistry of Plants* Vol. 4, pp. 85–116, Stumpf, P. K., ed., Academic Press, New York). The levels of poly-unsaturates may be reduced by hydrogenation, but the expense of this process and the concomitant production of nutritionally questionable trans isomers of the remaining unsaturated fatty acids reduces the overall desirability of the hydrogenated oil (Mensink et al. (1990) *N. Eng. J. Med.* N323: 439–445).

When exposed to air, unsaturated fatty acids are subject to oxidation which causes the oil to have a rancid odor. Oxidation is accelerated by high temperatures, such as in frying conditions. The rate of oxidation is enhanced in the cases of oils containing greater degrees of unsaturation. Thus, linoleic acid with two double bonds is more unstable than oleic acid which has only one double bond. Oxidation reduces the shelf life of products containing corn oil because of that oil's high proportion of linoleic acid. Corn oil and products containing corn oil are often packaged under nitrogen in special packaging materials such as plastic or laminated foil, or are stored under refrigeration to extend their shelf life. These extra measures to reduce oxidation and subsequent rancidity add considerable cost to products containing corn oil.

Another measure to reduce the effects of oxidation on corn oil is to chemically hydrogenate the oil. This commercially important process by which hydrogen is added to double bonds of unsaturated fatty acids changes the physical properties of the oil and extends the shelf life of products containing corn oil. Hydrogenated vegetable oils are used to make margarine, salad dressings, cooking oils, and shortenings, for example. Approximately half a billion pounds, or roughly 40–50% of corn oil produced in the U.S. is used for cooking and for salad oils (Fitch, B., (1985) *JAOCS*, Vol. 62, no. 11, pp. 1524–31). Production of a more stable oil by genetic means would clearly have value by reducing or eliminating the time and input costs of chemical hydrogenation.

In addition to the economic factors associated with chemical hydrogenation of corn oil, there are human health factors that favor the production of a natural high oleic oil. During the hydrogenation process, double bonds in fatty acids are completely hydrogenated or are converted from the cis configuration to the trans configuration. Cis double bonds cause a fatty acid molecule to "bend," which impairs crystallization and keeps the oil liquid at room temperature. During hydrogenation, cis bonds are straightened into the trans configuration, causing the oil to harden at room temperature. Recent studies on the effect of dietary trans fatty acids on cholesterol levels show that the trans isomer of oleic acid raises blood cholesterol levels at least as much as saturated fatty acids, which have been know for some time to raise cholesterol in humans (Mensink, R. P. and B. K. Katan, (1990) N. Engl. J. Med., 323:439–45). Furthermore, these studies show that the undesirable low density lipoprotein level increases and the desirable high density lipoprotein level decreases in response to diets high in trans fatty acids. Large amounts of trans fatty acids are found in margarines, shortenings, and oils used for frying; the most abundant trans fatty acid in the human diet is the trans isomer of oleic acid, elaidic acid.

While oils with low levels of saturated fatty acids are desirable from the standpoint of providing a healthy diet, fats that are solid at room temperature are required in some foods because of their functional properties. Such applications include the production of non-dairy margarines and spreads, and various applications in confections and in baking. Many animal and dairy fats provide the necessary physical properties, but they also contain both cholesterol and cholesterogenic medium-chain fatty acids. An ideal triglyceride for solid fat applications should contain a predominance of the very high melting, long chain fatty acid, stearic acid, and a balance of mono-unsaturated fatty acid with very little polyunsaturated fat. Natural plant solid fat fractions typically have a triacylglyceride structure with saturated fatty acids occupying the sn-1 and sn-3 positions of the triglycerides and an unsaturated fatty acid at the sn-2 position. This overall fatty acid composition and triglyceride structure confers an optimal solid fat crystal structure and a maximum melting point with minimal saturated fatty acid content.

The natural fat prototype for this high melting temperature vegetable fat is cocoa butter. More than 2 billion pounds of cocoa butter, the most expensive commodity edible oil, are produced worldwide. The U.S. imports several hundred million dollars worth of cocoa butter annually. High and volatile prices together with the uncertain supply of cocoa butter have encouraged the development of cocoa butter substitutes. The fatty acid composition of cocoa butter is 26% palmitic, 34% stearic, 35% oleic and 3% linoleic acids. About 72% of cocoa 'butter's triglycerides have the structure in which saturated fatty acids occupy positions 1 and 3 and oleic acid occupies position 2. Cocoa 'butter's unique fatty acid composition and distribution on the triglyceride molecule confer on it properties eminently suitable for confectionery end-uses: it is brittle below 27° C. and depending on its crystalline state, melts sharply at 25°–30° C. or 35°–36° C. Consequently, it is hard and non-greasy at ordinary temperatures and melts very sharply in the mouth. It is also extremely resistant to rancidity. For these reasons, producing corn oil with increased levels of stearic acid, especially in corn lines containing higher-than-normal levels of palmitic acid, and reduced levels of unsaturated fatty acids is expected to produce a cocoa butter substitute in corn. This will provide additional value to oil and food processors as well as reduce the foreign import of certain tropical oils.

The human diet could also be improved by reducing saturated fat intake. Much of the saturated fat in the human diet comes from meat products. Poultry and swine diets often contain animal fat, which is high in saturated fatty acids, as an energy source. Non-ruminant animals such as these are very susceptible to tissue fatty acid alteration through dietary modification (M. F. Miller, et al. (1990) J. Anim. Sci., 68:1624–31). A large portion of animal feed rations is made up of corn, which typically contains only about 4% oil. By replacing some or all of the supplemental animal fat in a feed ration with the oil present in high oil corn varieties, which contain up to 10% oil, it will be possible to produce meat products having a lower content of saturated fats. Feeding trials in which swine were fed diets high in oleic acid show that the amount of oleic acid deposited in adipose tissue can be raised substantially without adversely influencing the quality of the meat (M. F. Miller, et al.; L. C. St. John et al. (1987) J. Anim. Sci., 64:1441–47). The degree of saturation of the fatty acids comprising an oil determines whether it is liquid or solid. In these studies, the animal diets high in oleic acid led to meat quality that was acceptable to the meat processing industry because of the low level of polyunsaturated fatty acids.

Only recently have serious efforts been made to improve the quality of corn oil through plant breeding, especially following mutagenesis, and a wide range of fatty acid composition has been discovered in experimental lines. These findings (as well as those with other oilcrops) suggest that the fatty acid composition of corn oil can be significantly modified without affecting the agronomic performance of a corn plant.

There are serious limitations to using mutagenesis to alter fatty acid composition. It is unlikely to discover mutations that a) result in a dominant ("gain-of-function") phenotype, b) are in genes that are essential for plant growth, and c) are in an enzyme that is not rate-limiting and that is encoded by more than one gene. Even when some of the desired mutations are available in mutant corn lines, their introgression into elite lines by traditional breeding techniques will be slow and expensive, since the desired oil compositions in corn are most likely to involve several recessive genes.

Recent molecular and cellular biology techniques offer the potential for overcoming some of the limitations of the mutagenesis approach, including the need for extensive breeding. Some of the particularly useful technologies are seed-specific expression of foreign genes in transgenic plants [see Goldberg et al. (1989) Cell 56:149–160], and the use of antisense RNA to inhibit plant target genes in a dominant and tissue-specific manner [see van der Krol et al. (1988) Gene 72:45–50]. Other advances include the transfer of foreign genes into elite commercial varieties of commercial oilcrops, such as soybean [Chee et al.

Plant Physiol. 91:1212–1218; Christou et al. (1989) Proc. Natl. Acad. Sci. U.S.A. 86:7500–7504; Hinchee et al. (1988) Bio/Technology 6:915–922; EPO publication 0 301 749 A2], rapeseed [De Block et al. (1989) Plant Physiol. 91:694–701], and sunflower [Everett et al. (1987) Bio/Technology 5:1201–1204], and the use of genes as restriction fragment length polymorphism (RFLP) markers in a breeding program, which makes introgression of recessive traits into elite lines rapid and less expensive [Tanksley et al. (1991) Bio/Technology 7:257–264]. However, application of each of these technologies requires identification and isolation of commercially-important genes.

WO 91/13972, published Sep. 19, 1991, describes desaturase enzymes relevant to fatty acid synthesis in plants, especially delta-9 desaturases.

U.S. Pat. No. 5,443,974, issued to Hitz et al. on Aug. 22, 1995, describes the preparation and use of nucleic acid fragments encoding soybean seed stearoyl-ACP desaturase enzymes or its precursor to modify plant oil composition.

WO 94/11516, published May 26, 1994, describes genes for microsomal delta-12 desaturases and related enzymes from plants. The cloning of a corn (Zea mays) cDNA encoding seed microsomal delta-12 fatty acid desaturase is described. The discussion of that citation is hereby incorporated by reference.

Oil biosynthesis in plants has been fairly well-studied [see Harwood (1989) in *Critical Reviews in Plant Sciences* Vol. 8(1): 1–43]. The biosynthesis of palmitic, stearic and oleic acids occur in the plastids by the interplay of three key enzymes of the "ACP track": palmitoyl-ACP elongase, stearoyl-ACP desaturase and acyl-ACP thioesterase. Stearoyl-ACP desaturase introduces the first double bond on stearoyl-ACP to form oleoyl-ACP. It is pivotal in determining the degree of unsaturation in vegetable oils. Because of its key position in fatty acid biosynthesis it is expected to be an important regulatory step. While the 'enzyme's natural substrate is stearoyl-ACP, it has been shown that it can, like its counterpart in yeast and mammalian cells, desaturate stearoyl-CoA, albeit poorly [McKeon et al. (1982) J. Biol. Chem. 257:12141–12147]. The fatty acids synthesized in the plastid are exported as acyl-CoA to the cytoplasm. At least three different glycerol acylating enzymes (glycerol-3-P acyltransferase, 1-acyl-glycerol-3-P acyltransferase and diacylglycerol acyltransferase) incorporate the acyl moieties from the cytoplasm into triglycerides during oil biosynthesis. These acyltransferases show a strong, but not absolute, preference for incorporating saturated fatty acids at the sn-1 and sn-3 positions and monounsaturated fatty acid at the sn-2 of the triglyceride. Thus, altering the fatty acid composition of the acyl pool will drive a corresponding change in the fatty acid composition of the oil due to the effescts of mass action. Furthermore, there is experimental evidence that, because of this specificity, and given the correct composition of fatty acids, plants can produce oils suitable as cocoa butter substitutes [Bafor et al. (1990) *JAOCS* 67:217–225].

Based on the above discussion, one approach to altering the levels of stearic and oleic acids in vegetable oils is by altering their levels in the cytoplasmic acyl-CoA pool used for oil biosynthesis. There are two ways of doing this genetically. One of these ways is to alter the biosynthesis of stearic and oleic acids in the plastid by modulating the levels of stearoyl-ACP desaturase in seeds through either overexpression or antisense inhibition of its gene. Another is converting stearoyl-CoA to oleoyl-CoA in the cytoplasm through the expression of the stearoyl-ACP desaturase in the cytoplasm.

In order to use antisense or sense inhibition of stearoyl-ACP desaturase in the seed, it is essential to isolate the gene(s) or cDNA(s) encoding the target enzyme(s) in the seed, since either of these mechanisms of inhibition requires a high-degree of complementarity between the antisense RNA (see Stam et al. (1997) *Annals of Botany* 79:3–12) and the target gene. Such high levels of sequence complementarity or identity is not expected in stearoyl-ACP desaturase genes from heterologous species.

The purification and nucleotide sequences of mammalian microsomal stearoyl-CoA desaturases have been published [Thiede et al. (1986) *J. Biol. Chem.* 262:13230–13235; Ntambi et al. (1988) *J. Biol. Chem.* 263:17291–17300 and Kaestner et al. (1989) *J. Biol. Chem.* 264:14755–14761]. However, the plant enzyme differs from them in being soluble, in utilizing a different electron donor, and in its substrate-specificities. The purification and the nucleotide sequences for animal enzymes do not teach how to purify a plant enzyme or isolate a plant gene. The purification of stearoyl-ACP desaturase was reported from safflower seeds [McKeon et al. (1982) J. Biol. Chem. 257:12141–12147] and from soybean (U.S. Pat. No. 5,443,974).

The rat liver stearoyl-CoA desaturase protein has been expressed in *E. coli* [Strittmatter et al. (1988) J. Biol. Chem. 263:2532–2535] but, as mentioned above, its substrate specificity and electron donors are quite distinct from that of the plant.

Plant stearoyl-ACP desaturase cDNAs have been cloned from numerous species including safflower [Thompson et al. (1991) Proc. Natl. Acad. Sci. 88:2578], castor [Shanklin and Somerville (1991) Proc. Natl. Acad. Sci. 88:2510–2514], and cucumber [Shanklin et al. (1991) Plant Physiol. 97:467–468]. Kutzon et al. [(1992) Proc. Natl. Acad. Sci. 89:2624–2648] have reported that rapeseed stearoyl-ACP desaturase when expressed in *Brassica rapa* and *B. napa* in an antisense orientation can result in increase in 18:0 level in transgenic seeds.

Manipulation of stearate levels has been described (Knutzon, D. S. et al., (1992) *Proc. Natl. Acad. Sci. USA* 89(7): 2624–2628). It is possible to elevate the level of stearate seed oils by underexpression of stearoyl-ACP desaturase, the enzyme responsible for introducing the first double bond into 18 carbon fatty acids in plants. Seeds from both *B. campestris* and *B. napus* plants produced by antisense expression of a cDNA encoding the *B. campestris* stearoyl-ACP desaturase using a seed specific promoter region produced oils high in stearic acid, but also contained elevated levels of linolenic acid (18:3) when compared to unmodified plants from the same species. Elevated levels of stearic acid have been obtained in soybean by a similar underexpression of stearoyl-ACP desaturase (U.S. Pat. No. 5,443,974) and in canola by overexpression of an acyl-ACP thioesterase (U.S. Pat. No. 5,530,186). Mutation breeding has also produced soybean lines with elevated levels of stearic acid in their seed oils (Graef, G. L. et al., (1985) *JAOCS* 62:773–775; Hammond, E. G. and W. R. Fehr, (1983) *Crop Sci.* 23:192–193).

Poly-unsaturated fatty acids contribute to the low melting point of liquid vegetable oils. In high saturate oils their presence is a detriment in that they decrease melting point, and therefore even higher levels of undesirable saturated fatty acid are required to achieve a plastic fat at room temperature. Additionally, when used in baking and confectionery applications, high levels of poly-unsaturates leads to oxidative instability as described above for liquid oils. Thus for maximum utility a high saturate fat produced in corn should contain saturated fatty acids, mono-unsaturated fatty acid and as little poly-unsaturated fatty acid as possible. Gene combinations discovered in this invention provide novel fatty acid profiles in corn which meet these criteria. Other combinations result in a lipid profile in which the oleic acid content is not less than 60% of the total oil content. Many of these combinations also utilize a novel corn oleosin promoter or an intron/exon region from the shrunken 1 gene, or both an oleosin promoter and an intron/exon region from the shrunken 1 gene.

Lipid reserves in corn seeds are synthesized and stored primarily in a specialized tissue of the embryo called the scutellum. These lipid reserves constitute up to 50% of the dry weight of the embryo at seed maturity. As in all seeds, the storage lipid in corn seeds is packaged into simple organelles called oil bodies. These small spherical organelles consist of a triacylglycerol core surrounded by a single layer of phospholipids embedded with proteins termed oleosins (Huang (1985) *Modern Methods of Plant Analysis* 1: 175–214; Stymme and Stobart (1987) *The Biochemistry of Plants* 10: 175–214; Yatsue and Jacks (1972) *Plant Physiol.* 49: 937–943; and Gurr (1980) *The Biochemistry of Plants* 4: 205–248).

At least two classes of oleosin isoforms have been identified in diverse species of plants (Tzen et al. (1990) *Plant Physiol.* 94: 1282–1289). These two classes are arbitrarily named as high (H) and low (L) molecular weight isoforms within a particular species. Members of one isoform from diverse species are understood to be structurally related based on demonstrations of shared immunochemical properties and possession of significant amino acid sequence identity, and they are clearly distinct from members of the other isoform (Hatzopoulos et al. (1990) *Plant Cell* 2: 457–467; Lee and Huang (1994) *Plant Mol. Biol.* 26(6): 1981–1987; Murphy et al. (1991) *Biochim. Biophys. Acta,* 1088: 86–94; Qu and Huang (1990) *J. Biol. Chem.* 265: 2238–2243).

There are three oleosin isoforms present in corn seeds. They are found in the approximately proportional amounts of 2:1:1. These isoforms are named OLE16, OLE 17, and OLE 18, corresponding to their apparent molecular weights which range from approximately 16 kDa to 18 kDa. OLE17 and OLE18 are closely related members of the H class, whereas OLE16 is a member of the L class (Lee and Huang, 1994). The genes encoding the three oleosins have been cloned and sequenced (Qu and Huang (1990) *J. Biol. Chem.* 265: 2238–2243; and Huang, personal communication). The genes are expressed only in tissues within the embryo (scutellum and embryonic axis) and the aleurone layer during seed development, and are positively regulated by the hormone abscissic acid (Vance and Huang (1988) *J. Biol. Chem.* 263: 1476–1491; Huang (1992) *Annu. Rev. Plant Physiol. Plant Mol. Biol.* 43: 177–200). The oleosins are highly expressed in the embryo, representing about 5–10% of the total scutellum protein or 2–8% of the total seed proteins.

Promoters from genes that display an embryo- and aleurone-specific ("embryo/aleurone") pattern of expression, such as the oleosin genes, would be attractive candidates for use in transgenic approaches to direct the expression of a gene encoding an oil-modifying enzyme (Qu and Huang (1990) *J. Biol. Chem.* 265: 2238–2243; and Huang (1992)) or other enzymes of interest for embryo-specific traits, especially in corn. Another potential candidate gene from which to isolate a corn embryo/aleurone-specific promoter is the maize globulin-1 gene (Belanger and Kriz, 1989, Plant Physiol. 91: 636–643). However, to date, there is no report that describes the expression, regulation, or use of such promoters in either transient expression assays or stably integrated transgenic corn plants.

SUMMARY OF THE INVENTION

This invention relates to an isolated nucleic acid fragment comprising a corn oleosin promoter wherein said promoter can be full length or partial and further wherein said promoter comprises a nucleotide sequence corresponding substantially to the nucleotide sequence in any of SEQ ID NOS:19 or 38–49 or said promoter comprises a fragment or subfragment that is substantially similar and functionally equivalent to any of the nucleotide sequences set forth in SEQ ID NOS:19 or 38–49.

In a second embodiment this invention concerns an isolated nucleic acid fragment encoding a corn delta-9 stearoyl-ACP desaturase corresponding substantially to a nucleotide sequence set forth in any of SEQ ID NOS:8 and 10 or any functionally equivalent subfragment thereof. Also included are chimeric genes comprising such fragments or subfragments thereof or the reverse complement of such fragment or subfragment which are operably linked to suitable regulatory sequences wherein expression of the chimeric gene results in an altered corn stearic acid phenotype.

In a third embodiment, this invention concerns an isolated nucleic acid fragment encoding a corn delta-12 desaturase corresponding substantially to the nucleotide sequence set forth in SEQ ID NO:2 or any functionally equivalent subfragment thereof as well as chimeric genes comprising such fragments or subfragments or the reverse complement of such fragment or subfragment which are operably linked to suitable regulatory sequences wherein expression of the chimeric gene results in an altered corn oleic acid phenotype.

In a fourth embodiment, this invention also concerns chimeric genes comprising an isolated nucleic acid fragment encoding a corn delta-9 stearoyl-ACP desaturase corresponding substantially to a nucleotide sequence set forth in any of SEQ ID NOS:8 and 10 or any functionally equivalent subfragment thereof or the reverse complement of such fragment or subfragment and an isolated nucleic acid fragment encoding a corn delta-12 desaturase or any functionally equivalent subfragment or the reverse complement of such fragment or subfragment which are operably linked and wherein expression of such combinations results in an altered corn oil phenotype.

Any of these chimeric genes may further comprise an isolated nucleic acid fragment comprising a corn oleosin promoter wherein said promoter can be full length or partial and further wherein said promoter comprises a nucleotide sequence corresponding substantially to the nucleotide sequence in any of SEQ ID NOS:19 or 38–49 or said promoter comprises a fragment or subfragment that is substantially similar and functionally equivalent to any of the nucleotide sequences set forth in SEQ ID NOS:19 or 38–49 or a shrunken 1 intron1/exon1, or both.

Also included in this invention are corn plants and plant parts thereof containing the various chimeric genes, seeds of such plants, oil obtained from the grain of such plants, animal feed derived from the processing of such grain, the use of the foregoing oil in food, animal feed, cooking oil or industrial applications, products made from the hydrogenation, fractionation, interesterification or hydrolysis of such oil and methods for improving the carcass quality of an animal.

BRIEF DESCRIPTION OF THE SEQUENCE LISTINGS AND FIGURES

The invention can be more fully understood from the following detailed description and the Figure and Sequence Descriptions which form a part of this application.

The sequence descriptions summarize the Sequences Listing attached hereto. The Sequence Listing contains one letter codes for nucleotide sequence characters and the three letter codes for amino acids as defined in the IUPAC-IUB standards described in *Nucleic Acids Research* 13:3021–3030 (1985) and in the *Biochemical Journal* 219 (No. 2):345–373

(1984), and the symbols and format used for all nucleotide and amino acid sequence data further comply with the rules governing nucleotide and/or amino acid sequence disclosures in patent applications as set forth in 37 C.F.R. §1.821–1.825 and WIPO Standard St.25.

SEQ ID NO:1 is a 1790 nucleotide sequence obtained from a corn cDNA which encodes a delta-12 desaturase enzyme (fad2-1). This sequence is also set forth in WO 94/11516.

SEQ ID NO:2 is a 1733 nucleotide sequence obtained from a corn cDNA which encodes a second delta-12 desaturase enzyme (fad2-2).

SEQ ID NO:3 is the translation product of the nucleotide sequence set forth in SEQ ID NO:2. The translation product is a polypeptide of 392 amino acids (translation frame: nucleotides 176–1351).

SEQ ID NO:4 is a 12,313 nucleotide sequence obtained from corn genomic DNA which comprises the region upstream of the fad2-2 coding region.

SEQ ID NO:5 is 2,907 nucleotide sequence obtained from corn genomic DNA which includes the fad2-1 intron.

SEQ ID NO:6 is a 18 base oligonucleotide primer used to amplify corn delta-9 desaturase via PCR.

SEQ ID NO:7 is a 17 base oligonucleotide primer used to amplify corn delta-9 desaturase via PCR.

SEQ ID NO:8 is the 1714 nucleotide sequence of a corn delta-9 desaturase cDNA as contained in plasmid pCD520.

SEQ ID NO:9 is the translation product of the nucleotide sequence set forth in SEQ ID NO:8. The translation product is a polypeptide of 392 amino acids (translation frame: nucleotides 134–1312).

SEQ ID NO:10 is a 1709 nucleotide sequence of a second corn delta-9 desaturase cDNA as contained in plasmid pBN408.

SEQ ID NO:11 is the translation product of the nucleotide sequence set forth in SEQ ID NO:10. The translation product is a polypeptide of 392 amino acids (translation frame: nucleotides 102–1280).

SEQ ID NO:12 is a 18 base oligonucleotide primer used to amplify a portion of corn fad2-1 via PCR.

SEQ ID NO:13 is a 17 base oligonucleotide primer used to amplify a portion of corn fad2-1 via PCR.

SEQ ID NOS:14 and 15 are 21 base oligonucleotide primers used to amplify a portion of the oleosin 16 kDa gene via PCR.

SEQ ID NOS:16 and 17 are 22 and 20, respectively, base oligonucleotide primers used to amplify a portion of the oleosin 18 kDa gene via PCR.

SEQ ID NO:18 is a 46 base oligonucleotide used as a hybridization probe to identify oleosin genes.

SEQ ID NO:19 is a 1714 nucleotide sequence of a corn oleosin 16 kDa promoter.

SEQ ID NO:20 is a 32 base oligonucleotide primer used to amplify deletion derivatives of the oleosin 16 kDa promoter via PCR.

SEQ ID NO:21 is a 33 base oligonucleotide primer used to amplify deletion derivatives of the oleosin 16 kDa promoter via PCR.

SEQ ID NO:22 is a 33 base oligonucleotide primer used to amplify deletion derivatives of the oleosin 16 kDa promoter via PCR.

SEQ ID NO:23 is a 32 base oligonucleotide primer used to amplify deletion derivatives of the oleosin 16 kDa promoter via PCR.

SEQ ID NO:24 is a 37 base oligonucleotide primer used to amplify deletion derivatives of the oleosin 16 kDa promoter via PCR.

SEQ ID NO:25 is a 32 base oligonucleotide primer used to amplify deletion derivatives of the oleosin 16 kDa promoter via PCR.

SEQ ID NO:26 is a 32 base oligonucleotide primer used to amplify deletion derivatives of the oleosin 16 kDa promoter via PCR.

SEQ ID NO:27 is a 33 base oligonucleotide primer used to amplify deletion derivatives of the oleosin 16 kDa promoter via PCR.

SEQ ID NO:28 is a 24 base oligonucleotide primer used to amplify deletion derivatives of the oleosin 16 kDa promoter via PCR.

SEQ ID NO:29 is a 19 base oligonucleotide primer used to amplify deletion derivatives of the oleosin 16 kDa promoter via PCR.

SEQ ID NO:30 is a 25 base oligonucleotide primer used to amplify the shrunken 1 intron1/exon1 via PCR.

SEQ ID NO:31 is a 25 base oligonucleotide primer used to amplify the shrunken 1 intron1/exon1 via PCR.

SEQ ID NOS:32 and 33 are 30 base oligonucleotides used as hybridization probes to identify clones containing the globulin-1 gene.

SEQ ID NOS:34 and 35 are 30 base oligonucleotide primers used to amplify the globulin-1 promoter.

SEQ ID NOS:36 and 37 are 36 and 39, respectively, base oligonucleotide primers used to amplify the globulin-1 promoter.

SEQ ID NO:38 is a 1.1 kb deletion derivative of the oleosin 16 kDa promoter.

SEQ ID NO:39 is a 0.9 kb deletion derivative of the oleosin 16 kDa promoter.

SEQ ID NO:40 is a 0.55 kb deletion derivative of the oleosin 16 kDa promoter.

SEQ ID NO:41 is a 0.95 kb deletion derivative of the oleosin 16 kDa promoter.

SEQ ID NO:42 is a 1.4 kb deletion derivative of the oleosin 16 kDa promoter.

SEQ ID NO:43 is a 1.0 kb deletion derivative of the oleosin 16 kDa promoter.

SEQ ID NO:44 is a 0.75 kb deletion derivative of the oleosin 16 kDa promoter.

SEQ ID NO:45 is a 0.4 kb deletion derivative of the oleosin 16 kDa promoter.

SEQ ID NO:46 is a 1.3 kb deletion derivative of the oleosin 16 kDa promoter.

SEQ ID NO:47 is a 0.8 kb deletion derivative of the oleosin 16 kDa promoter.

SEQ ID NO:48 is a 0.6 kb deletion derivative of the oleosin 16 kDa promoter.

SEQ ID NO:49 is a 0.3 kb deletion derivative of the oleosin 16 kDa promoter.

SEQ ID NOS:50 and 51 are 29 base oligonucleotide primers used to amplify the fad2-1 coding region via PCR.

SEQ ID NOS:52 and 53 are 31 and 30, respectively, base oligonucleotide primers used to amplify the delta-9 desaturase coding region via PCR.

SEQ ID NO:54 and 55 are 20 and 25, respectively, base oligonucleotide primers used to amplify portions of the fad2 genes via PCR.

SEQ ID NO:56 and 57 are 20 base oligonucleotide primers used to amplify the fad2-1 intron via PCR.

SEQ ID NO:58 is the complete nucleotide seqquece of plasmid pBN257. It contains an out-of-frame translation start for fad2-1 beginning at position 1978.

SEQ ID NO:59 is a truncated form of the fad2-1 gene from pBN257. The coding frame from pBN257 is represented by nucleotides 1991–3136 of SEQ ID NO:58.

FIG. 1 depicts Northern blot analyses of the developmental regulation of genes that are highly expressed in embryo and aleurone. Individual blots used the following as probes: FIG. 1A, fad2-1; FIG. 1B, delta-9 desaturase; FIGS. 1C and 1D, globulin-1, and FIGS. 1E and 1F, oleosin 16 kDa.

Figure 2A:
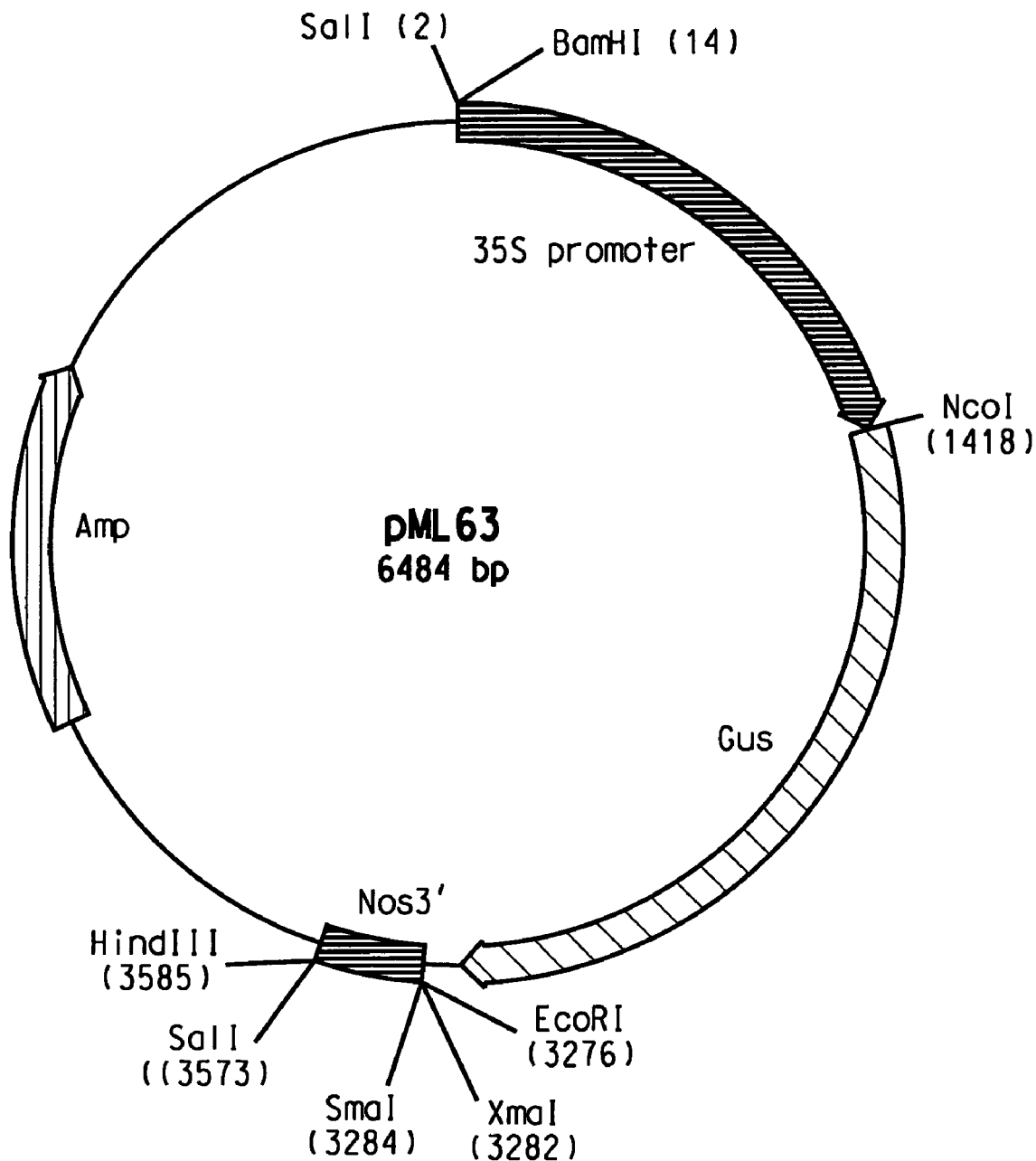
Figure 2B:
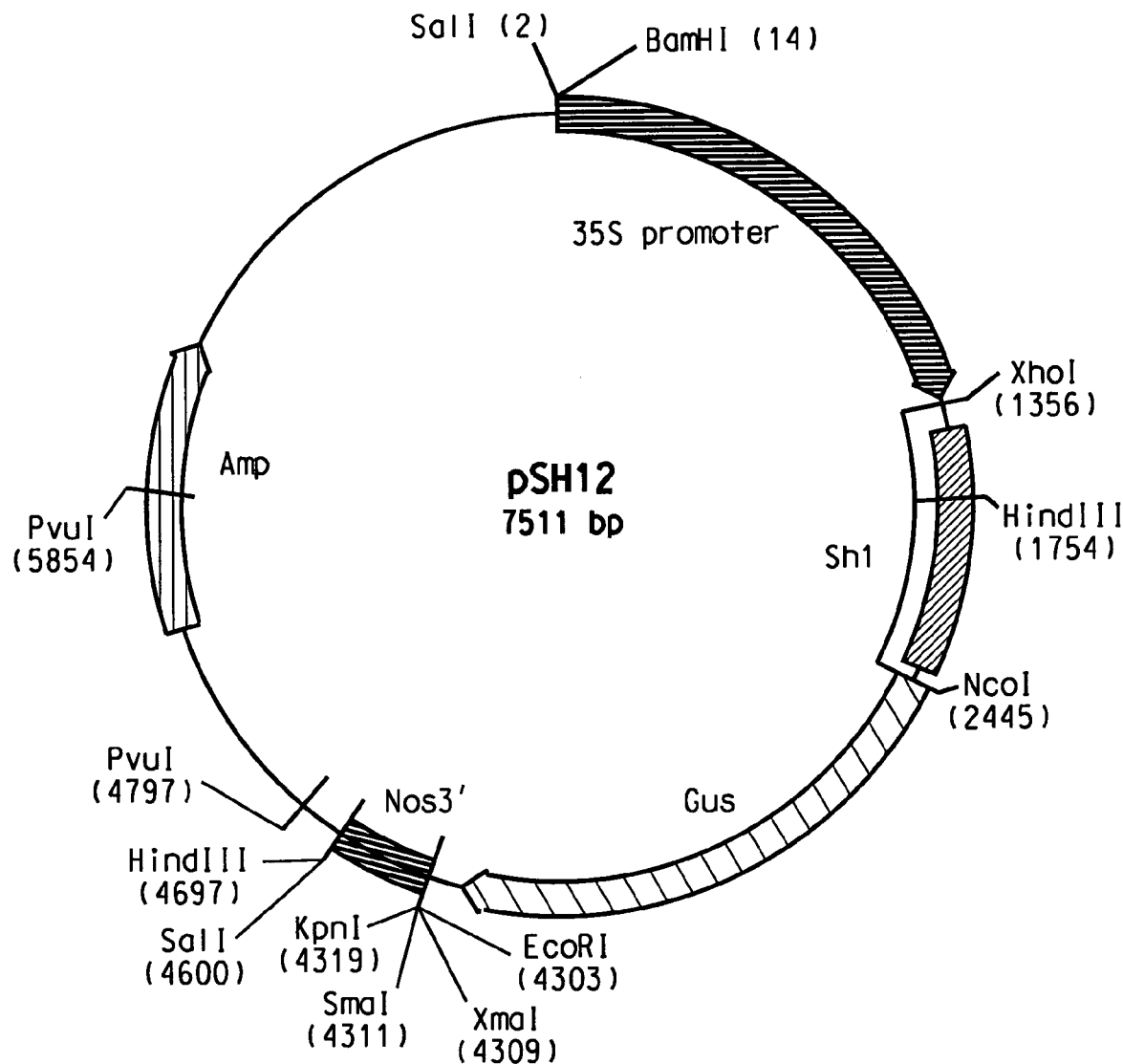
Figure 2C:
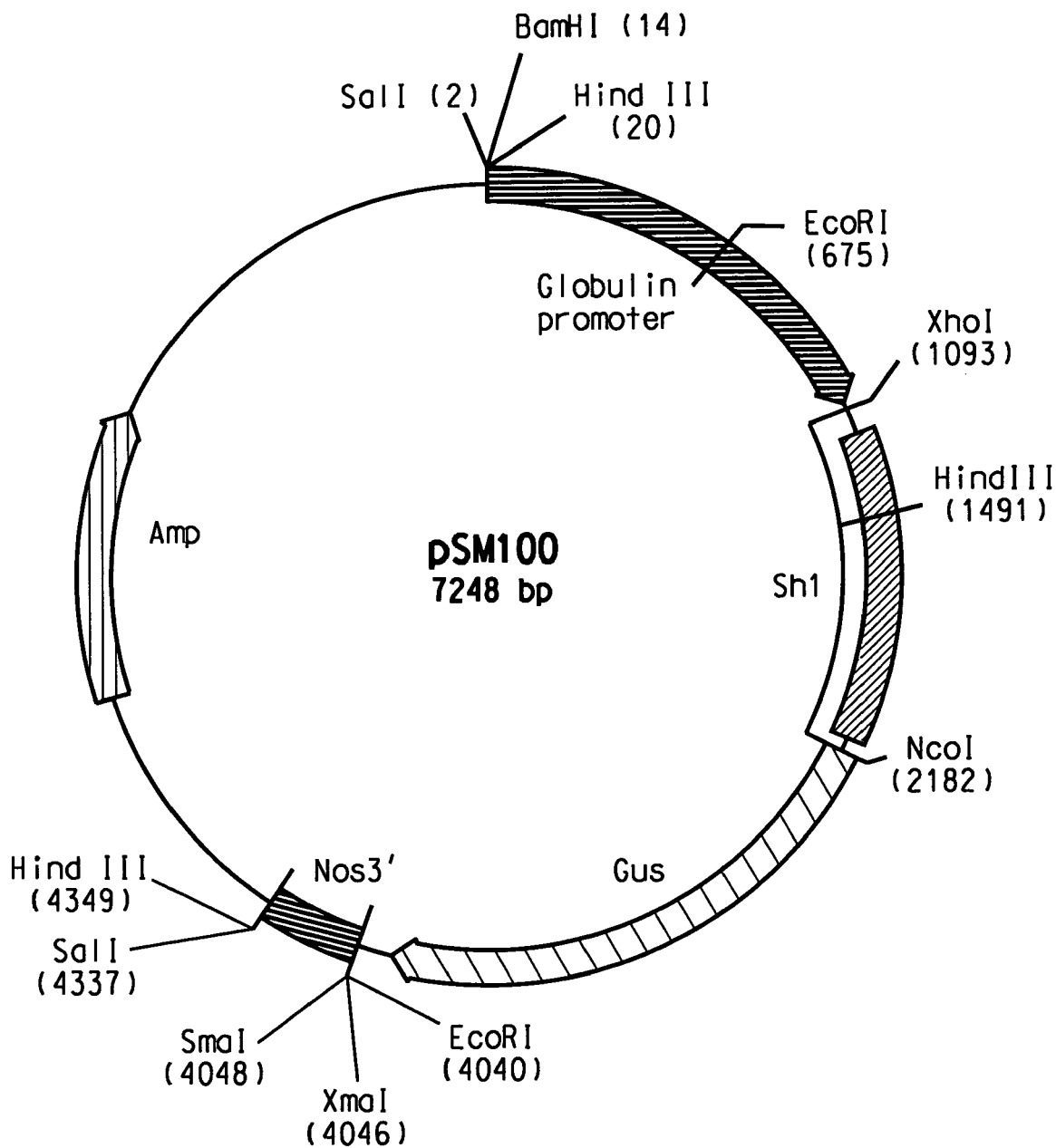
Figure 3A:
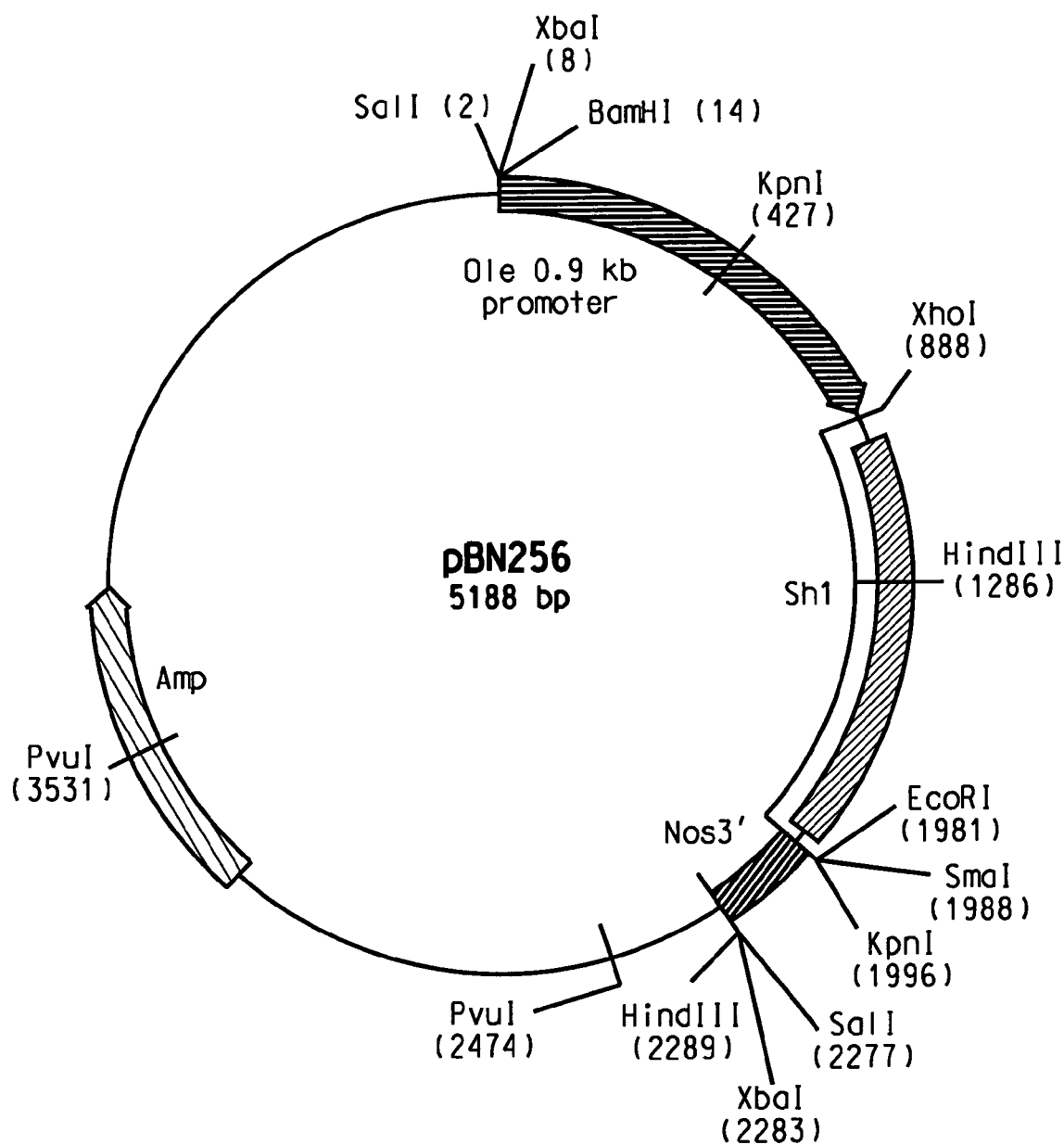
Figure 3B:
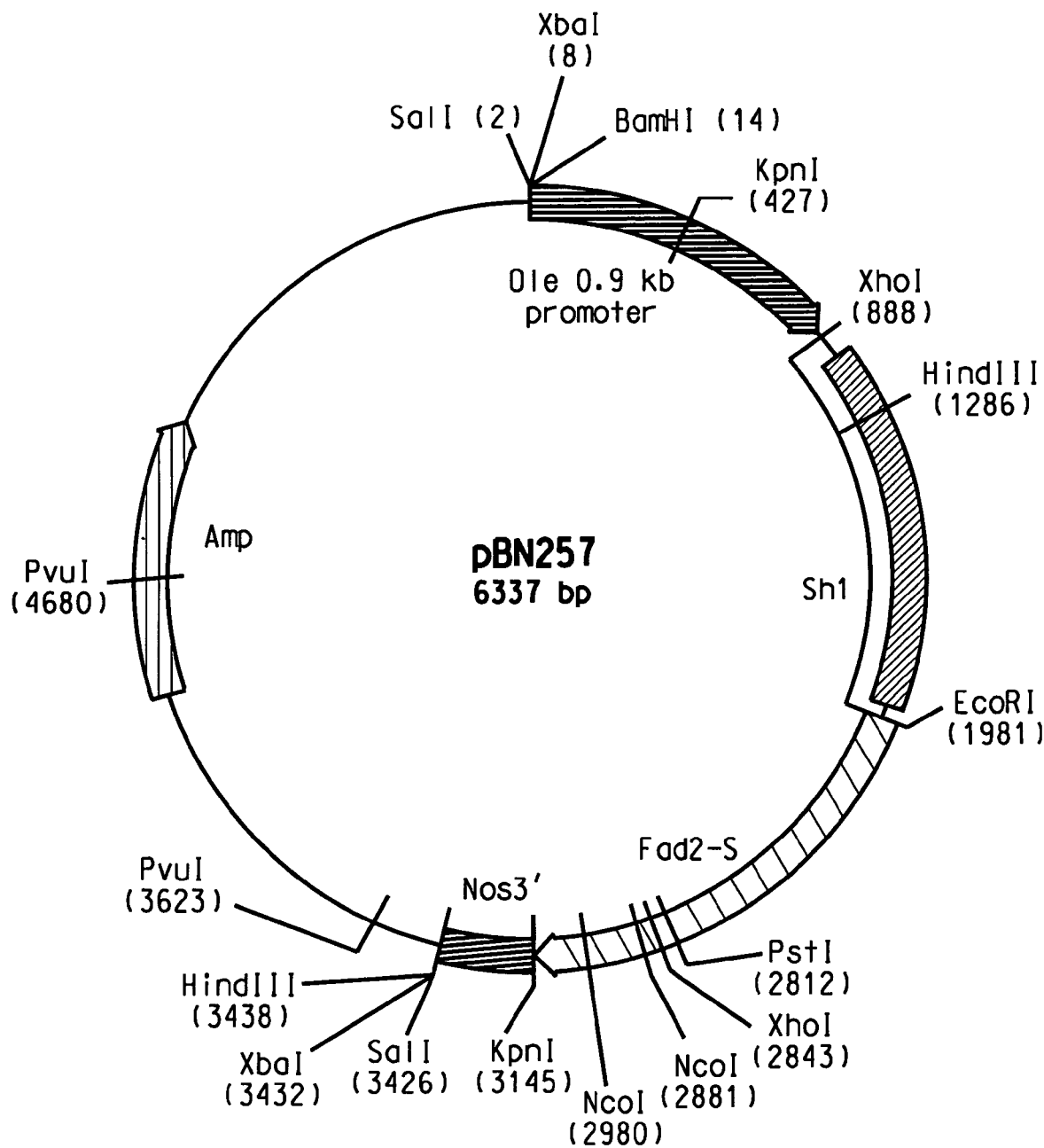
Figure 3C:
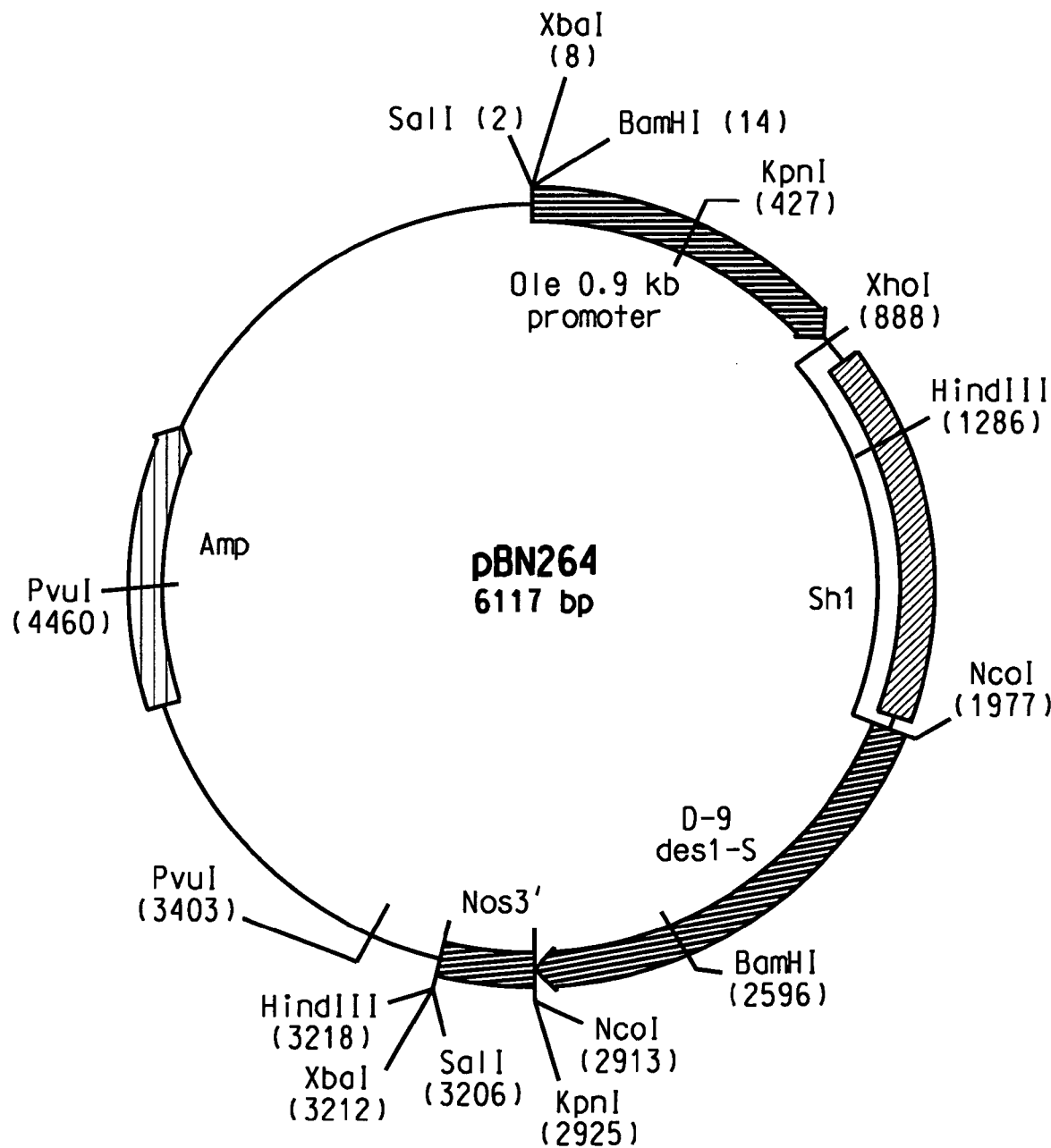
Figure 3D:
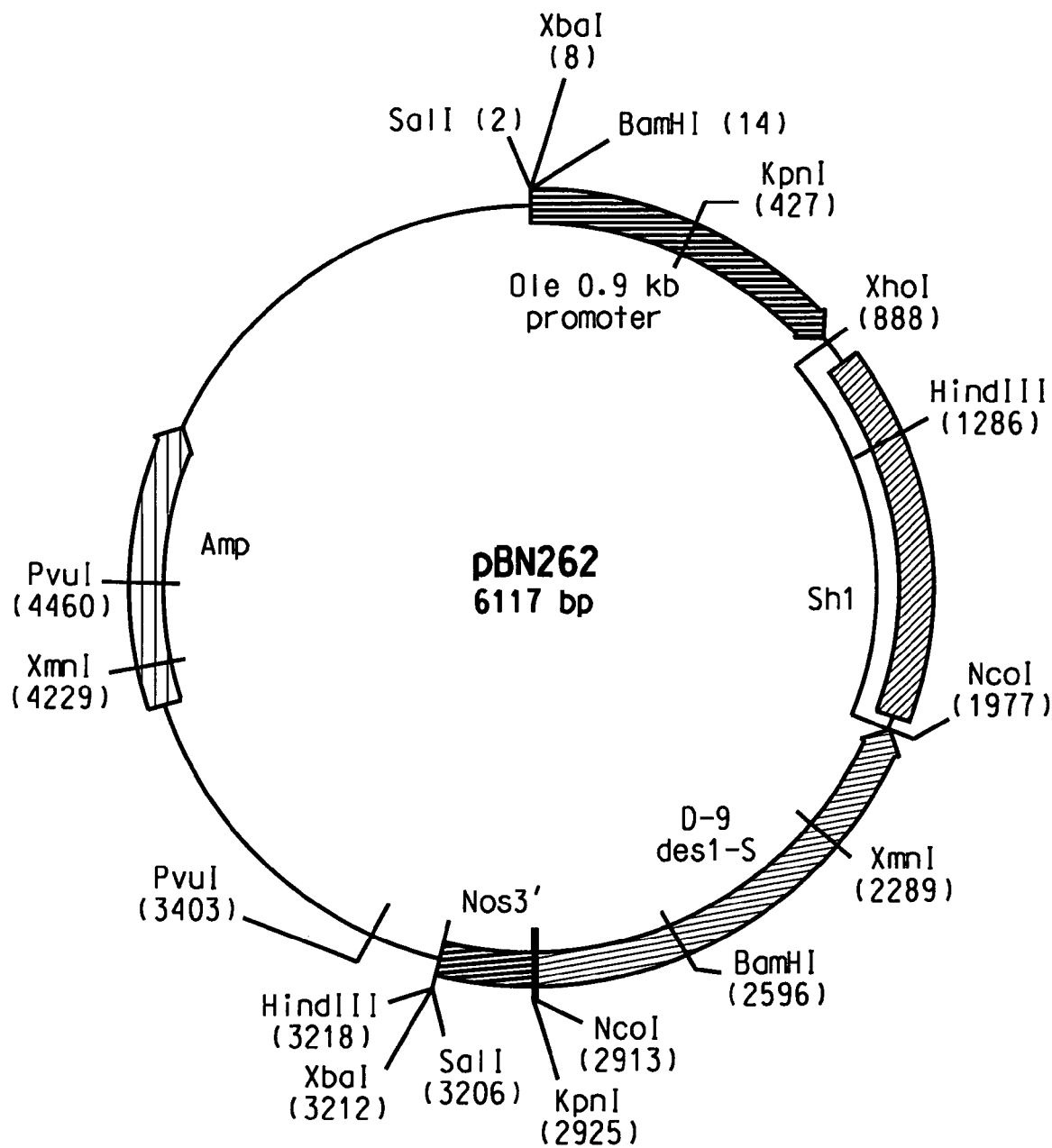
Figure 3E:
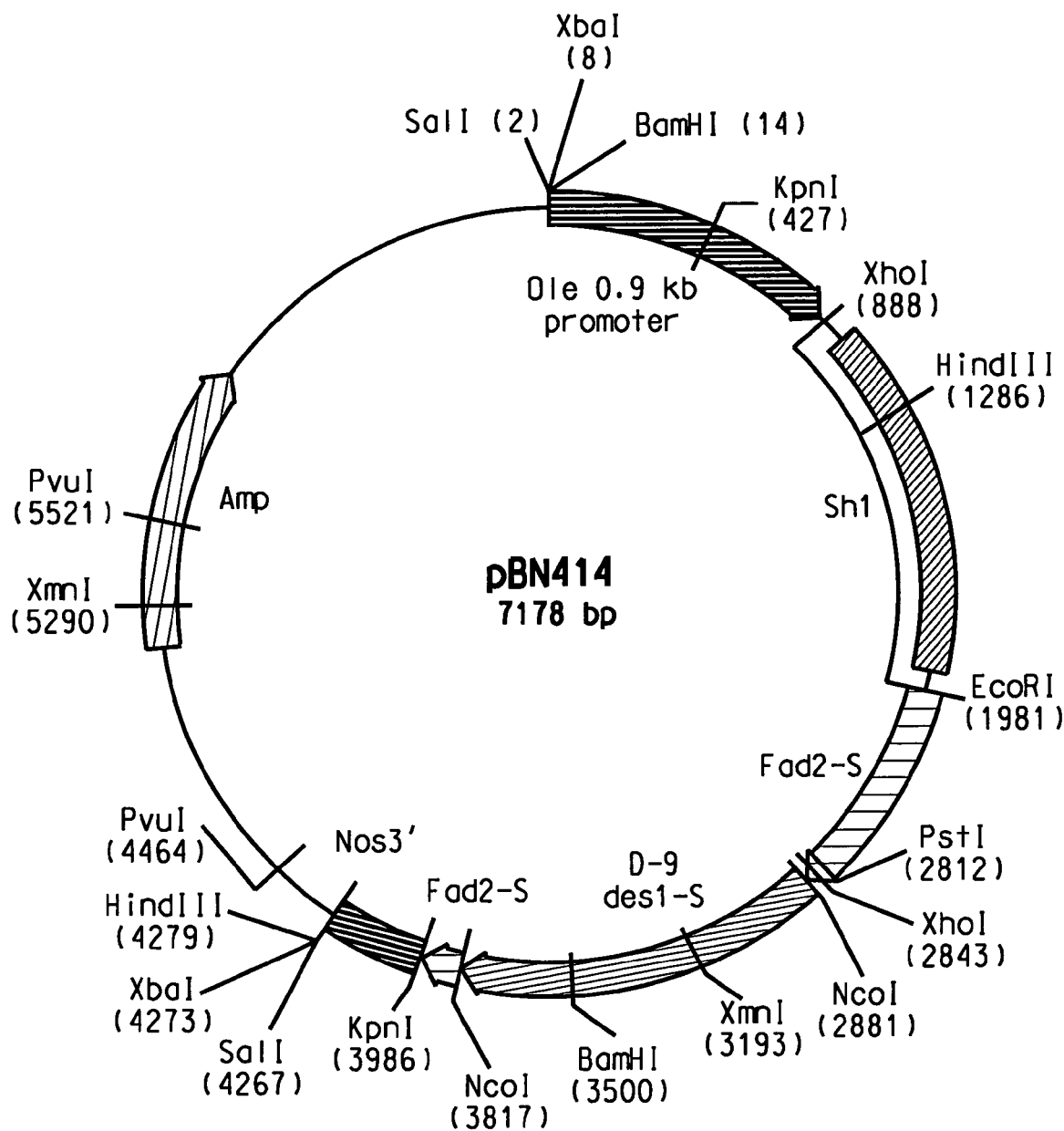
Figure 3F:
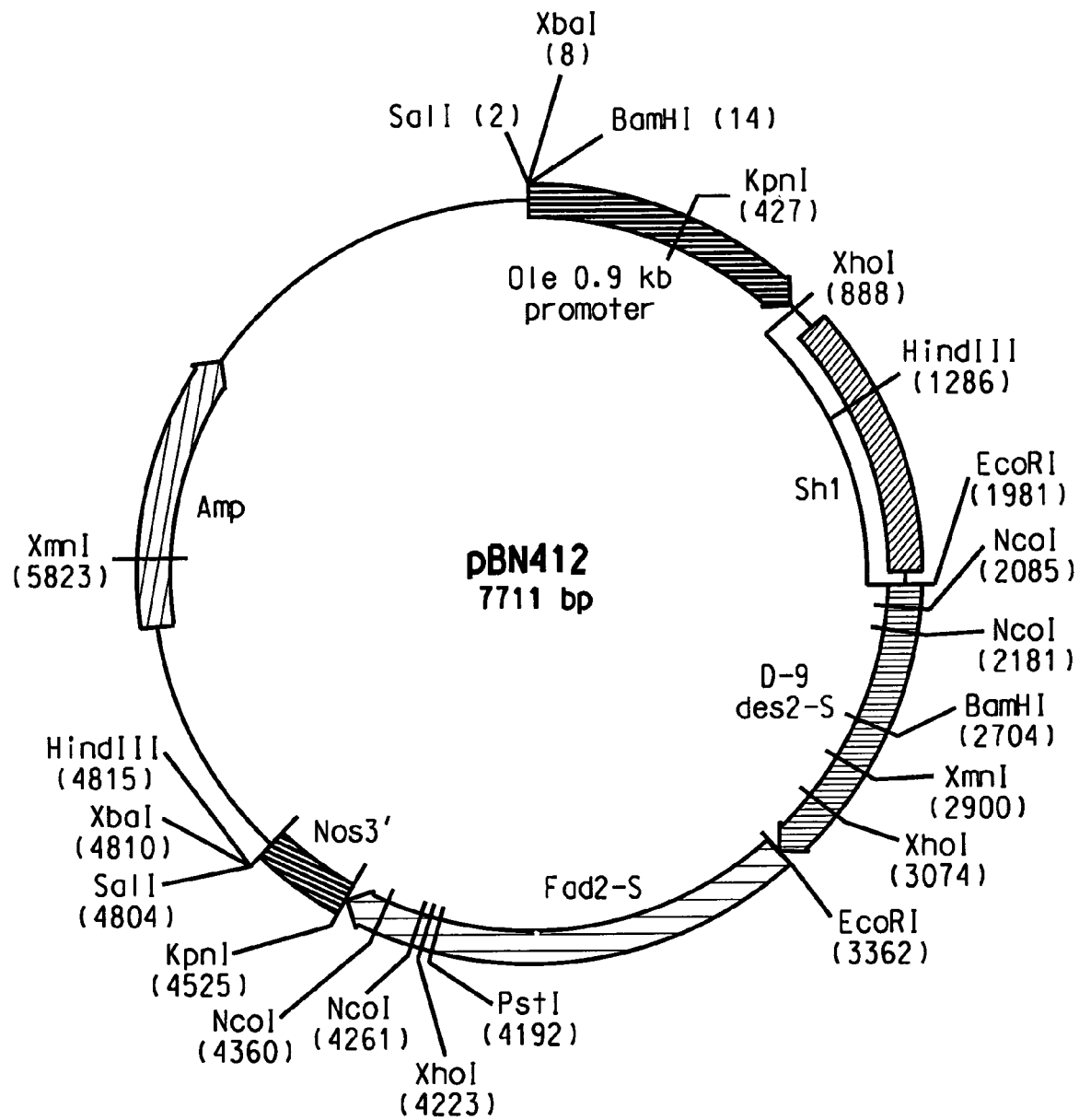
Figure 4A:
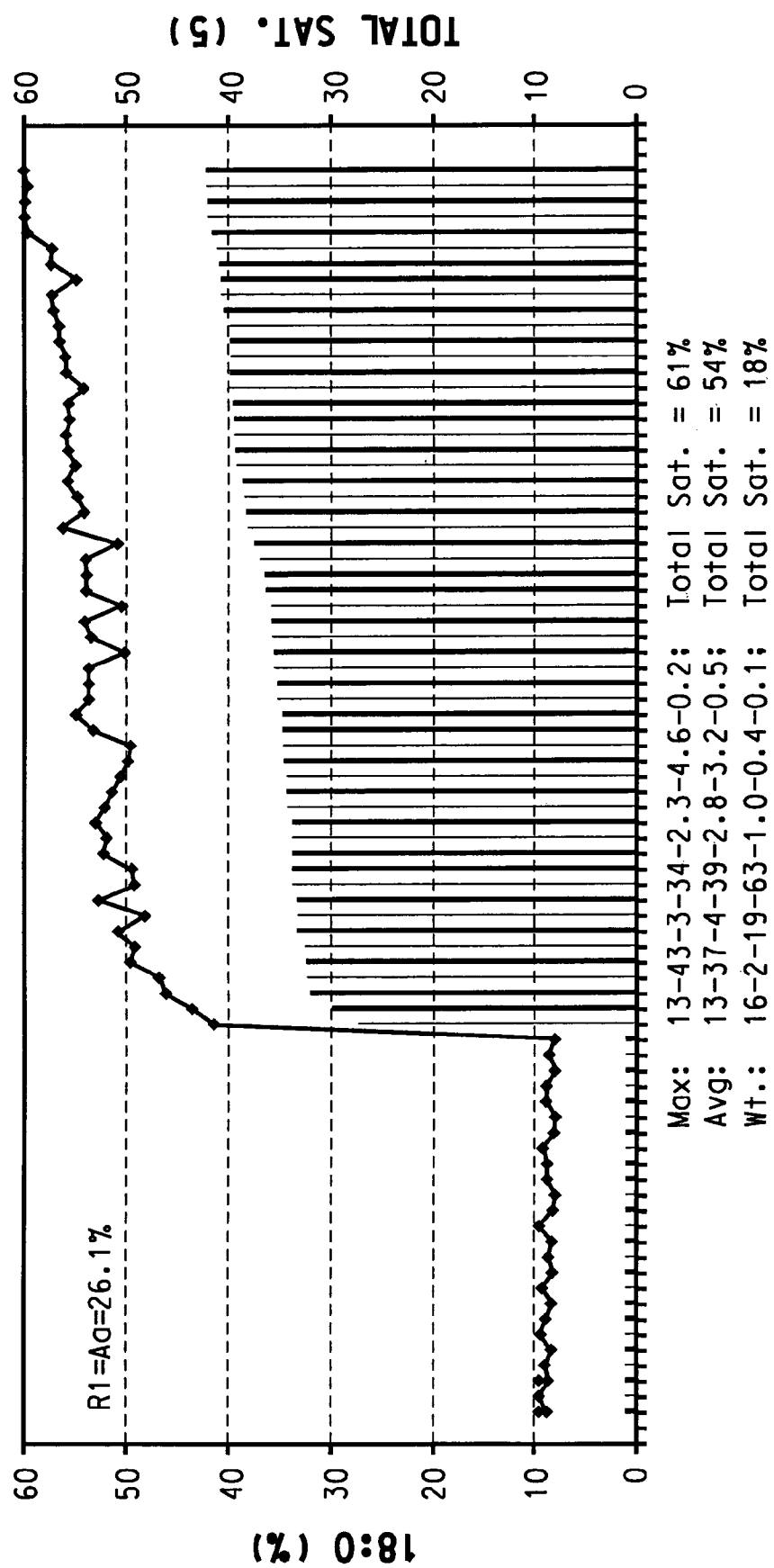
Figure 5:
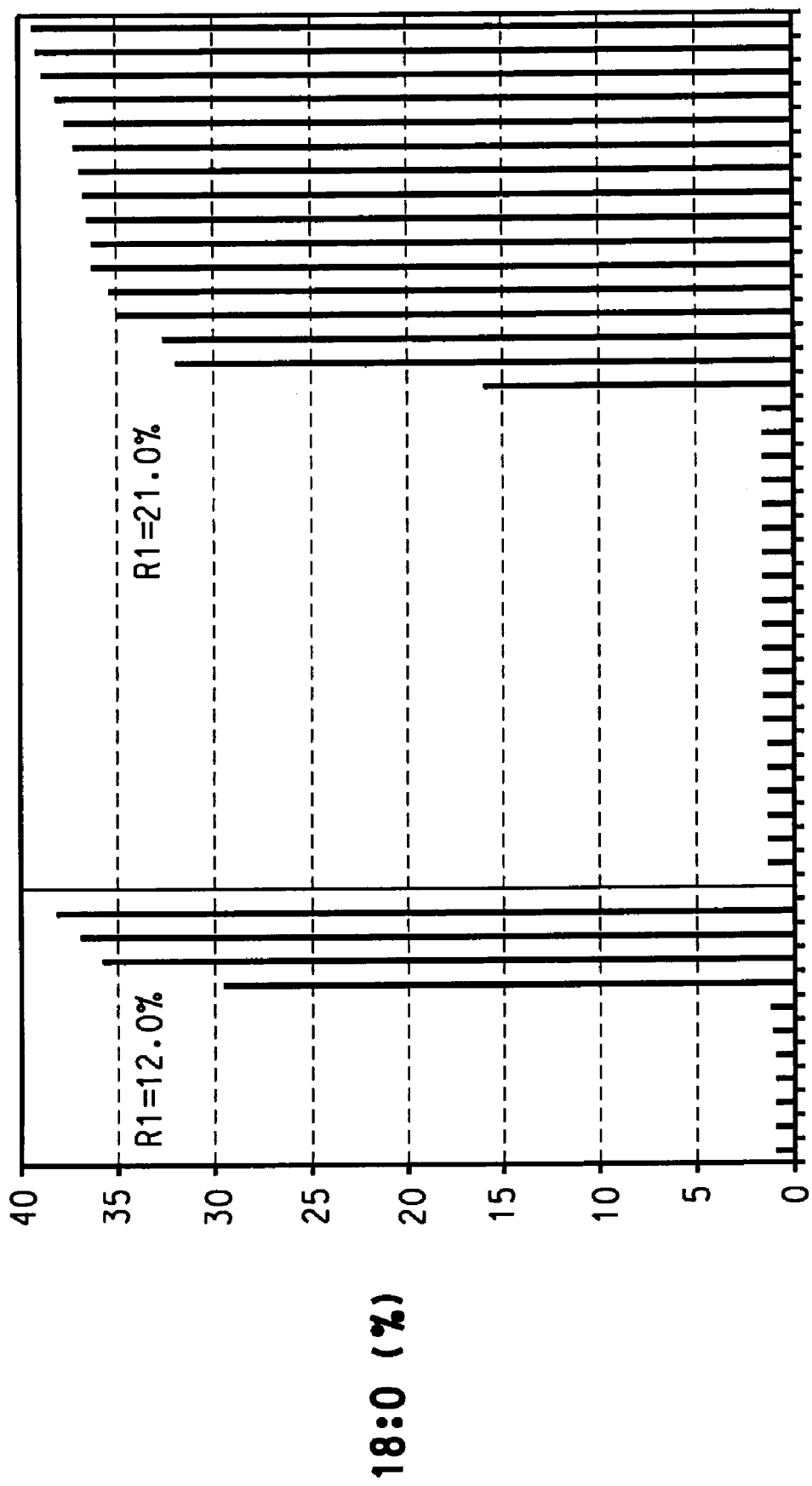
Figure 6:
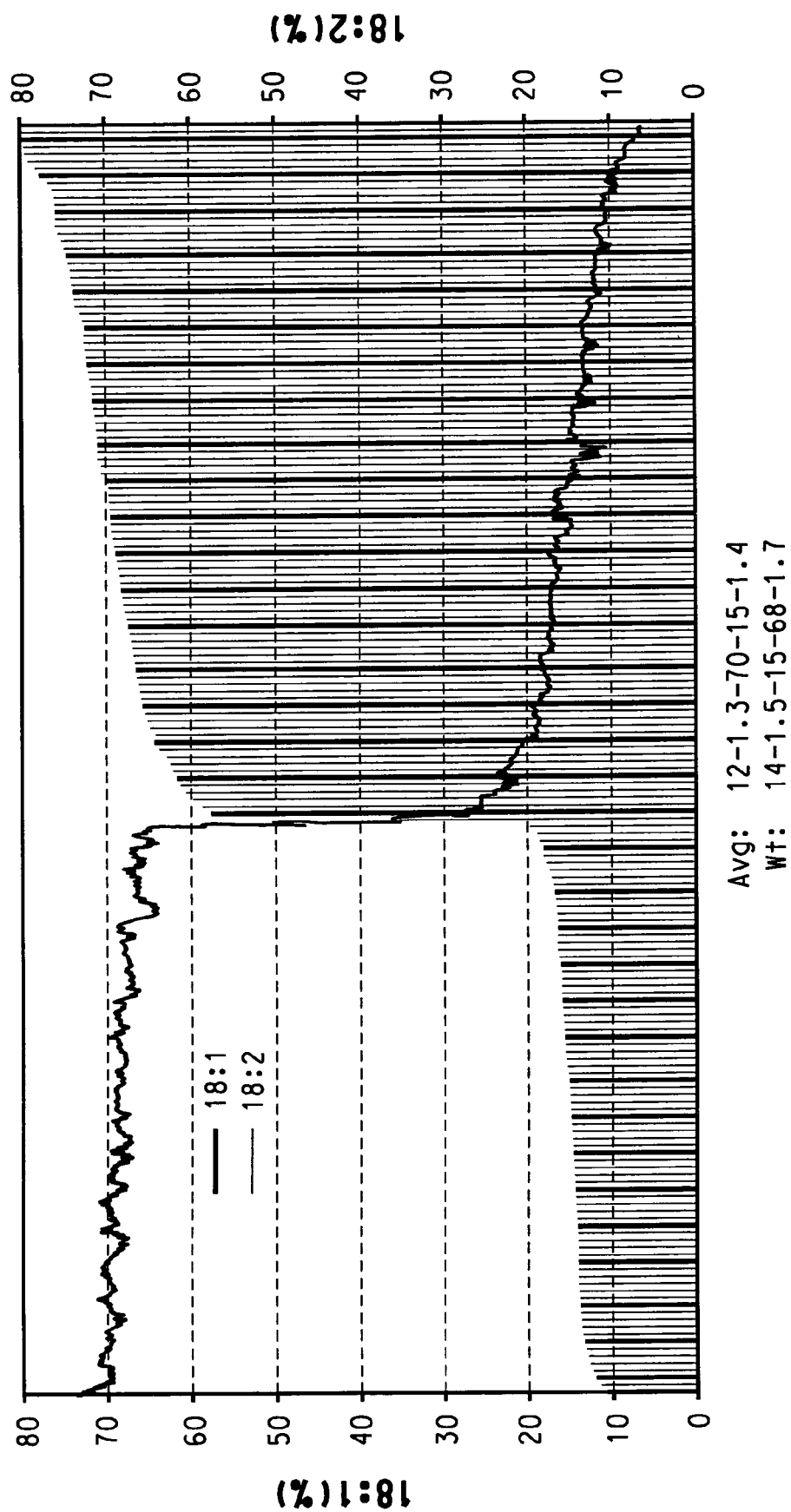
Figure 7A:
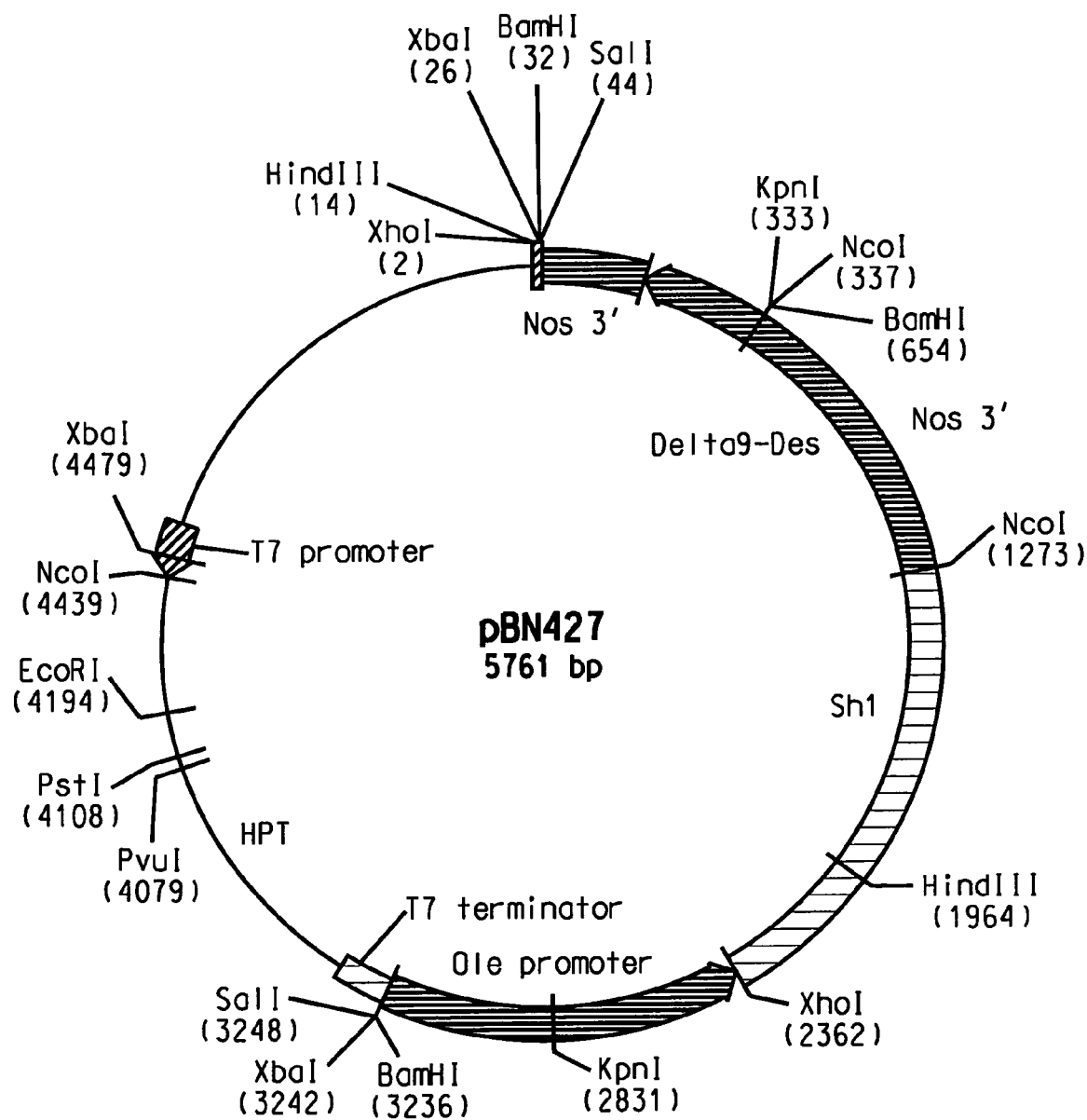
Figure 7B:
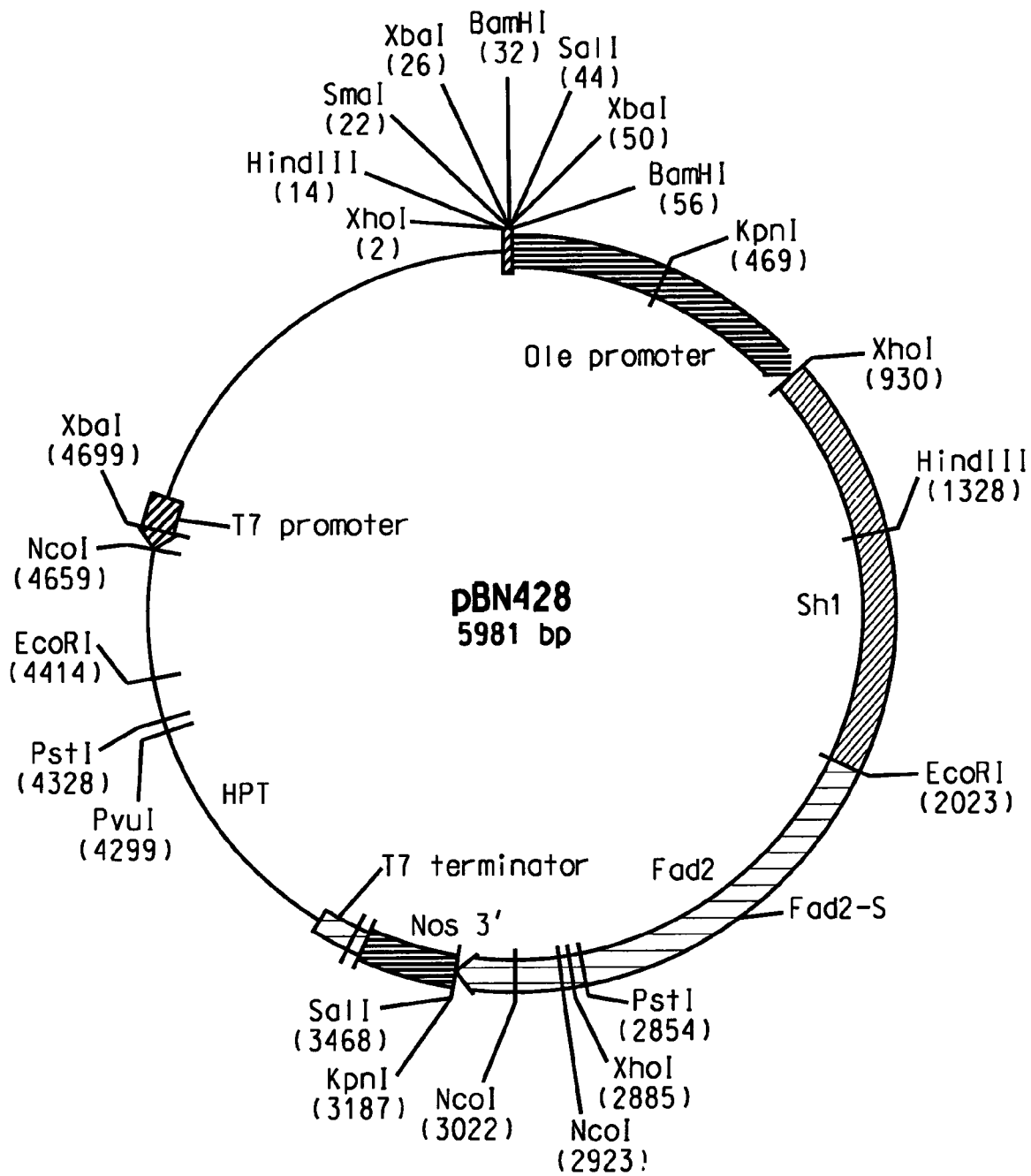
Figure 7C:
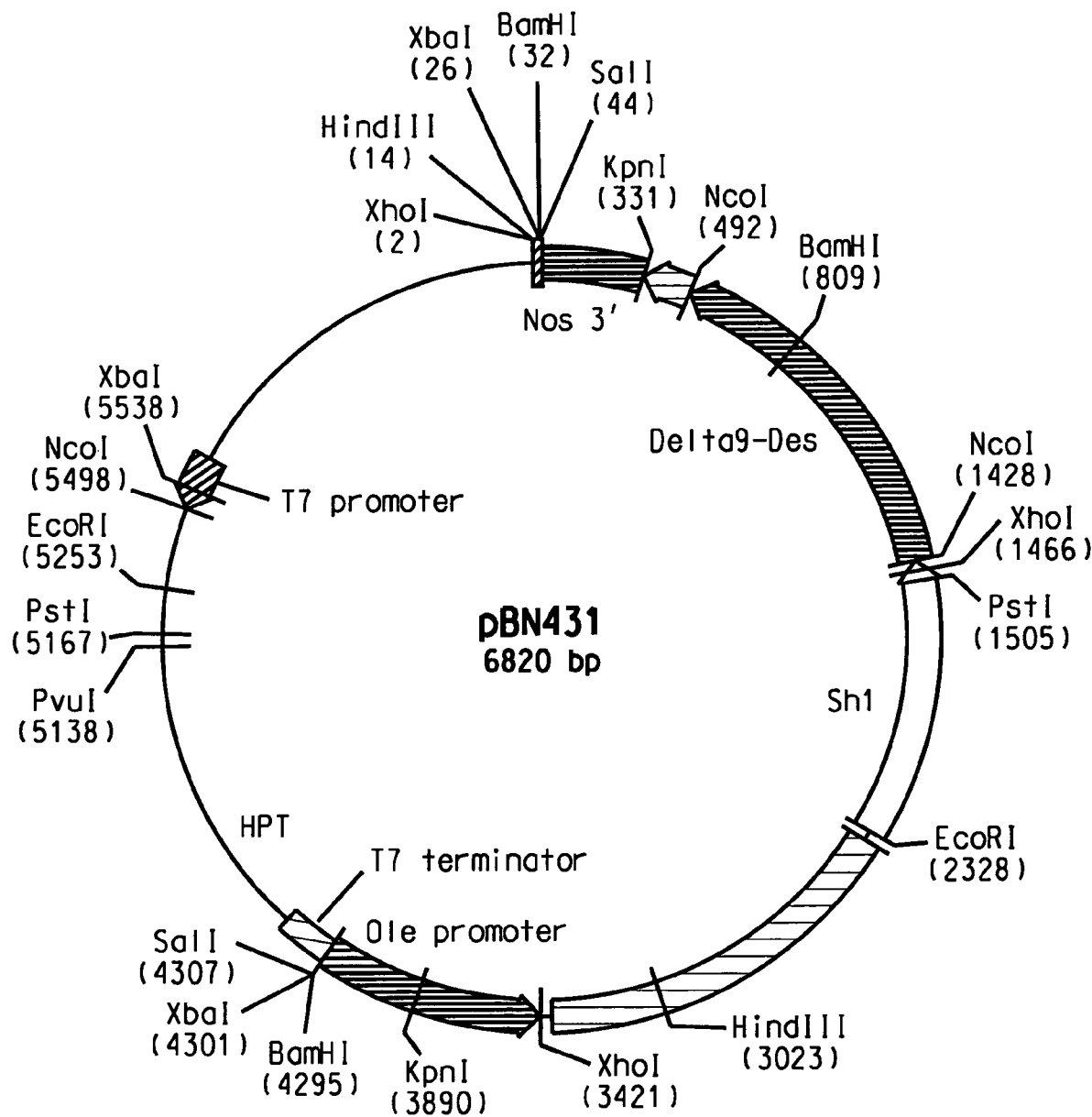

FIG. 2A depicts a restriction map of plasmid pML63.
FIG. 2B depicts a restriction map of plasmid pSH12.
FIG. 2C depicts a restriction map of plasmid pSM100.
FIG. 3A depicts a restriction map of plasmid pBN256.
FIG. 3B depicts a restriction map of plasmid pBN257.
FIG. 3C depicts a restriction map of plasmid pBN264.
FIG. 3D depicts a restriction map of plasmid pBN262.
FIG. 3E depicts a restriction map of plasmid pBN414.
FIG. 3F depicts a restriction map of plasmid pBN412.
FIG. 4A depicts the lipid profiles of individual kernels obtained from corn line FA013-2-4.
FIG. 4B is a histogram depicting the segregation analysis of the lipid profiles of individual kernels obtained from corn line FA013-2-4.
FIG. 5 depicts the lipid profiles of individual R2 kernels obtained from corn line FA013-3-2-15.
FIG. 6 depicts the lipid profiles of individual R1 kernels obtained from corn line FA014-5-1.
FIG. 7A depicts a restriction map of plasmid pBN427.
FIG. 7B depicts a restriction map of plasmid pBN428.
FIG. 7C depicts a restriction map of plasmid pBN431.

DETAILED DESCRIPTION OF THE INVENTION

In the context of this disclosure, a number of terms shall be utilized.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp (1989) CABIOS. 5:151–153) with the default parameters (GAP PENALTY=10, GAP LENGTH PENALTY=10). Default parameters for pairwise alignments and calculation of percent identiy of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) J. Mol. Biol. 215:403–410) and Gapped Blast (Altschul, S. F. et al., (1997) Nucleic Acids Res. 25:3389–3402).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (1989, Biochemistry of Plants 15:1–82). It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The term "shrunken 1 intron/exon" refers to a region of the shrunken 1 gene from corn. The particular intron/exon used in the present invention is derived from a non-coding region ("exon 1/intron 1") of the shrunken 1 gene and is identical to the sequence in GenBank accession # X02382 from nucleotides 1138 through 2220. As used herein, the terms shrunken 1 and its abbreviation, Sh1, are used interchangably.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

The expression "3' non-coding sequences" refers to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of an mRNA precursor. The use of different 3' non-coding sequences is exemplified by Ingelbrecht et al. (1989, Plant Cell 1:671–680).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or antisense orientation.

The term "expression", as used herein, refers to the production of a functional end-product. Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

"Altered expression" refers to the production of gene product(s) in transgenic organisms in amounts or proportions that differ significantly from that activity in comparable tissue (organ and of developmental type) from wild-type organisms.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be but are not limited to intracellular localization signals.

A "chloroplast transit peptide" is an amino acid sequence which is translated in conjunction with a protein and directs the protein to chloroplasts or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Delta-9 desaturase" (alternatively, "stearoyl-ACP desaturase") catalyzes the introduction of a double bond between carbon atoms 9 and 10 of stearoyl-ACP to form oleoyl-ACP. It can also convert stearoyl-CoA into oleoyl-CoA, albeit with reduced efficiency.

"Delta-12 desaturase" refers to a fatty acid desaturase that catalyzes the formation of a double bond between carbon positions 6 and 7 (numbered from the methyl end), (i.e., those that correspond to carbon positions 12 and 13 (numbered from the carbonyl carbon) of an 18 carbon-long fatty acyl chain.

As used herein, the expressions "nucleic acid fragment encoding a corn delta-9 desaturase" and "nucleic acid fragment encoding a corn delta-12 desaturase" refer to nucleic acid fragments that are derived from a desaturase cDNA or genomic sequence, but which may or may not produce active enzymes. For example, such a fragment could be a mutant sequence that does not give rise to a translated product, or coding frame has been shifted that may give rise to a different polypeptide, but which is functional for the alteration of desaturase enzyme level. In other words, such a fragment could be used in the construction of a co-suppression or antisense chimeric gene to alter desaturase enzyme level and, thus, alter the lipid profile of a plant transformed with such a chimeric gene.

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of corn cell transformation is use of particle-accelerated or "gene gun" transformation technology (Klein K. et al. (1987) *Nature* (*London*) 327:70–73; U.S. Pat. No. 4,945,050), or Agrobacterium-mediated method using an appropriate Ti plasmid containing the transgene (Ishida Y. et al. 1996, Nature Biotech. 14:745–750). The expression "transgenic event" refers to an independent transgenic line that is derived from a single callus clone containing a transgene.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the the target segment are annealed at low temperature and then extended at an intermediate temperature. One set of these three consecutive steps comprises a cycle. An "expression construct" is a plasmid vector or a subfragment thereof comprising the instant chimeric gene. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

An "R0" plant is equivalent to a "primary transformant," which is the plant regenerated directly from the tissue culture processes after transformation by the biolistic or Agrobacterium-mediated method. Seeds harvested from R0 plants, were named R1 or R0:1 seeds. Progenies derived from R1 seeds are R1 plants, and seeds harvested from R1 plants are R2 or R1:2 seeds. Future generations are named according to this convention.

The "kernel" is the corn caryopsis, consisting of a mature embryo and endosperm which are products of double fertilization. The term "corn" or "maize" represents any variety, cultivar, or population of *Zea mays* L.

"Grain" comprises mature corn kernels produced by commercial growers for on farm use or for sale to customers in both cases for purposes other than growing or reproducing the species. The "seed" is the mature corn kernel produced for the purpose of propagating the species and for sale to commercial growers. As used herein the terms seeds, kernels, and grains can be used interchangeably. The "embryo" or also termed "germ" is a young sporophytic plant, before the start of a period of rapid growth (seed germination). The embryo (germ) of corn contains the vast majority of the oil found in the kernel. The structure of embryo in cereal grain includes the embryonic axis and the scutellum. The "scutellum" is the single cotyledon of a cereal grain embryo, specialized for absorption of the endosperm. The "aleurone" is a proteinaceous material, usually in the form of small granules, occurring in the outermost cell layer of the endosperm of corn and other grains.

A "dominant" trait requires one allele to be dominant with respect to an alternative allele if an individual cell or organism homozygous for the dominant allele is phenotypically indistinguishable from the heterozygote. The other, alternative allele is said to be recessive. "Recessive" describes a gene whose phenotypic expression is masked in the heterozygote by a dominant allele. "Semi-dominant" describes an intermediate phenotype in a heterozygote. The term "homozygous" describes a genetic condition existing when identical alleles reside at corresponding loci on homologous chromosomes. The term "heterozygous" describes a genetic condition existing when different alleles reside at corresponding loci on homologous chromosomes.

As used herein in describing "oleic acid content", the term "high oleate" refers to a grain or seed having an oleic acid content of not less than about 60% of the total oil content of the seed, by weight when measured at 0% moisture. "Stearic acid content", the term "high stearate" refers to a grain or seed having an stearic acid content of not less than about 20% of the total oil content of the seed, by weight when measured at 0% moisture. "Saturated fatty acid" is a fatty acid that contains a saturated alkyl chain. The term "high saturate" refers to a grain or seed having an total saturated fatty acid content of not less than about 30% of the total oil content of the seed, by weight when measured at 0% moisture. The major components of the saturated fatty acid fraction of a grain or seed include but not limited to palmitic (16:0), stearic (18:0), and arachidic (20:0) acids.

A "carcass quality improving amount" is that amount needed to improve the carcass quality of an animal. The present invention concerns the alteration of lipid profiles in corn.

In one aspect this invention concerns an isolated nucleic acid fragment comprising a corn oleosin promoter wherein said promoter can be full length or partial and further wherein said promoter comprises a nucleotide sequence corresponding substantially to the nucleotide sequence in any of SEQ ID NOS:19 or 38–49 or said promoter comprises a fragment or subfragment that is substantially similar and functionally equivalent to any of the nucleotide sequences set forth in SEQ ID NOS:19 or 38–49. In addition, the fragment or subfragment discussed above may hybridize to the nucleotide sequence set forth in SEQ ID NOS:19 or 38–49 under moderately stringent conditions. This novel corn oleosin promoter is capable of driving gene expression in an embryo and aleurone-specific manner at a high expression level. Strong promoter activity in developing corn embryos is best achieved by using the nucleic acid fragment corresponding substantially to the nucleotide sequence set forth in SEQ ID NO:39 and an intron element in the expression construct as discussed in the examples below. It has been found that the activity of oleosin promoter is much higher, and expressed much earlier in the developing corn kernels, than a corn embryo/aleurone-specific promoter obtained from the globulin-1 gene. The preferred oleosin promoter has the nucleotide sequence set forth in SEQ ID NO:39. However, as those skilled in the art will appreciate, any functional promoter which has embryo/aleurone specificity is useful in the present invention. Other suitable promoters are well known to those skilled in the art, examples of which are discussed in WO 94/11516, the disclosure of which is hereby incorporated by reference. Furthermore, one skilled in the art will be able to use the methods and analyses that are described in the Examples below to identify other promoters with the desired embryo/aleurone specificity of expression. For example, using the instant optimized oleosin promoter as a contol, it is possible to identify other sequences that function in a similar manner, using the histological and molecular biological characterizations of embryo/aleurone promoter function, such as levels of expression of a GUS reporter function, timing of gene expression that is comtemporaneous with seed oil formation, and the appropriate tissue specificity.

In a second embodiment, this invention concerns an isolated nucleic acid fragment encoding a corn delta-9 stearoyl-ACP desaturase corresponding substantially to a nucleotide sequence set forth in any of SEQ ID NOS:8 or 10 or any functionally equivalent subfragment thereof. Chimeric genes comprising this nucleic acid fragment or subfragment thereof or the reverse complement of such fragment or subfragment operably linked to suitable regulatory suitable regulatory sequences can be constructed wherein expression of the chimeric gene results in an altered corn stearic acid phenotype.

Transgenic plants can be made in which a corn delta-9 desaturase enzyme is present at higher or lower levels than normal or in cell types or developmental stages in which it is not normally found. This would have the effect of altering the level of delta-9 desaturases in those cells. It may be desirable to reduce or eliminate expression or transcript accumulation of a gene encoding delta-9 desaturases in plants for some applications. In order to accomplish this, a chimeric gene designed for co-suppression of the endogenous delta-9 desaturases can be constructed by linking a nucleic acid fragment or subfragment thereof encoding corn delta-9 desaturases to plant promoter sequences. Alternatively, a chimeric gene designed to express antisense RNA for all or part of the instant nucleic acid fragment can be constructed by linking the nucleic acid fragment or subfragment in reverse orientation to plant promoter sequences, i.e., by linking the reverse complement of the fragment or subfragment. Either the co-suppression or antisense chimeric genes could be introduced into plants via transformation wherein expression or transcript accumulation of the corresponding endogenous genes are reduced or eliminated (Stam, et al. (1997) *Annals of Botany* 79:3–12).

Expression of a trait gene in corn kernels may be accomplished by constructing a chimeric gene in which the coding region of the trait gene and other regulatory element (for example, intron) is operably linked to the oleosin 16 kDa promoter. The chimeric gene may comprise the shrunken 1 intron1/exon1 in the 5'-untranslated sequence to either enhance the gene expression or stabilize the transcripts of the transgene. The Sh1 exon I sequence will remain as part of the leader sequences in mRNA after the splicing occurs. All or a portion of the coding sequence of the trait gene is located 3' to the Sh1 exon1/intron1 sequence, and may be in a sense or antisense orientation. Such a chimeric gene may also comprise one or more introns in order to facilitate gene expression. The position of the intron element(s) can be in the translation leader sequence as described above, or in the coding region of the trait gene. Intron elements from other genes, such as actin-1, ubiquitin-1, Adh-1, fad2-1, and fad2-2 may also be used in replacing the Sh1 element to have the same effect. Accordingly, any intron element from other genes may be used to practice the instant invention. 3' non-coding sequences containing transcription termination signals may also be provided in the chimeric gene.

All or a portion of any of the nucleic acid fragments of the instant invention may also be used as a probe for genetically and physically mapping the genes that it is a part of, and as a marker for traits linked to these genes. Such information may be useful in plant breeding in order to develop lines with desired phenotypes. For example, such fragment may be used as a restriction fragment length polymorphism (RFLP) marker. Southern blots (Sambrook) of restriction-digested plant genomic DNA may be probed with the nucleic acid fragment of the instant invention. The resulting banding patterns may then be subjected to genetic analyses using computer programs such as MapMaker (Lander et at., (1987) *Genomics* 1:174–181) in order to construct a genetic map. In addition, the nucleic acid fragment of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1): 37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequence may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In a third embodiment, this invention concerns an isolated nucleic acid fragment encoding a corn delta-12 desaturase corresponding substantially to the nucleotide sequence set forth in SEQ ID NO:2 or any functionally equivalent subfragment thereof. The gene for microsomal delta-12 fatty acid desaturases described in WO 94/11516, published on May 26, 1994, can be used to practice the instant invention. Chimeric genes comprising such a nucleic acid fragment or subfragment thereof or the reverse complement of such fragment or subfragment operably linked to suitable regulatory sequences can be constructed wherein expression of the chimeric gene results in an altered corn oleic acid phenotype. As was discussed above with respect to an isolated nucleic acid fragment encoding a delta-9 desaturase, it may be desirable to reduce or eliminate expression or transcript accumulation of a gene encoding delta-12 desaturases in plants for some applications. To accomplish this, a chimeric gene designed for co-suppression of the endogenous delta-12 desaturases can be constructed by linking a nucleic acid fragment or subfragment thereof to plant promoter sequences. Alternatively, a chimeric gene designed to express antisense RNA for all or part of this nucleic acid fragment can be constructed by linking the nucleic acid fragment or subfragment in reverse orientation to plant promoter sequences, i.e., by linking the reverse complement of the fragment or subfragment to plant promoter sequences. Either the co-suppression or antisense chimeric genes can be introduced into plants via transformation wherein expression of the corresponding endogenous genes are reduced or eliminated.

The aforementioned chimeric genes can further comprise (1) an isolated nucleic acid fragment comprising a corn oleosin promoter wherein said promoter can be full length or partial and further wherein said promoter comprises a nucleotide sequence corresponding substantially to the nucleotide sequence in any of SEQ ID NOS:19 or 38–49 or said promoter comprises a fragment or subfragment that is substantially similar and functionally equivalent to any of the nucleotide sequences set forth in SEQ ID NOS:19 or 38–49 and/or (2) a shrunken 1 intron/exon.

In a further aspect, chimeric genes can be constructed to encompass a variety of combinations, including but not limited to the following:

a) A chimeric gene comprising an isolated nucleic acid fragment encoding a corn delta-9 stearoyl-ACP desaturase corresponding substantially to a nucleotide sequence set forth in any of SEQ ID NOS:8 or 10 or any functionally equivalent subfragment thereof or the reverse complement of this fragment or subfragment and a nucleic acid fragment encoding a corn delta-12 desaturase or any functionally equivalent subfragment thereof or the reverse complement of this fragment or subfragment wherein the fragments or subfragment are operably linked and further wherein expression of this chimeric gene results in an altered corn oil phenotype.

The nucleic acid fragment encoding a corn delta-12 desaturase enzyme used in the contruction of such a chimeric gene can be the fragment identified in WO 94/11516 or this fragment can correspond substantially to the nucleotide sequence set forth in SEQ ID NO:2 or any functionally equivalent subfragment thereof.

b) The chimeric gene described in (a) above can still further comprise an isolated nucleic acid fragment comprising a corn oleosin promoter wherein said promoter can be full length or partial and further wherein said promoter comprises a nucleotide sequence corresponding substantially to the nucleotide sequence in any of SEQ ID NOS:19 or 38–49 or said promoter comprises a fragment or subfragment that is substantially similar and functionally equivalent to any of the nucleotide sequences set forth in SEQ ID NOS:19 or 38–49.

c) The chimeric gene described in (a) or (b) above can each further comprise a shrunken 1 intron/exon.

d) A chimeric gene comprising (1) an isolated nucleic acid fragment comprising a corn oleosin promoter wherein said promoter can be full length or partial and further wherein said promoter comprises a nucleotide sequence corresponding substantially to the nucleotide sequence in any of SEQ ID NOS:19 or 38–49 or said promoter comprises a fragment or subfragment that is substantially similar and functionally equivalent to any of the nucleotide sequences set forth in SEQ ID NOS:19 or 38–49, (2) an isolated nucleic acid fragment encoding a corn delta-9 stearoyl-ACP desaturase corresponding substantially to a nucleotide sequence set forth in any of SEQ ID NOS:8 or 10 or a functionally equivalent subfragment thereof or the reverse complement of the fragment or subfragment, (3) a nucleic acid fragment encoding a corn delta-12 desaturase or any functionally equivalent subfragment thereof, thereof or the reverse complement of the fragment or subfragment, and (4) a shrunken 1 intron/exon wherein the fragments are operably linked and further wherein expression of this chimeric gene results in an altered corn oil phenotype. In another embodiment, the nucleic acid fragment encoding the delta-12 desaturase corresponds substantially to the nucleotide sequence set forth in SEQ ID NO:2.

e) A chimeric gene comprising (1) an isolated nucleic acid fragment comprising a corn oleosin promoter wherein said promoter can be full length or partial and further wherein said promoter comprises a nucleotide sequence corresponding substantially to the nucleotide sequence in any of SEQ ID NOS:19 or 38–49 or said promoter comprises a fragment or subfragment that is substantially similar and functionally equivalent to any of the nucleotide sequences set forth in SEQ ID NOS:19 or 38–49, (2) a nucleic acid fragment encoding a corn delta-12 desaturase corresponding substantially to the nucleotide sequence set forth in SEQ ID NO:1 or any functionally equivalent subfragment thereof, or the reverse complement of this fragment or subfragment, or an isolated nucleic acid fragment corresponding substantially to the nucleotide sequence set forth in SEQ ID NO:58 or 59 or any functionally equivalent subfragment thereof, or the reverse complement of this fragment or subfragment and a shrunken 1 intron/exon wherein the fragments are operably linked and further wherein expression of this chimeric gene results in an altered corn oil phenotype. In another embodiment, the nucleic acid fragment encoding the delta-12 desaturase corresponds substantially to the nucleotide sequence set forth in SEQ ID NO:2.

This invention also concerns corn plants and plant parts thereof comprising in their genome these various chimeric genes. Corn grains obtained from such plants will have altered corn oil phenotypes. For example, a corn grain obtained from a corn plant comprising in its genome a chimeric gene comprising an isolated nucleic acid fragment encoding a corn delta-9 stearoyl-ACP desaturase corresponding substantially to a nucleotide sequence set forth in any of SEQ ID NOS:8 or 10 or any functionally equivalent subfragment thereof or the reverse complement of this fragment or subfragment operably linked to suitable regulatory sequences will have a stearic acid content of not less than about 20% of the total oil content or a total saturate content of not less than about 35% of the total oil content. The preferred regulatory sequence is the oleosin promoter. This same phenotype will be obtained if this chimeric gene further comprises an isolated nucleic acid fragment encoding a corn delta-9 stearoyl-ACP desaturase corresponding substantially to a nucleotide sequence set forth in any of SEQ ID NOS:8 or 10 or any functionally equivalent subfragment thereof or the reverse complement of this fragment or subfragment and/or a shrunken 1 intron/exon.

A corn grain comprising in its genome a chimeric gene comprising an isolated nucleic acid fragment comprising a corn delta-12 desaturase corresponding substantially to the nucleotide sequence set forth in SEQ ID NO:1, a functionally equivalent subfragment thereof or the reverse complement of said fragment or subfragment, or an isolated nucleic acid fragment corresponding substantially to the nucleotide sequence set forth in SEQ ID NO:58 or 59 or a functionally equivalent subfragment thereof or the reverse complement of such fragment or subfragment, an isolated nucleic acid fragment comprising a corn oleosin promoter wherein said promoter can be full length or partial and further wherein said promoter comprises a nucleotide sequence corresponding substantially to the nucleotide sequence in any of SEQ ID NOS:19 or 38–49 or said promoter comprises a fragment or subfragment that is substantially similar and functionally equivalent to any of the nucleotide sequences set forth in SEQ ID NOS:19 or 38–49, and shrunken 1 intron/exon wherein said fragments are operably linked and further wherein expression of the chimeric gene results in an altered corn oleic acid phenotype, wherein said corn grain has an oil content in the range from about 6% to about 10% on a dry matter basis and further wherein said oil is comprised of not less than about 60% oleic acid based on the total oil content of the seed.

Such a corn grain can be obtained by the Top Cross® grain production method cited in the Examples below. In this method one of the parents comprises the chimeric gene discussed above and the other parent comprises a high oil phenotype in the range from about 12% to 20% oil by weight or on a dry matter basis. Alternatively, one of the parents may comprise both a transgene of the invention, e.g., a chimeric gene of this invention, and a high oil phenotype, and the other parent is an elite hybrid line.

A corn grain obtained from a corn plant comprising in its genome a chimeric gene comprising an isolated nucleic acid fragment encoding a corn delta-12 desaturase corresponding substantially to the nucleotide sequence set forth in SEQ ID NO:2 or any functionally equivalent subfragment thereof or the reverse complement of the fragment or subfragment operably linked to suitable regulatory sequences will have an oleic acid content of not less than about 70% of the total oil content. The preferred regulatory sequence is the oleosin promoter. This same phenotype will be obtain if this chimeric gene further comprises an isolated nucleic acid fragment encoding a corn delta-9 stearoyl-ACP desaturase corresponding substantially to a nucleotide sequence set forth in any of SEQ ID NOS:8 or 10 or any functionally equivalent subfragment thereof thereof or the reverse complement of the fragment or subfragment and/or a shrunken 1 intron/exon.

With respect to the chimeric genes discussed above in (a) through (e), comprising the various gene combinations, corn grains obtained from plants comprising such chimeric genes will have a total saturate content of not less than about 30% of the total oil content and an oleic acid content of not less than about 30% of the total oil content.

This invention also concerns seeds obtained from corn plants containing any of the above-discussed chimeric genes, oil obtained from such seeds, animal feed derived from the processing of such seeds, the use of such oil in food, animal feed, cooking or industrial applications and products made from the hydrogenation, fractionation, interesterification or hydrolysis of such oil, by-products made during the production of this oil, and methods for improving the carcass quality of animals.

The present invention also concerns a method for improving the carcass quality of an animal which comprises feeding the animal a carcass quality improving amount of animal feed derived from the processing of corn seeds/grain obtained from any of the corn plants of the present invention.

Vegetable oils are often used in high temperature applications. Oil oxidation is accelerated in the presence of heat. It is important that an oil be able to withstand these conditions for applications such as frying, baking, roasting, etc. In some cases, antioxidants may be added to improve stability but not all antioxidants withstand high temperatures. In addition, in many cases a food manufacturer does not want to use oils with added antioxidants if a label with unadulterated ingredients is desired. Therefore, an oil which is stable to oxidation under high temperatures in the absence of any additives or other processing is highly desirable. Overheating of oils often leads to thermal polymerization of the oil and oxidation products resulting in a gummy, varnish-like buildup on the equipment used for heating and excessive foaming of the oil. As a result of oxidation, a variety of degradation products are formed depending on the conditions under which the oil is exposed. High temperature stability can be evaluated by exposing the oils to high temperature and monitoring the formation of the undesirable degradation products. These include both volatile and nonvolatile products and may be hydrocarbons, alcohols, aldehydes, ketones, and acids. The nonvolatile components can be further classified into polar and polymerized compounds. The polar and polymerized compounds present in a degraded oil can be analyzed directly by reverse phase high performance liquid chromatography as described in Lin, S. S., 1991, Fats and oils oxidation. Introduction to Fats and Oils Technology (Wan, P. J. ed.), pages 211–232, Am. Oil Chem. Soc.

The oil of this invention can be used in a variety of applications. In general, oxidative stability is related to flavor stability. The oil of this invention can be used in the preparation of foods. Examples include, but are not limited to, uses as ingredients, as coatings, as salad oils, as spraying oils, as roasting oils, and as frying oils. Foods in which the oil may be used include, but are not limited to, crackers and snack foods, confectionery products, syrups and toppings, sauces and gravies, soups, batter and breading mixes, baking mixes and doughs. Foods which incorporate the oil of this invention may retain better flavor over longer periods of time due to the improved stability against oxidation imparted by this oil.

The oils of this invention can also be used as a blending source to make a blended oil product. By a blending source, it is meant that the oil of this invention can be mixed with other vegetable oils to improve the characteristics, such as fatty acid composition, flavor, and oxidative stability, of the other oils. The amount of oil of this invention which can be used will depend upon the desired properties sought to be achieved in the resulting final blended oil product. Examples of blended oil products include, but are not limited to, margarines, shortenings, frying oils, salad oils, etc.

In another aspect, this invention concerns the industrial use of the oil of this invention for industrial applications such as an industrial lubricant for a variety of end uses, as a hydraulic fluid, etc. The industrial use of vegetable oils as a base fluid for lubricants has been known for many years. However, interest has intensified due to environmental concerns over the use of petroleum oils in environmentally sensitive areas. Vegetable oils are readily biodegradable, have low toxicity and have good lubricant characteristics. However, high pour points and rapid oxidation at high temperatures limit their use. Since the oil of this invention is low in polyunsaturates, as discussed herein, and has high oxidative stability and high temperature stability, these characteristics also make the oil of this invention desirable for industrial applications such as an industrial fluid, i.e., as industrial lubricant or as a hydraulic fluid, etc. Additives which can be used to make industrial lubricants and hydraulic fluids are commercially available. Indeed, some additives have been specially formulated for use with high oleic vegetable oils. Additives generally contain antioxidants and materials which retard foaming, wear, rust, etc.

Oil is obtained from plants by a milling process. Corn oil is extracted from kernels through the use of a either a wet or dry milling process. Wet milling is a multi-step process involving steeping and grinding of the kernels and separation of the starch, protein, oil, and fiber fractions. A review of the maize wet milling process is given by S. R. Eckhoff in the Proceedings of the Fourth Corn Utilization Conference, Jun. 24–26, 1992, St. Louis, Mo., printed by the National Corn Growers Association, CIBA-GEIGY Seed Division and the United States Department of Agriculture. Dry milling is a process by which the germ and hull of the corn kernel are separated from the endosperm by the controlled addition of water to the grain and subsequent passage through a degerming mill and a series of rollers and sieves. The U.S. dry milling industry produces approximately 50 million pounds of crude corn oil per year, and the wet milling industry produces over one billion pounds of crude corn oil (Fitch, B. (1985) JAOCS 62(11):1524–1531). The resulting oil is called crude oil.

The crude oil may be degummed by hydrating phospholipids and other polar and neutral lipid complexes which facilitate their separation from the nonhydrating, triglyceride fraction. Oil may be further refined for the removal of impurities; primarily free fatty acids, pigments, and residual gums. Refining is accomplished by the addition of caustic which reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth which removes most of the chlorophyll and carotenoid compounds. The refined oil can be hydrogenated resulting in fats with various melting properties and textures. Winterization (fractionation) may be used to remove stearine from the hydrogenated oil through crystallization under carefully controlled cooling conditions. Deodorization which is principally steam distillation under vacuum, is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high value pharmaceutical products. Refined, bleached, (hydrogenated, fractionated) and deodorized oils and fats may be packaged and sold directly or further processed into more specialized products.

Hydrogenation is a chemical reaction in which hydrogen is added to the unsaturated fatty acid double bonds with the aid of a catalyst such as nickel. High oleic oil contains unsaturated oleic acid, linoleic acid, and minor amount of linolenic acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction which in turn alter the composition of the final product. Operating conditions including pressure, temperature, catalyst type and concentration, agitation and reactor design are among the more important parameters which can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings, used in the manufacture of baking products, solid fats and shortenings used for commercial flying and roasting operations, and base stocks for margarine manufacture are among the myriad of possible oil and fat products achieved through hydrogenation. A more detailed description of hydrogenation and hydrogenated products can be found in Patterson, H. B. W., 1994, Hydrogenation of Fats and Oils: Theory and Practice. The American Oil Chemists' Society.

Interesterification refers to the exchange of the fatty acyl moiety between an ester and an acid (acidolysis), an ester and an alcohol (alcoholysis) or an ester and ester (transesterification). Interesterification reactions are achieved using chemical or enzymatic processes. Random or directed transesterification processes rearrange the fatty acids on the triglyceride molecule without changing the fatty acid composition. The modified triglyceride structure may result in a fat with altered physical properties. Directed interesterification reactions using lipases are becoming of increasing interest for high value specialty products like cocoa butter substitutes. Products being commercially produced using interesterification reactions include but are not limited to shortenings, margarines, cocoa butter substitutes and structured lipids containing medium chain fatty acids and polyunsaturated fatty acids. Interesterification is further discussed in Hui, Y. H. (1996, Bailey's Industrial Oil and Fat Products, Volume 4, John Wiley & Sons).

Fatty acids and fatty acid methyl esters are two of the more important oleochemicals derived from vegetables oils. Fatty acids are used for the production of many products such as soaps, medium chain triglycerides, polyol esters, alkanolamides, etc. Vegetable oils can be hydrolyzed or split into their corresponding fatty acids and glycerine. Fatty acids produced from various fat splitting processes may be used crude or more often are purified into fractions or individual fatty acids by distillation and fractionation. Purified fatty acids and fractions thereof are converted into a wide variety of oleochemicals, such as dimer and trimer acids, diacids, alcohols, amines, amides, and esters. Fatty acid methyl esters are increasingly replacing fatty acids as starting materials for many oleochemicals such as fatty alcohols, alkanolamides, a-sulfonated methyl esters, diesel oil components, etc. Glycerine is also obtained by the cleavage of triglycerides using splitting or hydrolysis of vegetable oils. Further references on the commercial use of fatty acids and oleochemicals may be found in Erickson, D. R., 1995, Practical Handbook of Soybean Processing and Utilization, The American Oil Chemists' Society, and United Soybean Board; Pryde, E. H., 1979, Fatty Acids, The American Oil Chemists' Society; and Hui, Y. H., 1996, Bailey's Industrial Oil and Fat Products, Volume 4, John Wiley & Sons.

As was discussed above, this invention includes a transgenic corn plant capable of producing grains having an oleic acid content of not less than about 60% of the total oil content. The high oleate trait is dominant. Therefore, the desired phenotype can be obtained if only one of the parental lines in the seeds or grains production scheme contains the trait gene. The timeline for commercial production of corn having elevated oleic levels can be greatly accelerated.

In addition, the transgenic high saturate trait is dominant. Therefore, the desired phenotype can be obtained if only one of the parental lines in the seeds or grains production scheme contains the trait gene. The timeline for commercial production of corn having elevated oleic levels can be greatly accelerated. The DNA sequence information set forth in the instant invention may be used to isolate cDNAs and genes encoding delta-9 and delta-12 desaturases from corn. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding the desaturases (either as cDNAs or genomic DNAs), could be isolated directly by using all or a portion of the instant nucleic acid sequences to create DNA hybridization probes which could be used to screen libraries employing methodology well known to those skilled in the art. Specific oligonucleotide probes based upon the instant nucleic acid sequences can be designed and synthesized by methods known in the art (Sambrook). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency. It is further well known to persons skilled in the art that minor alterations (substitutions, additions or deletions) may be created by the use of various in vitro mutagenesis protocols. In this manner, any of the nucleic acid fragments of the instant invention may be readily obtained.

EXAMPLES

The present invention is further defined in the following EXAMPLES, in which all parts and percentages are by weight and degrees are Celsius, unless otherwise stated. From the above discussion and these EXAMPLES, one skilled in the art can ascertain the essential characteristics of this invention, and without departing from the spirit and scope thereof, can make various changes and modifications of the invention to adapt it to various usages and conditions.

Example 1

Corn fad2-2 cDNA and Genomic DNA Clones

A corn embryo cDNA library was screened using a radioisotopically-labeled DNA fragment obtained by PCR and containing the corn gene for delta-12 desaturase ("fad2-1", WO 94/11516, and set forth in SEQ ID NO:1). A second delta-12 desaturase cDNA clone was identified on the basis of its sequence. The second gene for delta-12 desaturase is designated fad2-2.

The full-length cDNA sequence is shown in SEQ ID NO:2. It encodes a polypeptide of 392 amino acids (translation frame: nucleotide 176–1351). The coding region of the corn fad2-2 shares significant sequence identity with fad2-1: they share 88% identify at the amino acid level, and 92% at the nucleotide level. They also possess 77% identity at the 5'-untranslated region, and 64% at the 3' end.

A full-length or a portion of the coding region of either one of genes in either antisense or sense approach may be used to suppress both the fad2-1 and fad2-2 genes or gene products, due to the significant homology in the coding region between the fad2-1 and fad2-2 genes, and thus produce a high oleate phenotype in transgenic corn.

A genomic clone with a 13 kb insert containing the fad2-2 gene was identified using the corn fad2-1 cDNA insert as a probe in a screen of a corn genomic DNA library (Mo17 line, in λFix II vector, Stratagene, La Jolla, Calif.). The sequence upstream of the coding region is shown in SEQ ID NO:4, which contains the upstream regulatory element, 5'-untranslated region, and a 6.7 kb intron (nucleotide position at 5651–12301) located inside the 5'-untranslated region. The intron splice site (/GT-AG/) is conserved. The 5'-leader sequence (nucleotide position 5492–5650, and 12302–12313) flanking the intron matches the sequence of the 5'-untranslated region of fad2-2 cDNA. The putative TATA box (TAAATA) is at position 5439–5444, which is 47 nucleotides upstream from the first nucleotide of the fad2-2 cDNA clone. The promoter element of this gene may be used to express a gene of interest in transgenic corn plants.

Example 2

Corn fad2-1 Intron

Based on the fad2-2 intron sequence (SEQ ID NO:4), primers (SEQ ID NOS:54 and 55) were designed for PCR amplification of a fad2-2 fragment from corn genomic DNA for use in mapping the fad2-2 locus.

```
5'-CTGCACTGAAAGTTTTGGCA-3'          SEQ ID NO:54

5'-AGTACAGCGGCCAGGCGGCGTAGCG-3'     SEQ ID NO:55
```

In addition to the expected 0.8 kb fragment that should result from amplification from the fad2-2 sequence, a second fragment, 1.1 kb in length, was also produced in the same PCR. The 1.1 kb fragment was purified, sequenced, and it was determined that this fragment contains a portion of the fad2-1 intron. A new set of primers (SEQ ID NOS:56 and 57) were designed according to the sequences of this 1.1 kb partial intron, and the 5'-untranslated region of fad2-1.

```
5'-AAGGGGAGAGAGAGGTGAGG-3'    SEQ ID NO:56

5'-TGCATTGAAGGTGGTGGTAA-3'    SEQ ID NO:57
```

Using the new primer set and corn genomic DNA as the template, a PCR product containing the other half of the fad2-1 intron was obtained. The fragment was purified and sequenced. A contig containing the complete fad2-1 intron was assembled using the sequence that overlaps with the 1.1 kb fragment. The contig is shown in SEQ ID NO:5.

Comparison of the structures of corn fad2-1 and fad2-2 genes revealed that the locations of the introns are conserved. Both of the introns are localized to the 5'-leader region of the precursor RNA. The fad2-1 intron is 11 bases upstream of the start codon (ATG), whereas the fad2-2 intron is 27 bases upstream of the start codon. The consensus sequences of intron splice sites (/GT---AG/) are conserved in both introns.

Comparison of the fad2-1 and fad2-2 introns using the BestFit program (Genetics Computer Group, Madison, Wis.; employing the algorithm of Smith and Waterman (1981) Advances in Applied Mathematics 2:482–489) demonstrated 81% sequence identity in the first 0.76 kb (nucleotide positions 3–765 in the fad2-1 intron [SEQ ID NO:5]) and nucleotides 5650–6790 of the fad2-2 intron [as shown in SEQ ID NO:4]), and 73% homology near the end of the intron (nucleotide positions 2619–2893 in the fad2-1 intron [SEQ ID NO:5]), and 12006–12320 in the fad2-2 intron [SEQ ID NO:4]). The internal intron sequences are not conserved.

Very few plant introns studied to date are longer than 2–3 kb (Simpson and Filipowicz (1996) Plant Mol. Biol. 32:1–41). Further investigation indicated that the unusually large size of the fad2-2 intron was due to insertion of an apparently intact copy (about 4.8 kb) of a retrotransposable element, Milt (SanMiguel et al. (1996) Science 274:765–768). This retroelement is inserted in an opposite orientation of the transcription direction of the fad2-2 gene. The fad2-1 intron does not contain this element.

Example 3

Cloning and Sequencing of Corn Delta-9 Desaturase cDNA

Degenerate primers were designed according to the conserved regions of delta-9 desaturase genes from various species, and used for PCR. These are set forth in SEQ ID NOS:6 and 7.

```
5'-GAYATGATHACNGARGAR-3'    SEQ ID NO:6

5'-CCRTCRTACATNAGATG-3'     SEQ ID NO:7
```

Two PCR fragments (520 and 500 bp, respectively) were generated when these oligomers were used as primers and DNA from a corn embryo cDNA library was used as a template. The fragments were purified and used as probes to screen a corn embryo cDNA library. Two independent clones (pCD520, and pCD500) were isolated.

These two clones were sequenced, and cross-hybridized between themselves and with the soybean delta-9 desaturase gene. It was confirmed that only the insert of pCD520 was homologous to the soybean delta-9 desaturase gene. The cDNA sequence was shown in SEQ ID NO:8. Nucleotide number 1–133 is the 5'-untranslated leader sequence. The coding sequence starts from 134 (ATG), and the stop codon (TAA) is at 1309–1312, encoding a polypeptide of 392 amino acids set forth in SEQ ID NO:9. There are 396 nucleotides in the 3'-untranslated region (1309–1714) including the poly(A) tail starting at nucleotide position 1661. There is no obvious polyadenylation signal in this region with the possible exception of a AT-rich region (1621–1630) located at 31 base upstream from the poly(A) tail.

The sequence of the cDNA insert in pCD520 (SEQ ID NO:8) was used as a query in a search of a DuPont EST database using BLAST programs and algorithms as search tools (Altschul, S. F. et al. (1990) *J. Mol. Biol.* 215:403–410 and Altschul, S. F. et al. (1997) *Nucleic Acids Res.* 25:3389–3402). An EST was identified by this method, and the full sequence of the cDNA clone from which it was derived is given in SEQ ID NO:10. The 5'-untranslated leader sequence is in nucleotide position from 1–101, the coding sequence starts from position 102, and ends with the stop codon (TAA) in position 1278–1280. This sequence also encodes a polypeptide of 392 amino acids the sequence of which is listed in SEQ ID NO:11. The coding region of this second corn delta-9 desaturase gene shares significant homology with that listed in SEQ ID NO:8: The sequence share 63% identity and 83% similarity at the nucleotide level, and 77% identity at the amino acid level. There are 429 nucleotides in the 3'-untranslated region of SEQ ID NO:10, including the poly(A) tail starting at nucleotide 1626. A putative polyadenylation signal (AATAA) is located at nucleotides 1588–1594.

Example 4

Spatial and Developmental Regulation of Delta-9 and Delta-12 Desaturases

Northern blot analyses were performed to investigate the spatial and developmental regulation of genes involved in lipid biosynthesis in corn embryos. Total RNA fractions were purified from leaves, sheath, tassels, roots and immature embryos dissected from the developing kernels at 15, 20, 25, and 30 days after pollination (DAP). RNA blots were prepared and hybridized individually with $^{32}$P-labeled probes of corn fad2-1 (SEQ ID NO:1), delta-9 desaturase (SEQ ID NO:8), oleosin 16 kDa (Vance and Huang 1987), and globulin 1 (Belanger and Kriz, 1989, Plant Physiol. 91:636–643). The probes were prepared using gene-specific fragments purified as described below.

Using the sequence of fad2-1 (SEQ ID NO:1), primers (SEQ ID NOS:12 and 13) were designed to hybridize the 3'-end, and used in PCR with fad2-1 cDNA as the template.

```
5'-AGGACGCTACCGTAGGAA-3'    SEQ ID NO:12

5'-GCGATGGCACTGCAGTA-3'     SEQ ID NO:13
```

An expected 0.16 kb PCR fragment was gel-purified, and used as a fad2-1-specific probe. A cDNA clone containing the delta-9 desaturase (SEQ ID NO:8) was digested with EcoRI and XhoI, and a 1.7 kb fragment containing the entire cDNA insert was purified as the delta-9 desaturase gene probe.

The oleosin 16 kDa-specific probe was a 0.25 kb fragment purified from a PCR, using the corn embryo cDNA library as the template and primers (SEQ ID NO:14 and 15) hybridizing to the 3'-untranslated region of oleosin 16 kDa gene.

```
5'-CTTGAGAGAAGAACCACACTC-3'    SEQ ID NO:14

5'-CTAGACATATCGAGCATGCTG-3'    SEQ ID NO:15
```

A corn genomic clone containing the globulin-1 gene was digested by Xho I and Pst I. A 0.77 kb fragment containing the exon 4/intron 5/a portion of exon 5 was purified as the globulin-1 specific probe.

Analyses of the Northern blots are summarized in FIG. 1. Both the lipid biosynthetic genes (delta-9 and delta-12 desaturases) are expressed in all tissues/organs examined although at various levels. The expression of the desaturases seems coordinately regulated in embryos, but have different levels of expression spatially. The transcript homologous to the fad2-1 cDNA was most abundant in the embryos at 15 DAP, and the message level declined toward maturation. The same developmental expression profile was detected for the delta-9 desaturase gene. There are high levels of expression of fad2-1 in both leaves and tassels, less in roots, and low but detectable in sheath. The delta-9 desaturase gene expressed at a lower level in these four tissues examined.

In order to down regulate the genes encoding the delta-9 desaturase, or the microsomal delta-12 desaturase, a seed-specific promoter which is expressed earlier than the target genes, or at least with timing that matches that of the target gene, would be highly desirable. Specifically, a promoter that is embryo/aleurone-specific is desired, since these are the tissues that store oil. The same promoter will be equally suitable for over-expression of a trait gene in the developing corn embryos. Therefore, there are two known maize genes which are good sources of promoter sequences, globulin-1 (Belanger and Kriz, 1989, Plant Physiol., 91: 636–643) and oleosin 16 kDa (Vance and Huang, 1987, J. Biol. Chem. 262: 11275–11279). The expression profiles of these genes were also characterized by Northern blot analysis.

The steady state level of globulin-1 transcripts began to accumulate at 20 DAP and reached a maximum level at a relatively late developmental stage (30 DAP). Although oleosin 16 kDa gene and globulin-1 are both tightly regulated spatially and are expressed only in seeds (Belanger and Kriz, 1989, Plant Physiol., 91: 636–643; Vance and Huang, 1988, J. Biol. Chem. 163; 1476–1481), the oleosin 16 kDa expression level is much higher judged by the strong hybridization signal in the embryo samples at all developmental stages (15–30 DAP) that were examined. The timing of oleosin 16 kDa expression is also much earlier than the globulin-1 gene. Immunofluoresent microscopy showed that oleosin 16 kDa protein is confined to the embryo and aleurone layer of developing seeds (Vance and Huang, 1988, J. Biol. Chem. 163; 1476–1481). Therefore, it was concluded that the oleosin 16 kDa promoter would be superior to globulin-1 promoter for driving trait genes over-expression in corn embryos, and the timing of the expression would be optimal to down regulate the genes involved in lipid biosynthetic pathway.

Example 5

Isolation and Sequencing of a Corn Embryo and Aleurone-Specific Promoter

The profile of gene expression for oleosin 16 kDa was compared to the lipid biosynthetic genes and globulin-1, as shown in FIG. 1. It was concluded that oleosin 16 kDa is a very good source from which to isolate an embryo/aleurone specific promoter sequence.

Corn oleosin proteins contain three major structural domains; a largely hydrophilic domain at the N-terminus, a hydrophobic hairpin α-helical domain at the center, and an amphipathic α-helical domain at the C-terminus. However, oleosin 18 kDa and 16 kDa amino acid and nucleotide sequences are highly similar only at the central domain (Qu and Huang, 1990, J. Biol. Chem. 265: 2238–2243). Primers (SEQ ID NOS:16 and 17) were designed based on the published sequence of oleosin 18 kDa (accession # J05212, GenBank).

```
5'-AGGCGCTGACGGTGGCGACGCT-3'    SEQ ID NO:16

5'-GTGTTGGCGAGGCACGTGAG-3'      SEQ ID NO:17
```

These primers hybridize to the central domain region of the oleosin 18 kDa cDNA sequence. RT-PCR (Perkin-Elmer, Norwalk, Conn.) was performed using the total RNA purified from developing corn embryos and the above primer pairs to generate a unique 0.23 kb fragment. The fragment was gel purified, and $^{32}$P-labeled as a probe to screen a corn genomic library (Missouri 17 line, in λFixII vector, Stratagene). Positive genomic clones were identified and recovered after three rounds of purification.

An oleosin 16 kDa-specific oligomer ("3221-ATG", SEQ ID NO:18) was synthesized.

```
5'-ACCTCCCGTCGCACCCCGGTGGTGATCAGCCATGGTAGGCTAGCAG-3'    SEQ ID NO:18
```

This oligonucleotide contains a sequence complementary to the sequence flanking the translation start codon of oleosin 16 kDa gene. Specifically, the oligonucleotide is complementary to the region beginning 12 nucleotides prior to the translations start ATG and extending another 33 nucleotides into the coding region). This oligomer was labeled with $^{32}$P using [γ-$^{32}$P]ATP and T4 polynucleotide kinase (Life Technologies, Gaithersburg, Md.), and used to screen the positive genomic clones described above. One of the clones, λ3221, containing an insert of 15 kb, was identified as hybridizing strongly to the oligomer probe. DNA was purified from clone λ3221, digested with various restriction enzymes, electrophoresed on an agarose gel, and blotted onto a Zeta-probe nylon membrane (Stratagene). The same $^{32}$P labeled oligomer (3221-ATG) was used as a probe to the λ3221 restricted DNA blot to identify fragments containing the upstream sequences. Based on the hybridization signal patterns of various restriction digestion, and oleosin 16 kDa cDNA sequence, the λ3221 DNA was subcloned as the follows. The DNA of λ3221 was digested with Xho I and Xba I, and cloned into the pBluescript vector (pSK (–), Stratagene) previously cut by the same enzymes. The transformants were screened by the hybridization to the $^{32}$P-labeled 3221-ATG oligomer. Positive clones were isolated. One of the clones (pBN164) was confirmed by sequencing to contain the elements of the upstream, 5'-leader, and the N-terminal part of the coding region of the oleosin 16 kDa gene.

The 1.7 kb sequence of the upstream region of oleosin 16 kDa gene in pBN164 is shown in SEQ ID NO:19. The transcription initiation site (+1) was identified at nucleotide position 1609 on the basis of primer extension data. This is 92 base pairs upstream of the ATG translation start codon. The putative TATA box (TATAAA) is located at position 1565–1571, 37–43 base pairs upstream of the transcription initiation site. Another TA-rich box is identified at position 1420–1426. These two TA-rich boxes are located in a region that is unusually GC-rich for an upstream element. The 5'-untranslated leader sequence is also GC-rich. There is a GC content of 67% from position 1326 to 1700, in contrast to a GC content of only 38% from position 1 to 1325. Southern blot analysis was conducted using genomic DNA purified from corn line LH192 (Holdens Foundation Seeds, IA), hybridized with oleosin 16 kDa-specific probe. The result indicates that corn oleosin 16 kDa is encoded by one or two genes.

Example 6

Oleosin 16 kDa Promoter Deletion Assay

The relative activities of promoters from oleosin 16 kDa, and globulin-1, were analyzed using a transient expression assay. The 35S promoter of cauliflower mosaic virus was used as a positive control. The transient expression cassette used β-glucuronidase (GUS) as the reporter gene, fused with the 3'-end of the nopaline synthase gene (NOS) to provide a polyadenylation signal. The putative promoter fragment of olesoin 16 kDa contains the full-length (1.7 kb, SEQ ID NO:19) of the upstream fragment of oleosin 16 kDa gene. The globulin-1 promoter contained a 1.1 kb upstream fragment from globulin-1 gene. The plasmid DNA was prepared according to the standard procedures (Wizard Miniprep kit, Promega, Madison, Wis.), coated onto gold particles, and bombarded into immature corn embryos dissected from cobs at 18–19 DAP. Nine embryos were placed onto each plate, and 3 plates were bombarded for every construct tested. After bombardment, the embryos were incubated at 37° in a substrate solution containing X-Gluc (Jefferson, 1989, Nature 342: 837–838) for 12 hours, and blue foci that developed indicating expression of the GUS gene were counted under the microscope. The result showed only minimal promoter activity was provided by the full-length upstream fragment of the oleosin 16 kDa gene, indicating there may be a negative regulatory element present in this region.

A number of oleosin 16 kDa promoters of varying length were designed to remove the potential negative regulatory element, and determine the optimal length with a high activity without losing its tissue specificity. Progressive deletions from the 5'- or 3'-end of this upstream sequence were made using PCR, or by restriction digests. The primers used in PCR, and the resulting putative promoter fragments, along with the corresponding nucleotide positions in SEQ ID NO:19 are shown in Table 1. The exon 1/intron 1 fragment (nucleotide position 1138–2220 in accession # X02382, GenBank) of maize shrunken-1 gene was cloned into the 5'-untranslated region as described below to further optimize the expression cassette.

TABLE 1

Putative promoter fragments from the oleosin 16 kDa gene.

| Promoter fragment (size in kb) | Primers used in PCR[a] | Nucleotide position (as in SEQ ID1) | 5'-untranslated sequence |
|---|---|---|---|
| f168 (1.7)[b] | — | 1–1700 | Native oleosin 16 kDa 5'-leader[c] |
| f184 (1.7)[a] | u: I, d: J | 1–1700 | Sh1 |
| f222 (1.1) | u: A, d: E | 512–1619 | Sh1 |
| f220 (0.9) | u: B, d: E | 749–1619 | Sh1 |
| f218 (0.55) | u: C, d: E | 1075–1619 | Sh1 |
| f236 (0.4)[b] | — | 1254–1700 | Native oleosin 16 kDa 5'-leader |
| f254 (0.95) | u: B, d: H | 749–1700 | Native oleosin 16 kDa 5'-leader |
| f235 (1.4) | u: D, d: F | 99–1501 | Sh1 |
| f231 (1.0) | u: A, d: F | 512–1501 | Sh1 |
| f232 (0.75) | u: B, d: F | 749–1501 | Sh1 |
| f233 (0.4) | u: C, d: F | 1075–1501 | Sh1 |
| f227 (1.2) | u: D, d: G | 99–1346 | Sh1 |
| f228 (0.8) | u: A, d: G | 512–1346 | Sh1 |
| f229 (0.6) | u: B, d: G | 749–1346 | Sh1 |
| f230 (0.3) | u: C, d: G | 1075–1346 | Sh1 |

[a]PCR was conducted using the pBN164 plasmid DNA as the template, and upstream (u) and downstream (d) primers specified as indicated, except for f184, in which pBN168 was used as the template. A restriction enzyme recognition site (underlined) was built in most of the primers to facilitate the cloning.

```
A:  5'-CTTATGTAATAGAAAAGACAGGATCCATATGG-3'        (SEQ ID NO:20)

B:  5'-GAGGAGTGAGGATCCTGATTGACTATCTCATTC-3'       (SEQ ID NO:21)

C:  5'-TCTGGACACCCTACCATTGGATCCTCTTCGGAG-3'       (SEQ ID NO:22)

D:  5'-AGAGTTGGATCCGTGTACAACTTGGTCTCTGG-3'        (SEQ ID NO:23)

E:  5'-GCCGCTGATGCTCGAGCTACGACTACGAGTGAGGTAG-3'   (SEQ ID NO:24)

F:  5'-ATGCGGGACTCGAGTCGGGGCAGCGCGACAC-3'         (SEQ ID NO:25)

G:  5'-GTGGCGGGGCCGAATCTCGAGTGGGCCGTAGT-3'        (SEQ ID NO:26)

H:  5'-GCCACGTGCCATGGTAGGCTAGCAGAGCGAGCT-3'       (SEQ ID NO:27)

I:  5'-AACACACACCCATGGATATCACAG-3'                (SEQ ID NO:28)

J:  5'-GGTCTGACTTACGGGTGTC-3'                     (SEQ ID NO:29)
``` b. Fragment f168 was obtained by cutting pBN164 plasmid DNA with Xba I and Nco I. The fragment contain the full-length upstream region in pBN164. (A Nco I site is naturally present in the position of translation start codon in oleosin 16 kDa gene). Fragment f236 was present in pBN236. pBN236 was obtained by cutting pBN168 with Spe I and Xba I, blunt-end treated by Klenow enzyme, and religated.

c. The transcription initiation site (+1) is at nucleotide position 1609 in SEQ ID NO:19. Therefore, the 5'-leader sequence is considered from 1609–1700.

d. Sh1 includes the sequence of exon I/intron I (nucleotide position 1138–2220, in accession # X02382, GenBank) of maize shrunken-1 gene.

Three intermediate expression constructs, pML63, pSH12, and pSM100, were made. pML63 (FIG. 2A) was derived from the commercial available vector pGEM-9Zf(-) (Promega), with an insert containing the 35S promoter, the GUS coding region, and a NOS 3'-region. Plasmid pSH12 contains an exon 1/intron 1 fragment (Sh1) of corn shrunken-1 gene, inserted in between the 35S promoter, and GUS coding region of pML63. The Sh1 fragment (nucleotide position of 1139–2230, in accession # X02382, GenBank) was obtained using a PCR approach. A pair of primers (SEQ ID NOS:30 and 31) were synthesized. The upstream primer (SEQ ID NO:30) contains an Xho I (underlined), and the downstream primer (SEQ ID NO:31) contains a Nco I site (underlined). These sequences were derived from the published sequence of maize sucrose synthase gene (X02382, GenBank) were used in PCR in which used DNA from a corn genomic library (Missouri 17 line, in λFixII vector, Stratagene) as the template.

```
5'-CTCTCCCGTCCTCGAGAAACCCTCC-3'      SEQ ID NO:30

5'-CTTGGCAGCCATGGCTCGATGGTTC-3'      SEQ ID NO:31
```

The resulting 1.1 kb fragment was gel-purified, digested with Xho I and Nco I enzymes, and inserted into the Xho I and Nco I site of pML63 to become pSH12 (FIG. 2B).

Plasmid pSM100 contains a globulin-1 promoter, Sh1 in the 5'-untranslated region, GUS gene, and a Nos 3'-end (FIG. 2C). The globulin-1 promoter was obtained from a genomic clone isolated from a corn genomic library (constructed in EMBL3, Clontech, Palo Alto, Calif.) using end-labeled oligomers (SEQ ID NOS:32 and 33) as probes in the screening. The sequences of the oligomers are based on the globulin-1 cDNA sequence available as GenBank accession M24845).

```
5'-ATGGTGAGCGCCAGAATCGTTGTCCTCCTC-3'    SEQ ID NO:32

5'-CATCCTGGCGGTCACCATCCTCAGGAGCGT-3'    SEQ ID NO:33
```

A positive clone with an insert about 10 kb hybridized to both the oligomer probes was confirmed to have the globulin-1 gene. A 0.45 kb fragment 5 to the start codon was obtained from PCR using the 10 kb clone as the template. Primers used in the amplification of the 0.45 kb segment are presented in SEQ ID NOS:34 and 35. The upstream primer (SEQ ID NO:34) contains a site for the enzyme EcoRI (underlined), and the downstream primer contains a site for the enzyme NcoI (underlined).

```
5'-ATAGGGAATTCTCTGTTTTTCTAAAAAAAA-3'    SEQ ID NO:34

5'-GCTCACCATGGTGTAGTGTCTGTCACTGTG-3'    SEQ ID NO:35
```

The fragment was purified and cut with EcoRI and NcoI, inserted into a vector with comparable sites for cloning. A 0.66 kb Hind III-EcoRI fragment immediately upstream of the 0.45 kb region was cut out from the 10 kb clone and ligated upstream to the 0.45 kb fragment, giving rise to a final 1.1 kb globulin-1 promoter fragment. This clone was used in PCR with globulin-1 promoter-specific primers (SEQ ID NOS:36 and 37). The upstream primer (SEQ ID NO:36) contains a site for BamHI (underlined), and the downstream primer (SEQ ID NO:37) contains a site for XhoI (underlined).

```
5'-GGGGGATCCAAGCTTGAGGAGACAGGAGATAAAAGT-3'      SEQ ID NO:36

5'-GGGCTGCAGCTCGAGGGTGTAGTGTCTGTCACTGTGATA-3'   SEQ ID NO:37
```

The resulting 1.1 kb PCR fragment was purified, digested with BamHI and XhoI, and inserted into the BamHI and XhoI sites of pSH12 to replace the 35S promoter. The resulting plasmid is designated as pSM100 (FIG. 2C).

All putative oleosin 16 kDa promoter fragments (listed in Table 1) were gel-purified before cloning into the expression vector. The f168 fragment was inserted into the XbaI and NcoI site of pML63 (to replace the original 35S promoter in the construct), and the new construct was named pBN168.

The purified PCR fragments described in Table 1 were digested with the corresponding restriction enzymes designed into the primers (BamHI and XhoI for f222, f220, f218, f235, f231, f232, f233, f227, f228, f229, and f230), and inserted into the expression vector (pSM 100) previously digested by the same enzymes in order to replace the globulin-1 promoter. Fragment f184 was cut with Nco I, and inserted into the NcoI site of pBN168. The resulting construct, pBN184, contained the native oleosin 16 kDa 5'-leader sequence with the Sh1 element in the 5'-untranslated region. Fragment f254 was digested with BamHI and NcoI, and inserted into the BamHI/NcoI site of pML63.

The different promoters and 5'-untranslated fragments contained in these constructs are listed in Tables 1 and 2. The sequences of each of these promoters (as derived from the full length 1.7 kb promoter, and not including the restriction sites introduced during the cloning) are set forth in the sequence listings, as follows. SEQ ID NO:38 is the 1.1 kb promoter fragment, SEQ ID NO:39 is the 0.9 kb promoter fragment, SEQ ID NO:40 is the 0.55 kb promoter fragment, SEQ ID NO:41 is the 0.95 kb promoter fragment, SEQ ID NO:42 is the 1.4 kb promoter fragment, SEQ ID NO:43 is the 1.0 kb promoter fragment, SEQ ID NO:44 is the 0.75 kb promoter fragment, SEQ ID NO:45 is the 0.4 kb promoter fragment, SEQ ID NO:46 is the 1.3 kb promoter fragment, SEQ ID NO:47 is the 0.8 kb promoter fragment, SEQ ID NO:48 is the 0.6 kb promoter fragment, SEQ ID NO:38 is the 1.1 kb promoter fragment, and SEQ ID NO:49 is the 0.3 kb promoter fragment.

Purified plasmid DNAs from these constructs were used in the transient expression assays as described previously. GUS staining assay results indicating promoter activities are summarized in Table 2.

TABLE 2

Oleosin 16 kDa promoter deletion assay.

| Plasmid | Construct | Promoter activity[a] |
|---|---|---|
| pBN168 | pOle-1.7kb5'::GUS::Nos3' | +/− |
| pBN184 | pOle-1.7kb5'::Sh::GUS::Nos3' | − |
| pBN222 | pOle-1.1kb5'::Sh::GUS::Nos3' | +++ |
| pBN220 | pOle-0.9kb5'::Sh::GUS::Nos3' | +++++ |
| pBN218 | pOle-0.55kb5'::Sh::GUS::Nos3' | ++++ |
| pBN254 | pOle-0.95kb5'::GUS::Nos3' | + |
| pBN236 | pOle-0.4kb5'::GUS::Nos3' | +/− |
| pBN235 | pOle-1.4kb5'''::Sh::GUS::Nos3' | ++ |
| pBN231 | pOle-1.0kb5'''::Sh::GUS::Nos3' | ++ |
| pBN232 | pOle-0.75kb5'''::Sh::GUS::Nos3' | ++ |
| pBN233 | pOle-0.4kb5'''::Sh::GUS::Nos3' | ++ |
| pBN227 | pOle-1.3kb5'''::Sh::GUS::Nos3' | + |
| pBN228 | pOle-0.8kb5'''::Sh::GUS::Nos3' | + |
| pBN229 | pOle-0.6kb5'''::Sh::GUS::Nos3' | + |
| pBN230 | pOle-0.3kb5'''::Sh::GUS::Nos3' | + |
| pSM100 | pGlo-1.1kb5'::Sh::GUS::Nos3' | ++ |

[a]Promoter activity was measured by a transient expression assay of the reporter gene, GUS. The + was assigned based on the visual estimation of the intensity and counts of the blue foci. −:0, +/−: 0–1; +: 2–10; ++:10–50; +++: 50–100; ++++: 50–100, but significantly darker blue than +++; +++++: >150 blue foci.

The full-length promoter (as contained in pBN168 and pBN184), whether or not in conjunction with the Sh1 intron element, confers non-detectable or minimal promoter activity in the transient expression system. Promoter activity was increased when this region was progressively deleted from the far upstream end. It appears that there is a negative-regulatory element in this far upstream region (1–511). Deletion of this region as in pBN222 significantly increased the GUS expression as compared to the activity of pBN184 in the assay. Removal of yet more sequence, up to nucleotide position 748, further enhanced the activity of the promoter, as was demonstrated with construct pBN220. However, promoter activity decreased if the upstream sequence was deleted beyond position 748 (pBN218 vs. pBN220).

Inclusion of the TATA box (1566–1571) is important for attaining high promoter activity. However, the upstream TATA-rich element (1420–1436) can substituted for the TATA box (1566–1571), albeit with a significantly lower activity. The function of the GC-rich region (1326–1700) surrounding the TATA boxes is not apparent from these data. Minimal promoter activities was still detected when the entire GC-rich region, including both the TATA boxes, was deleted.

Intron enhancement is very important in optimizing gene expression. None of the constructs lacking the Sh1 element provided any significant level of GUS expression in the assay. The oleosin 16 kDa promoter with an optimized length and composition, as in pBN220, was found to be stronger than the globulin-1 promoter (as contained in pSM100). The results of the Northern blot analyses characterizing early timing of expression in the young developing corn embryos, combined with the demonstration of its high activity in the expression assay, indicated that the optimal embryo/aleurone-specific promoter is the 0.9 kb fragment (SEQ ID NO:39) isolated from the oleosin 16 kDa gene combined with a Sh1 exon 1/intron 1 element in the 5'-untranslated region.

Example 7

Corn Embryo/Aleurone-Specific Expression Constructs with Lipid Trait Genes

Expression constructs comprising a maize oleosin 16 kDa promoter (0.9 kb in length, Table 1 and 2, and SEQ ID NO:39), an intron1/exon1 element (1.1 kb) from the shrunken-1 gene located between (3' to) the promoter and (5' to) the cDNA fragment, a cDNA fragment encoding a portion of the trait gene in either sense or antisense orientation with respect to the promoter, and a Nos 3'-end located 3' to the cDNA fragment, were constructed and used in corn transformation to alter the level of the enzyme encoded by the trait gene in corn grains (FIGS. 3B–3F). The construct design is suitable to express any target trait gene not mentioned in this patent in a corn embryo/aleurone-specific manner. The selectable marker on the vector backbone may be any antibiotic (e.g., ampicillin, hygromycin, kanamycin) resistant gene.

An intermediate construct, pBN256, modified from pBN220 was made as the starting vector for the various expression constructs with lipid trait genes. pBN220 was digested with NcoI and EcoRI to delete the GUS coding sequence, end-filled with dNTPs and Klenow fragment of DNA polymerase I, and re-ligated. The resulting plasmid was designated pBN256 (FIG. 3A).

PCR was used to obtain a fragment containing the fad2-1 coding region with Kpn I restriction site at both ends. The fad2-1 cDNA clone was used as the template with primers (SEQ ID NOS:50 and 51) specific to the fad2-1 sequence each containing a site for KpnI (underlined).

5'-CGG<u>GGTACC</u>GATGACCGAGAAGGAGCGGG-3'   SEQ ID NOS:50

5'-GGC<u>GGTACC</u>TAGAACTTCTTGTTGTACCA-3'   SEQ ID NOS:51

The expected 1.2 kb fragment was gel-purified, digested with Kpn I, and cloned into a vector with a comparative Kpn I site to facilitate propogation and further manipulation. The Kpn I fragment was digested out from this new construct, and the ends were blunted as above, inserted into the Sma I site of pBN256, to become pBN257. This clone contains a near full-length of fad2-1 coding region, but the ATG translation start codon is out of frame (FIG. 3B).

A DNA fragment containing the delta-9 desaturase coding region was recovered by PCR using the delta-9 desaturase cDNA clone (SEQ ID NO:8) DNA as the template and coding region-specific primers (SEQ ID NOS:52 and 53) that contained NcoI sites. The resulting fragment was gel purified, cut by Nco I, and inserted into the Nco I site of the modified pBN220 in which the GUS gene had been previously removed.

5'-GGCCTCCG<u>CCATGG</u>CGCTCCGCTCCACGACG-3'   SEQ ID NOS:52

5'-CTCCAACTCAAGCAGTCG<u>CCATGG</u>GTTTCC-3')   SEQ ID NOS:53

(Plasmid pBN220 was cut by Nco I and Sma I to remove the GUS gene, end-filled in by Klenow treatment, and religated as the modified GUS-free vector.) The resulting clones contained a truncated corn delta-9 desaturase coding region (approximately 0.9 kb, comprising 79% of the full-length coding sequence) in each of the two possible orientations, sense (pBN264, FIG. 3C) and antisense (pBN262, FIG. 3D).

The 0.9 kb Nco I fragment of the delta-9 desaturase gene (SEQ ID NO:8) was also cloned into the Nco I site of pBN257 to create a construct, pBN414, containing a fused trait gene of fad2-1 and delta-9 desaturase, both in the sense orientation, as shown in FIG. 3E. The coding sequence of fad2-1 in pBN414 is out of frame as in pBN257, and its C-terminal sequence was interrupted by the insertion of the delta-9 desaturase fragment (79% of the full length coding region shown in SEQ ID NO:8).

The second delta-9 desaturase clone (SEQ ID NO:10) was cut by EcoRI, and the 1.1 kb EcoRI fragment was purified and inserted into the EcoRI site of pBN257 to create a new construct, pBN412 (FIG. 3F), containing a fused trait gene of delta-9 desaturase and fad2, both in sense orientation. In pBN412, the delta-9 desaturase fragment contains a full-length coding region (SEQ ID NO:10). The translation start codon ATG for the delta-9 desaturase is in frame in pBN412, but fad2 coding sequence is out of frame.

Example 8

Transgenic Corn a. Corn Transformation

The chimeric genes described above can be introduced into corn cells by the following procedure. Immature corn embryos are dissected from developing caryopses derived from crosses of the inbred corn lines H99 and LH132, or from crosses of the inbred orn lines H99 and LH195, or a public High II line (Armstrong, 1991, Maize Genetics Co. News Letter 65:92–93), or any corn lines which are transformable and regenerable. The embryos are isolated 10 to 11 days after pollination when they are 1.0 to 1.5 mm long. The embryos are then placed with the axis-side facing down and in contact with agarose-solidified N6 medium (Chu et al., (1975) Sci. Sin. Peking 18:659–668). The embryos are kept in the dark at 27°. Friable embryogenic callus proliferates from the scutellum of these immature embryos. It consists of undifferentiated masses of cells with somatic proembryoids and embryoids borne on suspensor structures. The embryogenic callus isolated from the primary explant can be cultured on N6 medium and sub-cultured on this medium every 2 to 3 weeks. The plasmid, p35S/Ac (obtained from Dr. Peter Eckes, Hoechst Ag, Frankfurt, Germany) may be used in transformation experiments along with the trait gene (co-bombardment) in order to provide for a selectable marker. This plasmid contains the Pat gene (see European Patent Publication 0 242 236) which encodes phosphinothricin acetyl transferase (PAT). This gene is from *Streptomyces viridochromogenes*, and its sequence is found as GenBank accession X65195. The enzyme PAT confers resistance to herbicidal glutamine synthetase inhibitors such as phosphinothricin (also available as the compound designated gluphosinate). The pat gene in p35S/Ac is under the control of the 35S promoter from Cauliflower Mosaic Virus (Odell et al. (1985) *Nature* 313:810–812) and the 3' region of the nopaline synthase gene (NOS 3'-end) from the T-DNA of the Ti plasmid of Agrobacterium tumefaciens. Alternatively, the gel-purified pat gene fragment, including the 35S promoter, pat gene coding region, and the NOS 3'-end, may be used as the selectable marker. It will be appreciated by the skilled worker that the fragment used to provide selection in transformations can vary considerably, and that any fragment containing the 35S promoter operably linked to the pat gene is capable of providing the desired selectable trait. Another gene that is useful as a selectable marker for resistance to phosphinothricin, and which may be provided on a plasmid or as a separate DNA fragment, is the bar gene from *Streptomyces hygroscopicus* (GenBank accession X17220).

The particle bombardment method (Klein et al., (1987) *Nature* 327:70–73) was used to transfer genes to the callus culture cells. According to this method, gold particles (0.6 μm or 1 μm in diameter) were coated with DNA using the following technique. Approximately 10 μg of plasmid DNAs were added to 50 μL of a suspension of gold particles (60 mg per mL). Calcium chloride (50 μL of a 2.5 M solution) and spermidine free base (20 μL of a 1.0 M solution) were added to the particles. The suspension was vortexed during the addition of these solutions. After 10 minutes, the tubes were briefly centrifuged (5 sec at 15,000 rpm) and the supernatant was removed. The particles were resuspended in 200 μL of absolute ethanol, centrifuged again and the supernatant was removed. The ethanol rinse was performed again and the particles were resuspended in a final volume of 30 μL of ethanol. An aliquot (5 μL) of the DNA-coated gold particles was then placed in the center of a Kaptonä flying disc (Bio-Rad Labs). The embryogenic tissue was placed on filter paper over agarose-solidified N6 medium. The tissue was arranged as a thin lawn that covered a circular area of about 5 cm in diameter. The petri dish containing the tissue was placed in the chamber of the PDS-1000/He approximately 8 cm from the stopping screen. The air in the chamber was evacuated to a vacuum of 28 inches of Hg. The DNA-coated particles were accelerated into the corn tissue with a Biolisticä PDS-1000/He (Bio-Rad Instruments, Hercules Calif.), using a helium pressure of 1000 psi, a gap distance of 0.5 cm and a flying distance of 1.0 cm.

Seven days after bombardment the tissue was transferred to N6 medium that contained gluphosinate (5 mg per liter) and lacked casein or proline. The tissue continued to grow slowly on this medium. After an additional 2 weeks the tissue was transferred to fresh N6 medium containing gluphosinate (selection medium). The tissue was cultured on the selection medium and was transferred every 2 weeks for a total 3–4 passages. Areas of about 1 cm in diameter of actively growing callus were identified on some of the plates containing the selection medium. These calli continued to grow when sub-cultured on the selective medium.

Plants were regenerated from the transgenic callus by first transferring clusters of tissue to N6 medium supplemented with 0.2 mg per liter of 2,4-D (regeneration medium). After 2–3 weeks the tissues began to form somatic embryo-like structures and showed green areas when the tissues are transferred and grown under light. Plantlets emerged after a total of 3–4 weeks on regeneration medium, and were transferred individually into plant tissue culture vessels containing the regeneration medium. After sufficient growth of root and shoot, the plantlets were transplanted to 4 inches pots in the growth chamber, and later re-potted into 10–12 inches pots, and grown to maturity in the greenhouse (Fromm et al., (1990) *Bio/Technology* 8:833–839).

b. Transgenic Corn with High Saturate Fatty Acid Composition in the Grain

Using biolistic gun method described above, corn callus was co-bombarded with pBN262 plasmid DNA, and the bar gene fragment. Stable transformants were selected according to procedures described above, and transgenic corn plants were regenerated. Primary transformants (designated as R0 plants) were grown in the greenhouse. The plants were either selfed or crossed using wild type pollen from Holdens line LH132. The cobs were harvested at 30 DAP. Embryos were dissected out of kernels, and sterilized. Small pieces of scutella were taken from each individual embryo and used for fatty acid composition assays by the GC method as described in WO 94/11516. The remaining embryos were planted in tissue culture vessels containing the regeneration medium. Embryos with a positive phenotype (i.e., a high level of saturated fatty acids in the lipid fraction) were transplanted from the culture vessels in pots, and grown into R1 plants in the greenhouse. The mature R1 plants were either selfed or crossed with the wild type pollen from line 5-12-24, Pioneer Hybrid International, Johnston, Iowa). The cobs were harvested at 45 DAP, and R2 kernels were collected. Small piece of scutella were taken from individual kernels, and used for analyses of their fatty acids.

Two independent transgenic lines were identified as having a high saturated fatty acid phenotype, FA013-2-4 and FA013-3-2.

FIG. 4A shows a typical example of the phenotype of R1:2 kernel segregants from a single cob harvested from a R1 plant of line FA013-2-4. The R0 generation of this plant was cross-pollinated with wild-type pollen from LH132 (Holden). The cob was harvested and lipid composition of single kernels analyzed. The results shows a 1:1 (high saturate phenotype: wild type) seed segregation indicating the presence of a single transgene insertion locus in FA013-2-4. A heterozygous kernel that contained 26.1% of stearic acid (vs. wild type as 2%) was planted and grown into a R1 plant. The R1 plant was selfed, and the data from analyses of the R2 seeds indicated a segregation ratio as 3:1 (FIGS. 4A and 4B), confirming that FA013-2-4 contains a single locus of transgene insertion, and that the trait phenotype is dominant. In the R2 seed segregants, the stearate content in the kernels ranged from 27–43%, and the average fatty acid composition was 13% 16:0, 37% 18:0, 4% 18:1, 39% 18:2, 2.8% 18:3, and 0.5% 20:0 and 20:1. The total saturate fatty acid content was 54%. The maximum saturated fatty acid content was found to be as high as 61%. This was in a line that had an overall composition of 13% 16:0, 43% 18:0, 3% 18:1, 34% 18:2, 2.3% 18:3, 4.6% 20:0, and 0.2% 20:1. This is compared to the composition of the wild-type segregants profile of 16% 16:0, 2% 18:0, 19% 18:1, 63% 18:2, 1.0% 18:3, and 0.1% 20:0. The wild-type segregants had a total saturated fatty acid content of 18%.

The germination rate of seed from line FA013-2-4 is close to 100% in standard growth chamber conditions, indicating that the saturated fatty acid content in embryo/aleurone does not affect the seed viability.

FIG. 5 shows a typical example of the phenotype and segregation of R1:2 kernels harvested from two R1 plants of line FA013-3-2-15. Their respective R0 plant was selfed, and the corresponding R1 plants were both cross-pollinated with the wild type pollen from line 5-12-24. The first plant was derived from a R0:1 kernel originally containing 12% stearate, and the second plant from a kernel with 21% stearate content. However, the maximal stearate content of R1:2 kernels from both plants reaches up to 38–39%. The range of variation in the R1:2 kernels stearate levels was 29–38%, and 16–39%, respectively. This indicated the presence of a single transgene insertion locus in line FA013-3-2-15 based on the segregation ratio. The average total saturate content was more than 50%, and the seed germination rate for this line was about 40%.

R3:4 seeds were obtained from homozygous plant of FA013-2-4 event. The lipid composition of the homozygous grains was, on average, 15% 16:0, 15% 18:0, 14% 18:1, 53% 18:2, 1.5% 18:3, 1.5% 20:0, and 0.5% 20:1. However, kernels harvested from a heterozygous plant at the same R3:4 generation contains a higher stearate content (31% versus the 15% from the homozygous background). A similar result was obtained in the grains harvested from the crossing using this heterozygous plant as the pollen donor onto a hybrid female plant (34K77, DuPont) in the TopCross® (TC) grain production method (Table 3).

TABLE 3

Kernel lipid composition in R0:1, homozygous and heterozygous R3:4, and various crossing of FA013-2-4.

| Genotype | Phenotype (%) | | | | | | |
|---|---|---|---|---|---|---|---|
| | 16:0 | 18:0 | 18:1 | 18:2 | 18:3 | 20:0 | 20:1 |
| R0:1 × LH132 | 14 | 23 | 12 | 47 | 4 | | |
| R3:4 selfed (homozygous) | 15 | 15 | 14 | 53 | 1.5 | 1.5 | 0.5 |
| R3:4 selfed (heterozygous)[a] | 12 | 31 | 8 | 44 | 2.4 | 3.0 | 0.3 |
| 34K77(TC) × R3[a] | 12 | 32 | 7 | 45 | 2.1 | 2.7 | 0.3 |
| WT[b] | 15 | 1.2 | 18 | 65 | 0.7 | 0.3 | 0.3 |

[a]The data represent the average lipid composition from kernals with the positive phenotype. The kernels of R3:4 were from the selfed cob of the heterozygous R3 plant. The same R3 plant was used as the pollen donor to pollinate 34K77 plants.
[b]A few 34K77 plants were selfed to obtained the wild-type kernels as the control.

Using processes similar to those described above, new transgenic events with high stearate—and hence high saturate—phenotypes were generated (Table 4). The trait gene constructs used in these experiments are from either pBN264 or pBN427 (FIG. 7A). Plasmid pBN264 is similar to the pBN262, except that the delta-9 desaturase is in a sense orientation relative to the promoter. The transgene sequence is contained within a Sal I fragment (position 3248–44) of pBN427 and is identical to the corresponding Sal I fragment of pBN264 (position 2–3206). However, pBN427 uses a vector backbone with a hygromycin resistance selectable marker (HPT, from pKS17, described in WO 94/11516), versus the ampicillin marker in pBN262 and pBN264. The transgene prepared for the bombardment were either the restriction enzyme digested and agarose gel purified DNA fragment from pBN264 (for events derived from the FA025 experiment, the transgene fragment was marked as fBN264), or the intact pBN427 plasmid DNA (for events derived from the FA029 experiment). The restriction enzyme used to cut out the transgene may be Sal I or Xba I, which release a transcriptionally functional transgene fragment of 3.2 kb, which can then be purified following agarose gel electrophoresis. The use of a transgene DNA fragment, rather than the entire plasmid, allows the recovery of transgenic events which do not contain a bacterial antibiotic resistance gene.

TABLE 4

Transgenic events with high stearate phenotype

| | Transgenic events | Stearate[a] | Total Sat.[b] | Construct[c] | Co-supp. freq.[d] |
|---|---|---|---|---|---|
| | Wild-type | <2% | 18% | | |
| 1) | FA025-1-4 | 16–27% | 32–42% | fBN264 | |
| 2) | FA025-2-1 | 12–39% | 28–60% | fBN264 | |
| 3) | FA025-2-12 | 17–39% | 50–55% | fBN264 | 6/30 = 20% |
| 4) | FA025-2-17 | 10% | 27% | fBN264 | |
| 5) | FA025-3-5 | 22–27% | 41–48% | fBN264 | |
| 6) | FA025-3-9 | 6–35% | 22–53% | fBN264 | |
| 7) | FA029-2-4 | 17–34% | 32–50% | pBN427 | |
| 8) | FA029-2-5 | 18–25% | 35–42% | pBN427 | |

TABLE 4-continued

Transgenic events with high stearate phenotype

| Transgenic events | Stearate[a] | Total Sat.[b] | Construct[c] | Co-supp. freq.[d] |
|---|---|---|---|---|
| 9) FA029-2-7 | 29% | 46% | pBN427 | |
| 10) FA029-3-2 | 9–33% | 25–50% | pBN427 | 5/25 = 20% |
| 11) FA029-3-4 | 26–29% | 40–43% | pBN427 | |

[a]Typically, 20 kernels from 4 sibling cobs of each event were analyzed on the single kernel basis. The range indicates the lowest to the highest stearate content from the single kernel result of that event.
[b]Total saturate fatty acids = 16:0 + 18:0 + 20:0.
[c]f = purified fragment, p = intact plasmid DNA.
[d]Co-suppression frequency = total number of events showing positive phenotype/total number of basta resistant clones generated from the respective transformation experiment.

Transgenic phenotypes in the new events were determined by the lipid composition in single kernels harvested from fully matured cobs using the same GC method described above. The sampling was non-destructive because only very small pieces of embryos were cut out from individual kernels and used for fatty acid composition assays. The kernels remain viable and can be planted in either the greenhouse or the field for propogatiom of the next generation.

Table 4 shows transgenic events identified with high stearate (and high total saturate fatty acids) phenotypes at the R0:1 generation. Typically, lipid assays were performed on 5–20 kernels from each cob, taken from 4–6 cobs from sibling plants for each transgenic event. The stearate and total saturate fatty acid contents are shown as percentage in oil, and the ranges presented indicate the lowest to highest percentages among all the single kernels analyzed in the event.

The results indicate that a consistently high frequency (10–20%) of co-suppression events may be obtained in corn (Table 4 and 6), whether using intact plasmid DNA or purified fragment. However, a small portion of vector DNA contamination may still be present in the preparations of purified fragment, and Southern blot analysis may be performed to verify the events truly free of a bacterial selectable marker. The Southern blot analysis that were performed indicated that use of a DNA fragment tends to generate events with simpler insertion patterns (one or few copies transgene insertion), than using the intact plasmid DNA. The latter may form complex concatemers and integrate together into the plant genome when used in the biolistic method, resulting in a complex insertion locus which may cause some transgene instability.

c. Transgenic Corn with a High Oleic Acid Content in Grains

Corn callus was co-bombarded with pBN257 DNA (SEQ ID NO:58) and a bar gene fragment, transgenic corn plants were produced, and R0:1 kernels were harvested and lipid composition analyzed as described above.

One transgenic event, FA014-5-1, was identified with a high oleate phenotype. FIG. 6 shows a typical example of segregation of R0:1 seeds harvested from a single cob, and their corresponding phenotypes. The cob was harvested from a wild type female plant (LH132), pollinated with pollen from a transgenic plant of line FA014-5-1. The ratio of positive phenotype: wild-type=1:1, indicating that line FA014-5-1 contains a single locus insertion, and the high oleate transgene trait may be dominant. The lipid profile of the positive phenotype is, on average, 12% 16:0, 1.3% 18:0, 70% 18:1, 15% 18:2, and 1.4% 18:3. The highest content of oleic acid found in samples taken from this cob was 81%, and in one of other cobs the content of oleic acid in some of the kernels was 83%. Accumulation of high levels of oleic acid is at the expense of linoleate, as shown in FIG. 6. There is about 2–4% decrease in palmitic acid, without any major change in 18:0, 18:3, 20:0 or 20:1 contents.

R3:4 kernels were harvested from homozygous plants, with the lipid composition as 10% 16:0, 1.5% 18:0, 68% 18:1, 19% 18:2, and 0.8% 18:3. The composition result is similar to that of the heterozygous R0:1 with a 2% lower oleate content, indicating that genotypic background may influence the transgenic phenotype. When the transgenic homozygous R3 plants were used as the pollen source, and crossed onto the high oil inbred lines QX47 (which possesses a total oil content of 14%), QH102 (which possesses a total oil content of 9%), or a hybrid line 34K77 in the TopCross® grain production method (U.S. Pat. Nos. 5,704, 160 and 5,706,603), the respective lipid composition of kernels in each crossing are shown in Table 5. Oleate content in kernels from pure QX47 line is ~43%, and the crossing of FA014-5-1 with this line also resulted in a higher oleate content in the grains (79% versus 68% from kernels of the homozygous FA014-5-1 plants). The total oil content of grains from crossing FA014-5-1 to QX47 is 8%–10%, and is 6%–7% from crossing FA014-5-1 to QH102.

TABLE 5

Kernel lipid composition in R0:1, homozygous R3:4, and various crossing of FA014-5-1.

| | Phenotype | | | | |
|---|---|---|---|---|---|
| Genotype | 16:0 | 18:0 | 18:1 | 18:2 | 18:3 |
| R0:1 × LH132 | 12 | 1.3 | 70 | 15 | 1.7 |
| R3:4 selfed[a] | 10 | 1.5 | 68 | 19 | 0.8 |
| QX47(HO) × R3 | 9 | 2 | 79 | 10 | 0.4 |
| QH102(HO) × R3 | 10 | 2 | 71 | 16 | 0.5 |
| 34K77 (TC) × R3 | 10 | 1 | 71 | 16 | 0.7 |
| WT[b] | 15 | 1.2 | 18 | 65 | 0.7 |

[a]The kernels were from selfed homozygous R3 plants. The same homozygous plants were used as the pollen source for the crossing with the female plants listed below.
[b]A few 34K77 hybrid plants were selfed to obtain the wild-type kernels as the control.

Using similar processes, new transgenic events with high oleate phenotypes were generated (Table 6). The trait gene constructs used in these experiments are from either pBN257 or pBN428 (FIG. 7B). The transgene sequence in Sal I fragment (position 44–3468) of pBN428 is identical to the Sal I fragment of pBN257 (position 2–3426), except that pBN428 is using a vector backbone with a hygromycin resistance selectable marker gene (HPT, from pKS17, described in WO94/11516), versus the ampicillin selection in pBN257. The transgene prepared for bombardment was either the restriction enzyme digested and agarose gel purified DNA fragment, or the intact plasmid DNA as indicated in Table 6. The restriction enzyme used to cut out the transgene may be Sal I or Xba I, which release a transcriptionally functional transgene fragment of 3.4 kb, and can be purified by agarose gel electrophoresis.

TABLE 6

Transgenic events with high oleate phenotype

| | Transgenic events | Oleate[a] | Construct[b] | Co-suppression freq.[c] |
|---|---|---|---|---|
| | Wild-type | ~22% | | |
| 1) | FA014-5-1 | ~70% | pBN257 | 1/10 = 10% |
| 2) | FA027-1-9 | 60–69% | fBN257 | |
| 3) | FA027-4-1 | 79–87% | fBN257 | 3/20 = 15% |
| 4) | FA027-4-5 | 81–87% | fBN257 | |
| 5) | FA028-1-8 | 39–63% | pBN428 | |
| 6) | FA028-1-10 | 50–55% | pBN428 | |
| 7) | FA028-3-1 | 64–78% | pBN428 | 4/32 = 13% |
| 8) | FA028-3-3 | 30–83% | pBN428 | |
| 9) | FA030-2-1 | 78–82% | fBN428 | |
| 10) | FA030-2-9 | 82–83% | fBN428 | 6/61 = 10% |
| 11) | FA030-3-1 | 80–84% | fBN428 | |
| 12) | FA030-3-3 | 40–68% | fBN428 | |
| 13) | FA030-4-25 | 42–77% | fBN428 | |
| 14) | FA030-5-17 | 71–86% | fBN428 | |
| 15) | FA031-5-8 | 58–76% | fBN428 | 1/6 = 17% |

[a]Typically, 20 kernels from 4 sibling cobs of each event were analyzed on the single kernel basis. The range indicates the lowest to the highest stearate content from the single kernel result of that event.
[b]f = purified fragment, p = intact plasmid DNA.
[c]Co-suppression frequency = total number of events showing positive phenotype/total number of basta resistant clones generated from the respective transformation experiment.

Two of the high oleate events, FA027-4-1 and FA027-4-5 were carried forward to the R1:2 generation. The oleate content of kernels from these progenies indicated a consistent high oleate phenotype (81–87% oleate by single kernel analyses).

d. Transgenic Corn with High Levels of Saturated and Oleic Acids in Kernels

Corn with a high level of saturated fatty acid and a high level of oleic acid in kernels may be produced by crossing a high saturate transgenic line (FA013-2-4 or FA013-3-2) and the high oleate transgenic line (FA014-5-1), or by crossing the high saturate transgenic line with a high oleic acid mutant such a lines B73OL or AEC272OL (WO95/22598).

An alternative approach for obtaining a corn plant high in both saturated fatty acids and oleic acid is to create a transgenic line with a transgene construct containing the fused fad2 and delta-9 desaturase genes, such as in pBN412 or pBN414 or pBN431 (FIG. 7C), or the transformation may be done by co-bombardment with both pBN257 (or pBN428) and pBN264 (or pBN427 or pBN262).

Transgenic events comprisng the chimeric gene from pBN431 possess a phenotype in which the total saturate level is not less than about 30% of the total seed oil content, the stearic acid level is in the range from about 11% to 31% of the total seed oil content and the oleic acid level is in the range from about 27% to about 37% of the total seed oil content. It is believed that oils may be obtained which possess an oleic acid level in the range from about 35% to about 45% of the total seed oil content by crossing these transgenic events with a line having a high oleic acid phenotype, e.g., any of the transgenic events set forth in Table 6 above, or B73OL or AEC272OL which are referred to above.

The high stearic acid and high oleic acid corn oil resulting from such a transgenic event may be used in a blended or unblended form as a margarine or shortening, and it may be blended with a high palmitic acid fat to form a cocoa butter substitute.

What is claimed is:

1. A method of feeding an animal comprising feeding the animal a corn grain obtained from a transgenic corn plant comprising in its genome a chimeric gene selected from the group consisting of:

(i) a first chimeric gene comprising an isolated nucleic acid fragment encoding a corn delta-9 stearoyl ACP desaturase comprising the amino acid sequence set forth SEQ ID NO:9 wherein all or a part of the first isolated nucleic acid is useful in co-suppressing an endogenous gene encoding a corn delta-9 stearoyl ACP desaturase, or the complement thereof, and linked to a second chimeric gene comprising a second isolated nucleic acid fragment encoding a corn delta-12 desaturase wherein said second fragment has a nucleic acid sequence identity of at least 90% based on the Clustal method of alignment when compared to a nucleic acid as set forth in SEQ ID NO:1, wherein all or a part of the isolated second nucleic acid fragment is useful in co-suppressing an endogenous gene encoding a corn delta-12 desaturase, or the complement thereof, operably linked to at least one regulatory sequence;

(ii) a chimeric gene comprising (a) a first isolated nucleic acid fragment encoding a corn delta-9 stearoyl ACP desaturase comprising the amino acid sequence set forth in SEQ ID NO:9 wherein all or a part of the isolated first nucleic acid fragment is useful in co-suppressing an endogenous gene encoding a corn delta-9 stearoyl ACP desaturase, or the complement thereof, (b) a second isolated nucleic acid fragment encoding a corn delta-12 desaturase wherein said second fragment has a nucleic acid sequence identity of at least 90% based on the Clustal method of alignment when compared to a nucleic acid as set forth in SEQ ID NO:1, wherein all or a part of the isolated second nucleic acid fragment is useful in co-suppressing an endogenous gene encoding a corn delta-12 desaturase, or the complement thereof, and (c) a third isolated nucleic acid fragment comprising a corn oleosin promoter comprising the nucleotide sequence set forth in any of SEQ ID NOS: 38–40 and 42–49 wherein the isolated nucleic acid fragments of (a), (b) and (c) are operably linked;

(iii) a chimeric gene comprising (a) a first isolated nucleic acid fragment encoding a corn delta-9 stearoyl ACP desaturase comprising the amino acid sequence set forth in SEQ ID NO:9 wherein all or a part of the isolated first nucleic acid fragment is useful in co-suppressing an endogenous gene encoding a corn delta-9 stearoyl ACP desaturase, or the complement thereof, (b) a second isolated nucleic acid fragment encoding a corn delta-12 desaturase wherein said second fragment has a nucleic acid sequence identity of at least 90% based on the Clustal method of alignment when compared to a nucleic acid as set forth in SEQ ID NO:1, wherein all or a part of the isolated second nucleic acid fragment is useful in co-suppressing an endogenous gene encoding a corn delta-12 desaturase, or the complement thereof, and (c) a shrunken 1 intron/exon, operably linked to at least one regulatory sequence wherein (a), (b) and (c) are operably linked; or (iv) a chimeric gene comprising (a) a first isolated nucleic acid fragment encoding a corn delta-9 stearoyl ACP desaturase comprising the amino acid sequence set forth in SEQ ID NO:9, or the complement thereof, (b) a second isolated nucleic acid fragment encoding a corn delta-12 desaturase wherein said second fragment has a nucleic acid sequence identity of at least 90% based on the Clustal method of alignment when compared to a nucleic acid as set forth in SEQ ID NO:1, or the complement thereof, (c) a third isolated nucleic acid fragment comprising a corn oleosin promoter comprising the nucleotide sequence set forth in any of SEQ ID NOS: 38–40 and 42–49, and (d) a shrunken 1 intron/exon wherein (a), (b), (c) and (d) are operably linked;

and further wherein expression of the chimeric gene results in an altered corn oil phenotype compared to the oil phenotype of a non transgenic corn grain.

2. A method of feeding an animal comprising feeding the animal a corn grain obtained from a transgenic corn plant comprising in its genome a chimeric gene selected from the group consisting of:

(i) a first chimeric gene selected from the group consisting of:

(a) a chimeric gene comprising an isolated nucleic acid fragment encoding a corn delta-9 stearoyl ACP desaturase comprising the amino acid sequence set forth in SEQ ID NO:9, wherein all or part of the isolated nucleic acid fragment is useful in co-suppressing an endogenous gene encoding a corn delta-9 stearoyl ACP desaturase, or the complement thereof, operably linked to at least one regulatory sequence;

(b) a chimeric gene comprising (1) an isolated nucleic acid fragment encoding a corn delta-9 stearoyl ACP desaturase comprising the nucleotide sequence set forth in SEQ ID NO:9 wherein all or a part of the isolated nucleic acid fragment is useful in co-suppressing an endogenous gene encoding a corn delta-9 stearoyl ACP desaturase, or the complement thereof, and (2) an isolated nucleic acid fragment comprising a corn oleosin promoter comprising the nucleotide sequence set forth in any of SEQ ID NOS: 38–40 and 42–49 wherein the isolated nucleic acid fragments of (1) and (2) are operably linked;

(c) a chimeric gene comprising (1) an isolated nucleic acid fragment encoding a corn delta-9 stearoyl ACP desaturase comprising the amino acid sequence set forth in SEQ ID NO:9 wherein all or part of the isolated nucleic acid fragment is useful in co-suppressing an endogenous gene encoding a corn delta-9 stearoyl ACP or the complement thereof, and 2) a shrunken 1 intron/exon, operably linked to at least one regulatory sequence, wherein the isolated nucleic acid fragments of (l) and (2) are operably linked; or (d) a chimeric gene comprising (1) an isolated nucleic acid fragment encoding a corn delta-9 stearoyl ACP desaturase comprising the amino acid sequence set forth in SEQ ID NO:9 wherein all or part of the isolated nucleic acid fragment is useful in co-suppressing an endogenous gene encoding a corn delta-9 stearoyl ACP desaturase, or the complement thereof, (2) an isolated nucleic acid fragment comprising a corn oleosin promoter comprising the nucleotide sequence set forth in any of SEQ ID NOS: 38–40 and 42–49, and (3) a shrunken 1 intron/exon wherein (1), (2) and (3) are operably linked, and (ii) a second chimeric gene selected from the set consisting of:

(a) a chimeric gene comprising an isolated nucleic acid fragment encoding a corn delta-12 desaturase wherein said fragment has a nucleic acid sequence identity of at least 90% based on the Clustal method of alignment when compared to a nucleic acid as set forth in SEQ ID NO:1, wherein all or part of the isolated nucleic acid fragment is useful in co-suppressing an endogenous gene encoding a corn delta-12, or the complement thereof, operably linked to at least one regulatory sequence;

(b) a chimeric gene comprising (1) an isolated nucleic acid fragment encoding a corn delta-12 desaturase wherein said fragment has a nucleic acid sequence identity of at least 90% based on the Clustal method of alignment when compared to a nucleic acid as set forth in SEQ ID NO:1, wherein all or part of the isolated nucleic acid fragment is useful in co-suppressing an endogenous gene encoding a corn delta-12, or the complement thereof, and (2) an isolated nucleic acid fragment comprising a corn oleosin promoter comprising the nucleotide sequence set forth in any of SEQ ID NOS: 38–40 and 42–49 wherein the isolated nucleic acid fragments of (1) and (2) are operably linked;

(c) a chimeric gene comprising (1) an isolated nucleic acid fragment encoding a corn delta-12 desaturase wherein said fragment has a nucleic acid sequence identity of at least 90% based on the Clustal method of alignment when compared to a nucleic acid as set forth in SEQ ID NO:1, wherein all or part of the isolated nucleic acid fragment is useful in co-suppressing an endogenous gene encoding a corn delta-12 desaturase, or the complement thereof, and (2) a shrunken 1 intron/exon, operably linked to at least one regulatory sequence, wherein the isolated nucleic acid fragments of (1) and (2) are operably linked; or (d) a chimeric gene comprising (1) an isolated nucleic acid fragment encoding a corn delta-12 desaturase wherein said fragment has a nucleic acid sequence identity of at least 90% based on the Clustal method of alignment when compared to a nucleic acid as set forth in SEQ ID NO:1, wherein all or part of the isolated nucleic acid fragment is useful in co-suppressing an endogenous gene encoding a corn delta-12, or the complement thereof, (2) an isolated nucleic acid fragment comprising a corn oleosin promoter comprising the nucleotide sequence set forth in any of SEQ ID NOS: 38–40 and 42–49, and (3) a shrunken 1 intron/exon, wherein (1), (2) and (3) are operably linked; and further wherein expression of the chimeric genes results in an altered corn oil phenotype compared to the oil phenotype of a non transgenic corn grain.

* * * * *

UNITED STATES PATENT AND TRADEMARK OFFICE
CERTIFICATE OF CORRECTION

| | |
|---|---|
| PATENT NO. | : 7,008,664 B1 |
| APPLICATION NO. | : 09/326285 |
| DATED | : March 7, 2006 |
| INVENTOR(S) | : Jennie Bih-Jien Shen |

It is certified that error appears in the above-identified patent and that said Letters Patent is hereby corrected as shown below:

Column 108,
Line 52, after "12" insert -- desaturase --.

Column 110,
Line 1, after "12" insert -- desaturase --.

Signed and Sealed this

Twenty-seventh Day of June, 2006

JON W. DUDAS
*Director of the United States Patent and Trademark Office*